US012600763B2

(12) United States Patent
Brown et al.

(10) Patent No.: US 12,600,763 B2
(45) Date of Patent: *Apr. 14, 2026

(54) COMPOSITIONS AND METHODS FOR THE DELIVERY OF THERAPEUTIC BIOLOGICS FOR TREATMENT OF DISEASE

(71) Applicant: Halozyme Hypercon, Inc., Boston, MA (US)

(72) Inventors: Paul Brown, Boston, MA (US); Tyler L Carter, Newburyport, MA (US); Lyndon Fitzgerald Charles, Jr., Medford, MA (US); Chase Spenser Coffman, Newton, MA (US); Daniel Benjamin Dadon, East Boston, MA (US); Lisa Liu, Somerville, MA (US); Sadiqua Shadbar, Allston, MA (US); Chaitanya Sudrik, Stoneham, MA (US); Yi Tang, Medford, MA (US); Shankul Vartak, Cambridge, MA (US)

(73) Assignee: Halozyme Hypercon, Inc., Boston, MA (US)

( * ) Notice: Subject to any disclaimer, the term of this patent is extended or adjusted under 35 U.S.C. 154(b) by 397 days.

This patent is subject to a terminal disclaimer.

(21) Appl. No.: 17/883,427

(22) Filed: Aug. 8, 2022

(65) Prior Publication Data

US 2022/0389084 A1     Dec. 8, 2022

Related U.S. Application Data

(63) Continuation of application No. 17/351,963, filed on Jun. 18, 2021, now Pat. No. 11,459,376, which is a continuation of application No. PCT/US2020/050508, filed on Sep. 11, 2020.

(60) Provisional application No. 63/024,703, filed on May 14, 2020, provisional application No. 62/899,907, filed on Sep. 13, 2019, provisional application No. 62/899,981, filed on Sep. 13, 2019.

(51) Int. Cl.
    *C07K 16/00* (2006.01)
    *A61K 45/06* (2006.01)
(52) U.S. Cl.
    CPC .............. *C07K 16/00* (2013.01); *A61K 45/06* (2013.01)
(58) Field of Classification Search
    CPC .......... A61K 9/14; A61K 9/10; A61K 9/1623; A61K 9/1652; A61K 45/06; A61K 47/14; A61K 38/00; A61K 39/395; C07K 16/00; A61P 35/00
    USPC ..................................................... 424/133.1
    See application file for complete search history.

(56) References Cited

U.S. PATENT DOCUMENTS

| | | | |
|---|---|---|---|
| 3,013,007 | A | 12/1961 | Dale et al. |
| 3,882,036 | A | 5/1975 | Krezanoski et al. |
| 4,172,896 | A | 10/1979 | Uno et al. |
| 4,531,056 | A | 7/1985 | Abowsky et al. |
| 5,358,970 | A | 10/1994 | Ruff et al. |
| 5,427,798 | A | 6/1995 | Ludwig et al. |
| 5,541,231 | A | 7/1996 | Ruff et al. |
| 5,595,721 | A | 1/1997 | Kaminski et al. |
| 5,612,055 | A | 3/1997 | Bedford et al. |
| 5,677,180 | A | 10/1997 | Robinson et al. |
| 5,731,000 | A | 3/1998 | Ruff et al. |
| 5,736,137 | A | 4/1998 | Anderson et al. |
| 5,739,169 | A | 4/1998 | Ocain et al. |
| 5,763,493 | A | 6/1998 | Ruff et al. |
| 5,801,005 | A | 9/1998 | Cheever et al. |
| 5,824,311 | A | 10/1998 | Greene et al. |
| 5,830,880 | A | 11/1998 | Sedlacek et al. |
| 5,840,731 | A | 11/1998 | Mayer et al. |
| 5,846,945 | A | 12/1998 | Mccormick |
| 5,874,029 | A | 2/1999 | Subramaniam et al. |
| 6,095,134 | A | 8/2000 | Sievers et al. |
| 6,110,973 | A | 8/2000 | Young |
| 7,001,888 | B2 | 2/2006 | Tidmarsh et al. |
| 8,013,022 | B2 | 9/2011 | Deangelo et al. |
| 8,512,754 | B2 | 8/2013 | Needham |
| 8,728,525 | B2 | 5/2014 | Brown et al. |
| 8,939,388 | B1 | 1/2015 | Beetz et al. |
| 9,259,701 | B2 | 2/2016 | Palmer et al. |
| 9,364,542 | B2 | 6/2016 | Chang |
| 9,597,385 | B2 | 3/2017 | Caplan |
| 9,643,996 | B2 | 5/2017 | Petrel et al. |
| 11,077,059 | B2 | 8/2021 | Coffman et al. |

(Continued)

FOREIGN PATENT DOCUMENTS

| | | |
|---|---|---|
| CN | 1750811 A | 3/2006 |
| CN | 103908432 A | 7/2014 |

(Continued)

OTHER PUBLICATIONS

Capelle, M.A.H. et al., "High throughout screening of protein formulation stability: Practical considerations," European Journal of Pharmaceutics and Biopharmaceutics, vol. 65; 131-148 (2007).

(Continued)

*Primary Examiner* — Yan Xiao

(74) *Attorney, Agent, or Firm* — Hamilton, Brook, Smith & Reynolds, P.C.

(57) ABSTRACT

The present disclosure provides compositions and methods for treating a disease or condition in a subject in need thereof, comprising administering to the subject a pharmaceutically effective amount of a composition comprising a plurality of particles comprising at least one therapeutic biologic suspended in a pharmaceutically acceptable liquid carrier.

18 Claims, 5 Drawing Sheets

(56) References Cited

U.S. PATENT DOCUMENTS

| | | |
|---|---|---|
| 11,459,376 B2 | 10/2022 | Brown et al. |
| 11,510,995 B2 | 11/2022 | Sanchez Martin et al. |
| 11,654,112 B2 | 5/2023 | Coffman et al. |
| 11,717,488 B2 | 8/2023 | Brown et al. |
| 11,795,429 B2 | 10/2023 | Bitterfield et al. |
| 12,115,262 B2 * | 10/2024 | Coffman ............... A61K 9/1688 |
| 12,178,913 B2 | 12/2024 | Coffman et al. |
| 12,263,249 B2 | 4/2025 | Coffman et al. |
| 12,263,253 B2 | 4/2025 | Coffman et al. |
| 12,377,050 B2 | 8/2025 | Auer et al. |
| 12,433,849 B2 | 10/2025 | Coffman et al. |
| 2001/0031801 A1 | 10/2001 | Lyons et al. |
| 2002/0081732 A1 | 6/2002 | Bowlin et al. |
| 2003/0055010 A1 | 3/2003 | De Haan |
| 2004/0197469 A1 | 10/2004 | Lyons et al. |
| 2005/0013868 A1 | 1/2005 | Brynjelsen et al. |
| 2005/0019410 A1 | 1/2005 | Johnson |
| 2005/0186183 A1 | 8/2005 | Deangelo et al. |
| 2006/0002862 A1 | 1/2006 | Truong-Le et al. |
| 2006/0147400 A1 | 7/2006 | Piot |
| 2006/0292224 A1 | 12/2006 | Moore et al. |
| 2008/0026068 A1 | 1/2008 | Brown et al. |
| 2008/0095849 A1 | 4/2008 | Wu et al. |
| 2009/0035381 A1 | 2/2009 | Stankus et al. |
| 2009/0226530 A1 | 9/2009 | Lassner et al. |
| 2009/0274765 A1 | 11/2009 | Beduneau et al. |
| 2010/0047248 A1 | 2/2010 | Darvari et al. |
| 2010/0092526 A1 | 4/2010 | Baker et al. |
| 2010/0092778 A1 | 4/2010 | Watanabe et al. |
| 2010/0305500 A1 | 12/2010 | Lambert et al. |
| 2010/0330169 A1 | 12/2010 | Bunick et al. |
| 2011/0223208 A1 | 9/2011 | Hill et al. |
| 2011/0280864 A1 | 11/2011 | Johnston et al. |
| 2012/0076800 A1 | 3/2012 | Dai et al. |
| 2012/0157591 A1 | 6/2012 | Rufner et al. |
| 2012/0244196 A1 | 9/2012 | Okubo et al. |
| 2012/0258914 A1 | 10/2012 | Kumar et al. |
| 2013/0256931 A1 | 10/2013 | Palmer et al. |
| 2014/0052020 A1 | 2/2014 | Allen et al. |
| 2014/0262694 A1 | 9/2014 | Knigge |
| 2014/0263694 A1 | 9/2014 | Lin et al. |
| 2014/0271843 A1 | 9/2014 | Ma et al. |
| 2014/0288282 A1 | 9/2014 | Petrel et al. |
| 2014/0303356 A1 | 10/2014 | Gramer et al. |
| 2014/0308270 A1 | 10/2014 | Lobo et al. |
| 2014/0348852 A1 | 11/2014 | Vos et al. |
| 2014/0378370 A1 | 12/2014 | Johnston et al. |
| 2014/0378655 A1 | 12/2014 | Anderson |
| 2015/0079395 A1 | 3/2015 | Cruise et al. |
| 2015/0157576 A1 | 6/2015 | Shum et al. |
| 2016/0015640 A1 | 1/2016 | Propst et al. |
| 2016/0128944 A1 | 5/2016 | Chawrai et al. |
| 2016/0250329 A1 | 9/2016 | Bukrinski et al. |
| 2016/0271064 A1 | 9/2016 | Sell et al. |
| 2017/0210554 A1 | 7/2017 | Black et al. |
| 2018/0333493 A1 | 11/2018 | Shenoy |
| 2019/0142957 A1 * | 5/2019 | Teran ....................... A61K 9/08 514/19.3 |
| 2019/0374470 A1 | 12/2019 | Coffman et al. |
| 2020/0253875 A1 | 8/2020 | Coffman et al. |
| 2020/0268695 A1 | 8/2020 | Sanders |
| 2021/0220289 A1 | 7/2021 | Coffman et al. |
| 2021/0309724 A1 | 10/2021 | Brown et al. |
| 2021/0315827 A1 | 10/2021 | Brown et al. |
| 2021/0322317 A1 | 10/2021 | Coffman et al. |
| 2021/0403599 A1 | 12/2021 | Badovinac-Crnjevic et al. |
| 2022/0211627 A1 | 7/2022 | Arrighi et al. |
| 2023/0065628 A1 | 3/2023 | Auer et al. |
| 2023/0094393 A1 | 3/2023 | Charles et al. |
| 2023/0181473 A1 | 6/2023 | Auer et al. |
| 2023/0338299 A1 | 10/2023 | Paul et al. |
| 2023/0355530 A1 | 11/2023 | Coffman et al. |
| 2024/0255517 A1 | 8/2024 | Carter et al. |
| 2024/0270864 A1 | 8/2024 | Brown et al. |
| 2024/0293332 A1 | 9/2024 | Brown et al. |
| 2024/0415782 A1 | 12/2024 | Coffman et al. |
| 2025/0025425 A1 | 1/2025 | Brown et al. |
| 2025/0026811 A1 | 1/2025 | Brown et al. |
| 2025/0064744 A1 | 2/2025 | Coffman et al. |
| 2025/0082736 A1 | 3/2025 | Brown et al. |
| 2025/0186348 A1 | 6/2025 | Coffman et al. |
| 2025/0228790 A1 | 7/2025 | Coffman et al. |
| 2025/0288525 A1 | 9/2025 | Auer et al. |

FOREIGN PATENT DOCUMENTS

| | | | |
|---|---|---|---|
| EP | 0677332 | A2 | 10/1995 |
| EP | 3236987 | B1 | 3/2020 |
| EP | 2773330 | B1 | 9/2020 |
| JP | 2003-513710 | A | 4/2003 |
| JP | 2005-504090 | A | 2/2005 |
| JP | 2005-504764 | A | 2/2005 |
| JP | 2008-266128 | A | 11/2008 |
| JP | 2010-524948 | A | 5/2010 |
| JP | 2011-079747 | A | 4/2011 |
| JP | 2011-241223 | A | 12/2011 |
| JP | 2012-500799 | A | 1/2012 |
| JP | 2012-508744 | A | 4/2012 |
| JP | 2013-166100 | A | 8/2013 |
| JP | 2014-058466 | A | 4/2014 |
| JP | 2014-510077 | A | 4/2014 |
| JP | 2014-129357 | A | 7/2014 |
| JP | 2019-535832 | A | 12/2019 |
| WO | 99/11196 | A1 | 3/1999 |
| WO | 03/35301 | A1 | 5/2003 |
| WO | 2006/087354 | A2 | 8/2006 |
| WO | 2007/059782 | A1 | 5/2007 |
| WO | 2008/062908 | A1 | 5/2008 |
| WO | 2008/092084 | A2 | 7/2008 |
| WO | 2010/044867 | A1 | 4/2010 |
| WO | 2010/082543 | A1 | 7/2010 |
| WO | 2011/131943 | A2 | 10/2011 |
| WO | 2012/042274 | A1 | 4/2012 |
| WO | 2014/057424 | A2 | 4/2014 |
| WO | 2015/085898 | A1 | 6/2015 |
| WO | 2015/138844 | A1 | 9/2015 |
| WO | 2015/196091 | A1 | 12/2015 |
| WO | 2016/014497 | A1 | 1/2016 |
| WO | 2016/089309 | A1 | 6/2016 |
| WO | 2017/106716 | A1 | 6/2017 |
| WO | 2018/098376 | A1 | 5/2018 |
| WO | 2018/234489 | A1 | 12/2018 |
| WO | 2019/023392 | A1 | 1/2019 |
| WO | 2019/226969 | A1 | 11/2019 |
| WO | 2020/051307 | A1 | 3/2020 |
| WO | 2020/160323 | A2 | 8/2020 |
| WO | 2021/050953 | A1 | 3/2021 |
| WO | 2021/158959 | A2 | 8/2021 |
| WO | 2021/168271 | A1 | 8/2021 |
| WO | 2021/212019 | A1 | 10/2021 |
| WO | 2022/256840 | A2 | 12/2022 |
| WO | 2023/212721 | A1 | 11/2023 |
| WO | 2024/177927 | A1 | 8/2024 |
| WO | 2025/054552 | A1 | 3/2025 |

OTHER PUBLICATIONS

Clackson, T. et al., "Making antibody fragments using phage display libraries," Nature vol. 352; 624-628 (1991).

CN Search report Mailed on Jan. 13, 2024 for CN Application No. 2021800293477 (with English Translation).

CN Search report Mailed on Jul. 28, 2022 for CN Application No. 202080012222.9 (With English Translation).

English Translation of CN Office Action Mailed on Aug. 3, 2022 for CN Application No. 202080012222.9.

English translation of Office Action issued in Chinese Patent Application No. 201780072350.0, issued May 17, 2021 (16 pages).

Hui et al., "Progress in preparation of peptide protein drug microspheres," The medicine herald, Issue 10, 2007, pp. 1-32. (Concise explanation met by English Translation of Search report cited concurrently as Other Document 4).

Jones, A.J.S., "Analysis of Polypeptides and Proteins," Advanced Drug Delivery Reviews, vol. 10; 29-90 (1993).

(56) References Cited

OTHER PUBLICATIONS

Marks, J.D. et al., "By-passing Immunization Human Antibodies from V-gene Libraries Displayed on Phage," J. Mol. Biol., vol. 222; 581-597 (1991).
Persic, L. et al., "An integrated vector system for the eukaryotic expression of antibodies or their fragments after selection from phage display libraries," Gene; 9-18 (1997).
Press, O.W. et al., "Monoclonal Antibody 1F5 (Anti-CD20) Serotherapy of Human B Cell Lymphoma," Blood, vol. 69; No. 2; 584-591 (1987).
Reichardt, C., "Solvatochromic Dyes as Solvent Polarity Indicators," Chem. Rev., vol. 94; 2319-2358 (1994).
Richardson, H. et al., "Influence of the glass transition on solvent loss from spin-cast glassy polymer thin films," Eur. Phys. J. E, vol. 12; 021; S87-S91 (2003).
Sblattero, D. and Bradbury, A., "Exploiting recombination in single bacteria to make large phage antibody libraries," Nature Biotechnology, vol. 18; 75-80 (2000).
Supplementary Partial European Search Report for European Patent Application No. 17873547.8, dated Jun. 15, 2020 (9 pages).
Zhiqi, L., et al., "Functional Emulsifiers and Emulsions", China Light Industry Press, Apr. 30, 2000, 2 pages. (Concise explanation met by Translation of Search report being cited as Other Document 3 in IDS being cited concurrently).
Notice of Allowance for U.S. Appl. No. 17/351,963, mailed May 4, 2022.
Bock et al.,"Electrospraying of polymers with therapeutic molecules: state of the art," Prag Polym Sci. 37(11): 1510-1551 (2012)(67 pages).
Cloupeau et al., "Electrohydrodynamic spraying functioning modes: a critical review," J Aerosol Sci. 25(6): 1021-1036 (1994).
Elektrofi, Inc., Redefining the Delivery of Biologics, 11 pages, retrieved from Internet URL: https://www.elektrofi.com/welcome#technology on Nov. 15, 2021.
European Search Report and Search Opinion Received for EP Application No. 18838118, mailed on May 6, 2021, 12 pages.
Forgacs, E. et al., "Direct (Normal)-Phase High-Performance Liquid Chromatography," Chapter II.B. in Molecular Basis of Chromatographic Separation, CRC Press, Baco Raton, FL; 120-131 (1997).
Galam et al., "High-throughput assay for the identification ofHsp90 inhibitors based on Hsp90dependent refolding of firefly luciferase," available in PMC Mar. 1, 2008, published in final edited form as: Bioorg Med Chem. 15(5): 1939-1946 (2007) (16 pages).
Ganan-Calvo et al., "Current and droplet size in the electrospraying ofliquids. Scaling laws," J Aerosol Sci. 28(2): 249-275 (1997).
Gapinski et al., "Structure and dimensions of core-shell nanoparticles comparable to the confocal volume studied by means of fluorescence correlation spectroscopy," Langmuir. 32(10): 2482-2491 (2016).
Gikanga et al.," Manufacturing of High-Concentration Monoclonal Antibody Formulations via Spray Drying-the Road to Manufacturing Scale," PDA J Pharm Sci Technol. 69(1): 59-73 (2015) (16 pages).
Giugliano et al., "Efficacy, safety, and tolerability of a monoclonal antibody to proprotein convertase subtilisin/kexin type 9 in combination with a statin in patients with hypercholesterolaemia (LAPLACE-TIMI 57): a randomised, placebo-controlled, dose-ranging, phase 2 study," available in PMC Mar. 3, 2015, published in rmal edited form as: Lancet. 380(9858): 2007-17 (2012) (20pages).
Haggag et al., "Evaluation of nano spray drying as a method for drying and formulation of therapeutic peptides and proteins," Front Pharmacol. 6:140 (2015) (5 pages).
Hickey, J.W. et al., "Biologically Inspired Design ofNanoparticle Artificial Antigen-Presenting Cells for Immunomodulation," Nano Letters, vol. 17; 7045-7054 )2017).
Xie et al., "Encapsulation of protein drugs in biodegradable microparticles by co-axial electrospray," J Colloid Interface Sci. 317(2): 469-76 (2008).
Wanning et al., "Pharmaceutical spray freeze drying," Int J Pharm. 488(1-2): 136-53 (2015).

Wang et al., "FDA's regulatory science program for generic PLAI PLGA-based drug products," Am Phann Rev. <https://www.americanpharmaceuticalrevie,v.com/Featured-Articles/ 188841-FDA-s-Regulatory-Science-Program-for-Generic-PLA-PLGA-Based-Drug-Products/>, dated Jun. 15, 2016, retrieved on Jun. 27, 2022 (11 pages).
Vonhoff, Sebastian, Thesis: "The Influence of Atomization Conditions on Protein Secondary and Tertiary Structure During Microparticle Formation by Spray-Freezing-Drying," Doktorgrades Dr. rer. nat, Der Natunvissenschaftlichen Fakultat, der Friedrich-Alexander Universitat Erlangen—Ntimberg, 2010, Chapters 6.4.3-6.6 and 8; 45 pages.
International Search Report and Written Opinion received for PCT Patent Application No. PCT/US2020/050508, mailed on Dec. 3, 2020, 12 pages.
Vehring, "Pharmaceutical particle engineering via spray drying," Pharm Res. 25(5): 999-1022 (2008).
Torchilin. "Multifunctional nanocarriers," Adv Drua Deliv Rev. 58(14): 1532-55 (2006).
Takats et al., "Electrosonic spray ionization. A gentle technique for generating folded proteins and protein complexes in the gas phase and for studying ion-molecule reactions at atmospheric pressure," Anal Chem. 76(14): 4050-58 (2004).
Janssen Biotech Inc., "Highlights of prescribing information," <http://www.janssenlabels.com/package-insert/product-monograph/prescribinginformation/DARZALEX-pi.pdl>, dated Jul. 2019, retrieved on Aug. 22, 2019 (13 pages).
Kaltashov et al., "Electrospray ionization mass spectrometry can provide estimates of protein surface areas in solution," available in PMC Jan. 27, 2009, published in final edited form as: Anal Chem. 77(16): 5370-5379 (2005) (21 pages).
Kim et al., "Controlled production of emulsion drops using an electric field in a flow-focusing microfluidic device," Appl Phys Lett. 91: 133106 (2007) (3 Pages).
Ku et al., "Electrospray characteristics of highly viscous liquids," J Aerosol Sci. 33(10): 1361-1378 (2002).
Lal et al., "Clean western blot signals from immunoprecipitated samples," available in PMC Jan. 25, 2006, published in final edited form as: Mol Cell Probes. 19(6): 385-388 (2005) (5 pages).
Lavorini et al., "New inhaler devices—the good, the bad and the ugly," Respiration. 88(1): 3-15 (2014).
Lee et al., "Solid-state stabilization of a-Chymotrypsin and catalase with carbohydrates," Ind Eng Chem Res. 45(14): 5134-5147 (2006).
Li et al., "Effects of pulsed electric fields and heat treatment on stability and secondary structure of bovine immunoglobulin G," J Agric Food Chem. 53(3): 663-670 (2005).
Longman et al.," Identifying differences in solution Conformations ofhvo chimeric IgG3 antibodies through triple detection SEC," LCGC North America. 18(21): (2006) (5 pages).
Lopez-Herrera et al., "Coaxial jets generated from electrified Taylor cones. Scaling laws," J Aerosol Sci. 34(5): 535-552 (2003).
Miller et al., "Antibody nanoparticle dispersions formed with mixtures of crowding molecules retain activity and in vivo bioavailability," available in PMC Oct. 1, 2013, published in final edited form as: J Pharm Sci. 101(10): 3763-3778 (2012) (25 pages).
Miller et al., "Low viscosity highly concentrated injectable nonaqueous suspensions of lysozyme microparticles," available in PMC Feb. 17, 2011, published in final edited form as: Langmuir. 26(2): 1067-1074 (2010) (22 pages).
Moghadam et al., "Electro-spray of high viscous liquids for producing mono-sized spherical alginate beads," Particuology. 6(4): 271-275 (2008).
Morales-Cruz et al., "Two-step nanoprecipitation for the production of protein-loaded PLGA nanospheres," Results Pharma Sci. 2: 79-85 (2012).
Mueller et al.,"The rheology of suspensions of solid particles," Proc R Soc A. 466: 1201-1228 (2010).
Naqvi et al., "Living cell factories—electrosprayed microcapsules and microcarriers for minimally invasive delivery," Adv Mater. 28(27): 5662-71 (2016)(10 pages).
Nguyen et al., "Pharmaceutical applications of electrospraying," J Pharm Sci. 105(9): 2601-2620 (2016).

(56) References Cited

OTHER PUBLICATIONS

Park et al., "One step immobilization of protein encapsulated core/shell particles onto nanofibers," Macromol Mater Eng. 295(6): 544-550 (2010).

Patel et al. "Poloxamers: A pharmaceutical excipients with therapeutic behaviors", 2009, 15, International Journal of PharmTech Research, vol. (1), No. 2, pp. 299-303.

Pivnik, A.V., "Use of rituximab for treatment of HIV-infected patients with hematological disorders, " Genotekhnologiya Medical Center, Moscow, 7 pages; English Abstract Only (2013).

Saglam et al., "Preparation of high protein micro-particles using two-step emulsification," Food Hydrocolloids. 25(5):1139-48 (2011).

Serra-Peinado, C., et al., "Expression of CD20 after viral reactivation renders HIV-reservoir cells susceptible to Rituximab," Nature Communications, vol. 10; 15 pages (2019).

Shire et al., "Challenges in the development of high protein concentration formulations," J Pharm Sci. 93(6): 1390-402 (2004).

Allahham, D. et al., "Development and application of a microcapillary rheometer for in-vitro evaluation of parenteral Injectability," Journal of Pharmacy and Pharmacology, vol. 56; 709-716 (2004).

Aniket et al., "MicroglassificationTM: A novel technique for protein dehydration," J Pharm Sci. 103(3): 810-820 (2014).

Banerjee et al., "Electrospray ionization mass spectrometry: a technique to access the information beyond the molecular weight of the analyte," Int J Anal Chem. Article 282574 (2012) (40 pages).

Bogelein et al., "Cyclone selection influences protein damage during drying in a mini spray-dryer," Int J Pharm. 401 (1-2): 68-71 (2010).

Cloupeau et al., "Electrostatic spraying of liquids: Main functioning modes," J Electrostat. 25(2): 165-184 (1990).

Dias et al., "Tolerability of High-vol. Subcutaneous Injections of a Viscous Placebo Buffer: A Randomized, Crossover Study in Healthy Subjects," AAPS PharmSciTech. 16(5): 1101-1107 (2015).

Fernandez de la Mora et al., "The current emitted by highly conducting taylor cones," J Fluid Mech. 260: 155-184 (1994).

Yuan et al., "Coaxial electrospray of curcumin-loaded microparticles for sustained drug release," PLoS One. 10(7): e0132609 (2015) (15 pages).

Yuan et al., "One-step fabrication of triple-layered microcapsules by a tri-axial flow focusing device for microencapsulation of soluble drugs and imaging agents," Proc SPIE vol. 9711, Imaging, Manipulation, and Analysis of Biomolecules, Cells, and Tissues IX (2016) (12 pages).

Fernandez de la Mora et al., "The fluid dynamics of Taylor cones," Annu Rev Fluid Mech. 39: 217-43 (2007) (29 pages).

Informa Healthcare, Pharmaceutical Dosage Forms: Parenteral Medications, Third Edition, vol. 3: Regulations, Validation and the Future. Sandeep Nema and John D. Ludwig, vii-304 (2010) (328 pages).

Lee, Spray-Drying of Proteins. Rational Design of Stable Protein Formulations. Carpenter and Manning, 135-158 (2002).

Loscertales et al., "Micro/nano encapsulation via electrified coaxial liquid jets," Science. 295(5560): 1695-8 (2002).

Makadia et al., "Poly lactic-co-glycolic acid (PLGA) as biodegradable controlled drug delivery carrier," Polymers (Basel). 3(3): 1377-1397 (2011).

U.S. Department of Health and Human Services, "Q3C—Tables and List: Guidance for Industry," Aug. 2018 (10 pages).

Zhang et al., "Coaxial electrospray of microparticles and nanoparticles for biomedical applications," Expert Rev Med Devices. 9(6): 595-612 (2012).

Zhang et al., "Coaxial electrospray of ranibizumab-loaded microparticles for sustained release of anti-VEGF therapies," PloS One. 10(8):e0135608 (2015) (16 pages).

Ziabicki et al., "Crystal nucleation in an electric field," Macromol Symp. 104(1): 65-87 (1996).

Non-Final Office Action for U.S. Appl. No. 17/351,963, mailed Oct. 21, 2021.

Final Office Action for U.S. Appl. No. 17/351,963, mailed Feb. 1, 2022.

International Preliminary Report on Patentability for International Application No. PCT/US2020/050508, entitled: "Compositions and Methods for the Delivery of Therapeutic Biologics for Treatment of Disease," mailed Mar. 24, 2022.

Fenn et al., "Electrospray ionization for mass spectrometry of large biomolecules," Science. 246(4926):64-71 (Oct. 6, 1989).

Final Office Action for U.S. Appl. No. 18/906,489, mailed Feb. 14, 2025.

Frost, G.I., "Recombinant human hyaluronidase (rHuPH20): an enabling platform for subcutaneous drug and fluid administration," Expert Opinion Drug Deliv., vol. 4; No. 4; 427-440 (2007).

Gulfam, M. et al., "Anticancer Drug-Loaded Gliadin Nanoparticles Induce Apoptosis in Breast Cancer Cells," American Chemical Society, Langmuir, vol. 28; 8216-8223 (2012).

Hui et al., "Progress in preparation of peptide protein drug microspheres," The medicine herald, Issue 10, 2007, pp. 1-32. (Concise explanation met by English Translation of Search report attached).

Imamura, K et al., "Evaluation of Hydration States of Protein in Freeze-Dried Amorphous Sugar Matrix," J. Pharm. Sci., vol. 90; 1955-1963 (2001).

Imamura, K., "Sugar-Protein Interaction and Stabilization of Protein in Amorphous Sugar Matrix," Cryobiology and Cryotechnology, vol. 51; No. 1; 31-35 (2005). English Abstract included.

Jun, L., "Guizho Science and Technology Press", Agricultural building materials, Aug. 31, 1999, 4 pages (Concise explanation met by the attached English Translation of CN Appl 202080064558 office action).

Kaltashov et al., "Estimates of Protein Surface Areas in Solution by Electrospray Ionization Mass Spectrometry," available in PMC Jan. 27, 2009, published in final edited form as: Anal Chem. 77(16): 5370-5379 (2005).

Mardles. E. W. J., "Viscosity of Suspensions and the Einstein Equation," Nature. 145: 970 (Jun. 22, 1940).

Miller et al. (Low viscosity highly concentrated injectable nonaqueous suspension of lysosome microparticles, Languir, Jan. 19, 2010; 26 (2): 1067-1074). (Year: 2010).

Nema et al., Pharmaceutical Dosage Forms: Parenteral Medications, Third Edition, vol. 3: Requlations, Validation and the Future. Informa Healthcare, vii-304 (2010) (328 pages).

Non-Final Office Action for U.S. Appl. No. 18/906,489, mailed Nov. 29, 2024.

Papir, Y.S. and Krieger, I.M., "Rheological Studies on Dispersions of Uniform Colloidal Spheres," Journal of Colloid and Interface Science, vol. 34; No. 1; 126-130 (1970).

Pearlman, R. and Nguyen, T.H., "Analysis of Protein Drugs," Peptide and Protein Drug Delivery, Vincent Lee Ed., Marcel Dekker, Inc., New York, NY, pp. 247-301 (1991).

Plückthun, A., "Antibodies from *Escherichia coli*," In: The pharmacology of monoclonal antibodies, M. Rosenberg and G. P. Moore, Eds. (Springer Verlag, Berlin, 1994), vol. 113, pp. 269-315.

Sridhar, R. and Ramakrishna, S., "Electrosprayed nanoparticles for drug delivery and pharmaceutical applications," Biomatter, vol. 3; No. 3; e24281-1; 14 pages (2013).

Vehring, R. et al., "Particle formation in spray drying," Aerosol Science, vol. 38; 728-746 (2007).

Zhang, J. et al., "Fundamentals and applications of inertial microfluidics: a review," Lab Chip, vol. 16; 10-34 (2016).

English language abstract for JP 2010609243 A5, 2011, 1 page. (Year: 2011).

Nema et al., Pharmaceutical Dosage Forms: Parenteral Medications, Third Edition, vol. 3: Regulations, Validation and the Future. Informa Healthcare, vii-304 (2010) (328 pages).

Non-Final Office Action for U.S. Appl. No. 18/906,489, mailed Jun. 5, 2025.

Sah et al.; "Recent Trends in Preparation of Poly(lactide-co-glycolide) Nanoparticles by Mixing Polymeric Organic Solution with Antisolvent," 2015; Hindawi Publishing Corporation; Journal of Nanomaterials, vol. 2015, Article ID 794601, pp. 1-22. (Year: 2015).

English Translation of CN Office Action Mailed on Aug. 3, 2022 for CN Application No. 202080012222.9, 4 pages.

(56) References Cited

OTHER PUBLICATIONS

Final Office Action for U.S. Appl. No. 18/906,489, mailed Sep. 4, 2025.

Gross-Rother et al., "Particle Detection and Characterization for Biopharmaceutical Applications: Current Principles of Established and Alternative Techniques", Pharmaceutics, vol. 12, No. 11, Nov. 19, 2020, 49 pages.

Jack et al., "Analysis of particulate contaminations of infusion solutions in a pediatric intensive care unit", Intensive Care Medicine, vol. 36, No. 4, Feb. 18, 2010, pp. 707-711.

Jones, A.J.S., "Analysis of Polypeptides and Proteins," Advanced Drug Delivery Reviews, vol. 10; p. 29-90 (1993).

Oxford Dictionary (2024, one page) (Year: 2024).

Zhiqi, L., et al., "Functional Emulsifiers and Emulsions", China Light Industry Press, Apr. 30, 2000, 2 pages. (Concise explanation met by English Translation of Search report attached).

* cited by examiner

Radiant Efficiency

[photons/s/cm$^2$/sr]/[μW/cm$^2$]

COMPOSITIONS AND METHODS FOR THE DELIVERY OF THERAPEUTIC BIOLOGICS FOR TREATMENT OF DISEASE

RELATED APPLICATIONS

This application is a continuation of U.S. application Ser. No. 17/351,963, filed Jun. 18, 2021, now U.S. Pat. No. 11,459,376, issued Oct. 4, 2022, which is a continuation of International Application No. PCT/US2020/050508, filed Sep. 11, 2020, published in English, which claims the benefit of U.S. Provisional Application No. 63/024,703, filed on May 14, 2020, U.S. Provisional Application No. 62/899,907, filed on Sep. 13, 2019, and U.S. Provisional Application No. 62/899,981, filed on Sep. 13, 2019. The entire teachings of the above applications are incorporated herein by reference.

GOVERNMENT SUPPORT

This invention was made with government support under Grant No. 1831212 awarded by the National Science Foundation. The government has certain rights in the invention.

TECHNICAL FIELD

The present disclosure relates to methods and compositions that enable the delivery (e.g., subcutaneous delivery) of biopharmaceutical products for therapy. In particular, the delivery method disclosed herein uses high concentration, low volume and low viscosity compositions of biologics that allow a practical transition from intravenous delivery to subcutaneous delivery of therapeutics, and permit a practical transition from frequent to less frequent subcutaneous delivery.

BACKGROUND

Biologics, particularly antibodies, have driven a paradigm shift in the course of drug discovery and development over the last few decades, assisting patients for whom few or no treatment options have previously existed. For example, current monoclonal antibody (mAb) therapies often require large doses which are administered by intravenous (IV) infusion at high-volume and low-concentration, which can take hours to deliver, causing patient discomfort and increasing the risk of infection. Subcutaneous (SC) injection provides a more desirable alternative for delivery since it decreases the burden on hospital and clinical facilities, requiring less time and lowers the risk of complications. However, SC injections require low delivery volumes which necessitate high therapeutic biologic concentrations that are often difficult to obtain. The requirement of high concentrations at low delivery volumes would also result in highly viscous injection solutions which could lead to excessively high injection forces. Moreover, a highly viscous injection solution of therapeutic biologic, e.g, mAb, would lead to increased protein-protein interactions resulting in product loss and also affects product safety. Therefore, a highly concentrated, low volume, low viscosity injection capability for SC delivery of therapeutic biopharmaceutical products is needed.

SUMMARY

Provided herein are methods useful for treating a disease or condition in a subject in need thereof, comprising administering to the subject a pharmaceutically effective amount of a composition comprising:

a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

In one aspect, the disclosure provides a method of treating cancer in a subject in need thereof, comprising administering to the subject a pharmaceutically effective amount of a composition comprising:

a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

The present disclosure also provides herein a method of treating an inflammatory disease or condition in a subject in need thereof, comprising administering to the subject a pharmaceutically effective amount of a composition comprising:

a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

In another aspect, the disclosure provides a method of treating immune disease in a subject in need thereof, comprising administering to the subject a pharmaceutically effective amount of a composition comprising:

a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

The present disclosure further provides herein a method of treating renal disease in a subject in need thereof, comprising administering to the subject a pharmaceutically effective amount of a composition comprising:

a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

In still another aspect, the disclosure provides a method of treating a skin disease or condition in a subject in need thereof, comprising administering to the subject a pharmaceutically effective amount of a composition comprising:

a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

In yet another aspect, the disclosure provides a pharmaceutically effective composition comprising:

a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

The present disclosure also provides herein a method of treating human immuno deficiency virus (HIV) infection in a subject in need thereof, comprising administering to the subject a pharmaceutically effective amount of a composition comprising:

a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

The present compositions and methods may be useful for treating a disease or condition in a subject in need thereof, comprising administering to the subject a pharmaceutically effective amount of a composition. In preferred embodiments, the treatment methods use a composition comprising: a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

DETAILED DESCRIPTION

Figure 1:
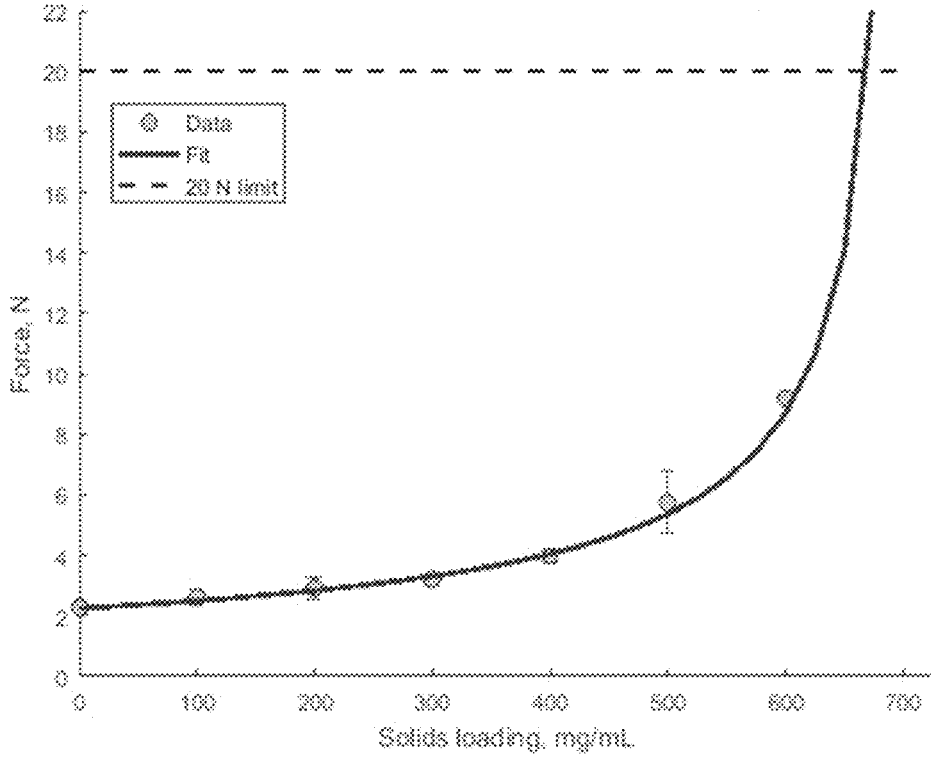
FIG. 1 shows a plot of syringe force versus solid concentrations using a 27-gauge ultra-thin wall (UTW) needle with a 4.7 mm inner diameter syringe barrel.

Therapeutic biologics, particularly monoclonal antibody (mAb) therapeutics have dramatically improved the treatment of human disease. However, the delivery of these biologics has been taxing on patients. The standard of administration is often by intravenous (IV) infusion at low concentrations, which can take hours to deliver, causing patient discomfort, and increasing the risk of infection for the patient. Although subcutaneous (SC) delivery by simple injection is preferred, constraints on SC delivery volume (1.5-2.0 mL) necessitate antibody concentrations greater than 100 mg/mL, which are often unfeasible. Solution concentrations exceeding 100 mg/mL are highly viscous, which lead to exceedingly high injection forces and often propagates decomposition of the therapeutic antibody compositions. The utilization of particle suspension technology can deliver therapeutic biologic (e.g., antibody) concentrations >500 mg/mL while preserving full structure and bioactivity of the therapeutic biologic (e.g., mAb). Thus, by transforming the delivery of therapeutic biologics from IV to SC can offer advantages to patients, healthcare providers, payers, and pharmaceutical developers. In some cases, the concentration of biologics in particle form can lead to less frequently delivered SC injections for biologics that are frequently SC injected.

The present disclosure generally relates to compositions and methods for treating (e.g., down-regulating, reversing, inhibiting progression, preventing) a disease or condition in a subject in need thereof, comprising administering to the subject a pharmaceutically effective amount of a composition comprising: a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic, or salt thereof, in the composition is about 20 mg/mL to about 700 mg/mL. See Example 17 herein for description of an example method for determining the concentration of the therapeutic biologic in a composition of the disclosure.

The present disclosure also relates to methods for treating cancer, inflammatory disease or conditions, immune disease, renal disease, skin disease or conditions, or human immuno deficiency virus (HIV) infection in a subject in need thereof, comprising administering to the subject a pharmaceutically effective amount of a composition comprising: a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL. In certain embodiments, the compositions and methods described herein further comprise a pharmaceutically effective amount of at least one hyaluronan degrading agent that can be administered simultaneously, sequentially or intermittently with the composition. In preferred embodiments, the hyaluronan degrading agent is a hyaluronidase.

It will be readily understood that the aspects and embodiments, as generally described herein, are exemplary. The following more detailed description of various aspects and embodiments are not intended to limit the scope of the present disclosure, but is merely representative of various aspects and embodiments. Moreover, the compositions and methods disclosed herein may be changed by those skilled in the art without departing from the scope of the present disclosure. Unless defined otherwise, all technical and scientific terms used herein have the same meaning as is commonly understood by one of skill in the art to which this disclosure belongs. All publications and patents referred to herein are incorporated by reference.

Therapeutic Biologics

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted. As used herein, the phrase "and/or" when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

A therapeutic biologic, also known as a biologic medical product, or biopharmaceutical, is any pharmaceutical drug product manufactured in, extracted from, or semisynthesized from biological sources. Therapeutic biologics can include a wide range of products such as vaccines, blood and blood components, allergenics, somatic cells, gene therapy, tissues, and recombinant therapeutic proteins. In some embodiments, the therapeutic biologics can be composed of sugars, proteins, or nucleic acids or complex combinations of these substances, or may be living entities such as cells and tissues. Biologics can be isolated from a variety of natural sources, e.g., a human, animal, or microorganism, and may be produced by biotechnology methods or other technologies known in the art. Gene-based and cellular biologics, for example, are often used to treat a variety of medical conditions for which no other treatments are available. In certain embodiments of the disclosure, the therapeutic biologic is an antibody. In preferred embodiments, the therapeutic biologic is a monoclonal antibody (mAb).

The terms "antibody" and "immunoglobulin" are used interchangeably in the broadest sense and covers, but is not limited to, monoclonal antibodies (including full length monoclonal antibodies), polyclonal antibodies, multispecific antibodies, e.g., bispecific antibodies, humanized antibodies, fully human antibodies, biparatopic antibodies, humanized camelid heavy chain antibodies, and non-human/human chimeric antibodies, regardless of how they are produced, i.e., using immunization, recombinant, synthetic methodologies. "Parental antibodies" are antibodies obtained by exposure of an immune system to an antigen prior to modification of the antibodies for an intended use, e.g., humanization of a non-human antibody for use as a human therapeutic antibody. Antibodies can be gamma globulin proteins that are found in blood, or other bodily fluids of vertebrates that function in the immune system to bind antigen, hence identifying and/or neutralizing foreign objects. Antibodies can be assigned to different classes or isotypes. There are five classes of immunoglobulins: IgA, IgD, IgE, IgG, and IgM, having heavy chains designated alpha, delta, epsilon, gamma, and mu, respectively. The gamma class is further divided into subclasses based on the differences in sequences and function, e.g., humans express the following subclasses: IgG1, IgG2, IgG3, IgG4, IgA1, and IgA2. The L chain from any vertebrate species can be assigned to one of two distinct types, e.g., kappa and lambda, based on the amino acid sequences of their constant domains.

The recognized immunoglobulin genes include the kappa, lambda, alpha, gamma, delta, epsilon and mu constant region genes, as well as the myriad immunoglobulin variable region genes. In some embodiments, light chains are classified as either kappa or lambda. In other embodiments, heavy chains are classified as gamma, mu, alpha, delta, or epsilon, which in turn define the immunoglobulin classes, IgG, IgM, IgA, IgD and IgE, respectively. In other embodiments of the disclosure, the antibody is a human antibody. In certain embodiments, the human antibody is an IgG antibody. In certain other embodiments, the IgG antibody is an IgG1 antibody. In preferred embodiments of the disclosure, the antibody is a monoclonal antibody.

An exemplary antibody (immunoglobulin) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light" chain, domain, region and component are used interchangeably, are abbreviated by "VL" or "$V_L$" and refer to the light chain of an antibody or antibody fragment. Similarly, terms "variable heavy" chain, domain, region and component are used interchangeably, are abbreviated by "VH" or "$V_H$" and refer to the heavy chain of an antibody or antibody fragment. Antibodies are generally a heterotetrameric glycoprotein composed of two identical light (L) chains and two identical heavy (H) chains. Each L chain is linked to a H chain by one covalent disulfide bond. The two H chains are linked to each other by one or more disulfide bonds depending on the H chain isotype. Each H and L chain also has regularly spaced intra-chain disulfide bridges. H and L chains define specific Ig domains. In particular, each H chain has at the N-terminus, a variable domain (VH) followed by three constant domains (CH) for each of the alpha and gamma chains and four CH domains for p and c isotypes. Each L chain has at the N-terminus, a variable domain (VL) followed by a constant domain (CL) at its other end. The VL is aligned with the VH and the CL is aligned with the first constant domain of the heavy chain (CHL). The constant domain includes the Fc portion which comprises the carboxy-terminal portions of both H chains held together by disulfides. The effector functions of antibodies such as ADCC are determined by sequences in the Fc region, which is also the part recognized by Fc receptors (FcR) found on certain types of cells.

As disclosed herein, the pairing of a VH and VL together form a "variable region" or "variable domain" including the amino-terminal domains of the heavy or light chain of the antibody. The variable domain of the heavy chain may be referred to as "VH". The variable domain of the light chain may be referred to as "VL". The variable domain contains an "antigen binding site" which affects antigen binding and defines specificity of a particular antibody for its particular antigen. Variable regions span about 110 amino acid residues and consist of relatively invariant stretches called framework regions (FRs) (generally about 4) of 15-30 amino acids separated by shorter regions of extreme variability called "hypervariable regions" (generally about 3) that are each generally 9-12 amino acids long. The FRs largely adopt a p-sheet configuration and the hypervariable regions form loops connecting, and in some cases forming part of, the p-sheet structure. In certain embodiments, the "hypervariable region" refers to the regions of an antibody variable domain which are hypervariable in sequence and/or form structurally defined loops. Generally, antibodies comprise six hypervariable regions; three in the VH (H1, H2, H3), and three in the VL (L1, L2, L3). "Framework" or "FR" residues are those variable domain residues other than the hypervariable region residues defined herein.

The terms "full length antibody", "intact antibody" and "whole antibody" are used herein interchangeably, to refer to an antibody in its substantially intact form, not as antibody fragments as defined above. The terms particularly refer to an antibody with heavy chains that contain the Fc region. A full length antibody can be a native sequence antibody or an antibody variant. In certain embodiments, an "intact" or "whole" antibody is one which comprises an antigen-binding site as well as a CL and at least heavy chain constant domains, CH1, CH2 and CH3. The constant domains may be native sequence constant domains, e.g. human native sequence constant domains, or amino acid sequence variants thereof.

As indicated above, the term antibody as used herein, unless otherwise stated or clearly contradicted by context, includes fragments of an antibody that retain the ability to specifically interact, such as bind, to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the light chain variable domain (VL), heavy chain variable domain (VH), light chain constant region (CL) and heavy chain constant region domain 1 (CH1) domains, or a monovalent antibody as described in WO 2007/059782; (ii) F(ab')₂ fragments, bivalent fragments comprising two Fab fragments linked by a disulfide bridge at the hinge region; (iii) an Fd fragment consisting essentially of the VH and CH1 domains; (iv) an Fv fragment consisting essentially of the VL and VH domains of a single arm of an antibody, (v) a dAb fragment Ward et al., Nature 341, 544-546 (1989), which consists essentially of a VH domain and is also called domain antibody Holt et al; Trends Biotechnol. 2003 November; 21(11):484-90; (vi) camelid or nanobodies Revets et al; Expert Opin Biol Ther. 2005 January; 5(1):111-24 and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Revets et al; Expert Opin Biol Ther. 2005 January; 5(1):111-24 and Bird et al., Science 242, 423-426 (1988). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein.

As disclosed herein, "whole antibody fragments including a variable domain" include Fab, Fab', F(ab')₂, and Fv fragments; diabodies; linear antibodies, single-chain antibody molecules; and multispecific antibodies formed from antibody fragments. The "Fab fragment" consists of an entire L chain along with the variable region domain of the H chain, and the first constant domain of one heavy chain (CHI). Each Fab fragment is monovalent with respect to antigen binding, i.e., it has a single antigen-binding site. A "Fab' fragment" differs from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. A "F(ab')₂ fragment" roughly corresponds to two disulfide linked Fab fragments having divalent antigen-binding activity and is still capable of cross-linking antigen. An "Fv" is the minimum antibody fragment which contains a complete antigen-recognition and binding site. This fragment consists of a dimer of one heavy and one light chain variable region domain in tight, non-covalent association. In a single-chain Fv (scFv) species, one heavy and one light chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. "Single-chain Fv" also abbreviated as "sFv" or "scFv" are antibody fragments that comprise the VH and VL antibody domains connected to form a single polypeptide chain. In preferred embodiments, the scFv polypeptide further comprises a polypeptide linker between the VH and VL domains which enables the scFv to form the desired structure for antigen binding. In some embodiments, a "single variable domain" is half of an Fv (comprising only three CDRs specific for an antigen) that has the ability to recognize and bind antigen, although at a lower affinity than the entire binding site.

In some embodiments, "diabodies" refer to antibody fragments with two antigen-binding sites, which fragments comprise a heavy-chain variable domain (VH) connected to a light-chain variable domain (VL) in the same polypeptide chain (VH-VL). The small antibody fragments are prepared by constructing sFv fragments with short linkers (about 5-10 residues) between the VH and VL domains such that inter-chain but not intra-chain pairing of the variable domains is achieved, resulting in a bivalent fragment, i.e., fragment having two antigen-binding sites. In other embodiments, diabodies may be bivalent or bispecific. In certain embodiments, bispecific diabodies are heterodimers of two "crossover" sFv fragments in which the VH and VL domains of the two antibodies are present on different polypeptide chains. Triabodies and tetrabodies are also generally known in the art.

"Antibody fragments" or "Antigen binding fragments" of antibodies as described herein, comprise only a portion of an intact antibody, generally including an antigen binding site of the intact antibody and thus retaining the ability to bind antigen. Exemplary examples of antibody fragments encompassed by the present disclosure include, but are not limited to: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) isolated CDR regions; (viii) F(ab')2 fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd, segments (VH-CH1-VH-CH1) which, together with complementary light chain polypeptides, form a pair of antigen binding regions. In some embodiments, an "antigen binding site" generally refers to a molecule that includes at least the hypervariable and framework regions that are required for imparting antigen binding function to a V domain. An antigen binding site may be in the form of an antibody or an antibody fragment, (such as a dAb, Fab, Fd, Fv, F(ab')$_2$ or scFv) in a method described herein. In certain embodiments, the therapeutic biologic is an antibody fragment.

In some embodiments, the term "single-chain Fv" or "scFv" or "single chain" antibody can refer to antibody fragments comprising the VH and VL domains of antibody, wherein these domains are present in a single polypeptide chain. Generally, the Fv polypeptide further comprises a polypeptide linker between the VH and VL domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

As used herein, the term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies (mAbs) are highly specific, being directed against a single antigenic site or determinant on the antigen. In addition to their specificity, the monoclonal antibodies are advantageous in that they may be synthesized uncontaminated by other antibodies. Monoclonal antibodies may be prepared by the hybridoma methodology. The monoclonal antibodies may also be isolated from phage antibody libraries using molecular engineering techniques. The monoclonal antibodies of the disclosure may be generated by recombinant DNA methods, and are sometimes referred to as "recombinant antibodies" or "recombinant monoclonal antibodies" as disclosed herein. In some embodiments, a monoclonal antibody is a single species of antibody wherein every antibody molecule recognizes the same epitope because all antibody producing cells are derived from a single B-lymphocyte cell line. The methods for generating monoclonal antibodies (mAbs) generally begin along the same lines as those for preparing polyclonal antibodies. In other embodiments, rodents such as mice and rats are used in generating monoclonal antibodies. In certain embodiments, rabbit, sheep, or frog cells are used in generating monoclonal antibodies. The use of rats is known and may provide certain advantages. Mice, e.g., BALB/c mice, are routinely used and generally give a high percentage of stable fusions. In still other embodiments of the disclosure, the antibody is a monoclonal antibody. In certain embodiments of the disclosure, the antibody is a human monoclonal antibody. In preferred embodiments, the IgG antibody is human monoclonal antibody.

In other embodiments, recombinant antibody fragments may be isolated from phage antibody libraries using techniques known in the art. See, for example, Clackson et al., 1991, Nature 352: 624-628; Marks et al., 1991, J. Mol. Biol. 222: 581-597. Recombinant antibody fragments may be derived from large phage antibody libraries generated by recombination in bacteria (Sblattero and Bradbury, 2000, Nature Biotechnology 18:75-80; and as described herein). Polynucleotides encoding the VH and VL components of antibody fragments (i.e., scFv) may be used to generate recombinant full length immunoglobulins using methods known in the art (see, for example, Persic et al., 1997, Gene 187: 9-18).

An "isolated antibody" is one that has been identified and separated and/or recovered from a component of its pre-existing environment. Contaminant components are materials that would interfere with therapeutic uses for the antibody, and may include enzymes, hormones, and other proteinaceous or nonproteinaceous solutes.

As used herein, a "human antibody" refers to an antibody that possesses an amino acid sequence that corresponds to that of an antibody produced by a human. Human antibodies can be produced using various techniques known in the art, including phage-display libraries. Human antibodies can be prepared by administering the antigen to a transgenic animal that has been modified to produce such antibodies in response to antigenic challenge, but whose endogenous loci has been disabled. "Humanized" forms of non-human, e.g., rodent, antibodies are chimeric antibodies that contain minimal sequence derived from the non-human antibody. As used herein, a "chimeric antibody" is an antibody having the variable domain from a first antibody and the constant domain from a second antibody wherein (i) the first and second antibodies are from different species (Morrison et al., (1984) Proc. Natl. Acad. Sci. USA 81: 6851-6855) or (ii) the first and second antibodies are from different isotypes, e.g., variable domain from an IgG1 antibody and the constant domains from an IgG4 antibody). In some embodiments, the variable domains are obtained from a non-human antibody such as a mouse antibody (the "parental antibody"), and the constant domain sequences are obtained from a human antibody. In other embodiments, the variable domains are humanized variable domains from a mouse antibody and the constant domains of a human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

An "affinity matured" antibody is one with one or more alterations in one or more hypervariable region thereof that result in an improvement in the affinity of the antibody for antigen, compared to a parent antibody that does not possess those alterations. In some embodiments, affinity matured antibodies can have micromolar affinities for the target antigen. In other embodiments, affinity matured antibodies can have nanomolar or even picomolar affinities for the target antigen. Affinity matured antibodies are produced by procedures known in the art.

A "blocking" antibody or an "antagonist" antibody is one that inhibits or reduces biological activity of the antigen it binds. In some embodiments, blocking antibodies or antagonist antibodies substantially or completely inhibit the biological activity of the antigen. An "agonist antibody", as used herein, is an antibody, which mimics at least one of the functional activities of a polypeptide of interest. As used herein, the term "inhibition", "inhibit", "inhibiting" and the like in reference to a protein-inhibitor, e.g. antagonist, interaction means negatively affecting, e.g. decreasing, the activity or function of the protein relative to the activity or function of the protein in the absence of the inhibitor. In some embodiments, inhibition refers to reduction of a disease or the symptoms of disease. In other embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

"Binding affinity" generally refers to the strength of the sum total of noncovalent interactions between a single binding site of a molecule, e.g., an antibody, and its binding partner, e.g., an antigen. Unless indicated otherwise, as used herein, "binding affinity" refers to intrinsic binding affinity, which reflects a 1:1 interaction between members of a binding pair, e.g., antibody and antigen. The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. "Epitope" generally refers to that part of an antigen that is bound by the antigen binding site of an antibody. In some embodiments, an epitope may be "linear" in the sense that the hypervariable loops of the antibody CDRs that form the antigen binding site bind to a sequence of amino acids as in a primary protein structure. In other embodiments, the epitope is a "conformational epitope", i.e. one in which the hypervariable loops of the CDRs bind to residues as they are presented in the tertiary or quaternary protein structure.

In some embodiments of the foregoing compositions and methods, the therapeutic biologic is an antibody. In other embodiments, the antibody includes but are not limited to 3F8, Abagovomab, Abatacept, Abciximab, Abituzumab, Abrezekimab, Abrilumab, Acritumomab, Actoxumab, Abituzumab, Adalimumab-adbm, Adalimumab-atto, Adalimumab-bwwb, Adecatumumab, Ado-trastuzumab emtansine, Aducanumab, Afasevikumab, Afelimomab, Aflibercept, Afutuzumab, Alacizumab pegol, ALD518, Alefacept, Alemtuzumab, Alirocumab, Altumomab pentetate, Amatuximab, Anatumomab mafenatox, Andecaliximab, Anetumab ravtansine, Anifrolumab, Anrukinzumab, Apolizumab, Aprutumab ixadotin, Arcitumomab, Ascrinvacumab, Aselizumab, Atezolizumab, Atidortoxumab, Atinumab, Atlizumab, Atorolimumab, Avelumab, Azintuxizumab vedotin, Bapineuzumab, Basiliximab, Bavituximab, BCD-100, Bectumomab, Begelomab, Belantamab mafodotin, Belatacept, Belimumab, Bemarituzumab, Benralizumab, Bermekimab, Bersanlimab, Bertilimumab, Besilesomab, Bevacizumab, Bevacizumab-awwb, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, CR6261, Crizanlizumab, Crotedumab, Cusatuzumab, Dacetuzumab, Daclizumab, Dalotuzumab, Dapirolizumab pegol, Daratumumab, Dectrekumab, Demcizumab, Denileukin diftitox, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlimab, Drozitumab, DS-8201, Duligotumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epoetin-alfa, Epoetin-alfa-epbx, Epratuzumab, Eptinezumab, Erenumab, Erlizumab, Ertumaxomab, Etanercept, Etanercept-szzs, Etaracizumab, Etigilimab, Etrolizumab, Evinacumab, Evolocumab, Exbivirumab, Factor VIII Fc fusion protein, Factor IX Fc fusion protein, Fanolesomab, Faralimomab, Faricimab, Farletuzumab, Fasinumab, Felvizumab, Fezakinumab, Fibatuzumab, Ficlatuzumab, Figitumumab, Filgrastim, Filgrastim-sndz, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ibalizumab, IBI308, Ibritumomab tiuxetan, Icrucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Infliximab-abda, Infliximab-dyyb, Infliximab-qbtx, Intetumumab, Inolimomab, Inotuzumab ozogamicin, Ipilimumab, Iomab-B, Iratumumab, Isatuximab, Iscalimab, Istiratumab, Itolizumab, Ixekizumab, Keliximab, Labetuzumab, Lacnotuzumab, Ladiratuzumab vedotin, Lambrolizumab, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Loncastuximab tesirine, Losatuxizumab vedotin, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Lupartumab amadotin, Lutikizumab, Mapatumumab, Margetuximab, Marstacimab, Maslimomab, Mavrilimumab, Matuzumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pegfilgrastim-jmdb, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Raxibacumab, Ravagalimab, Ravulizumab, Refanezumab, Regavirumab, Relatlimab, Remtolumab, Reslizumab, Rilonacept, Rilotumumab, Rinucumab, Risankizumab, Rituximab, Rituximab-abbs, Rituximab-pvvr, Rivabazumab pegol, Rivabazumab pegol, Robatumumab, Rmab, Roledumab, Romilkimab, Romiplostim, Romosozumab, Rontalizumab, Rosmantuzumab, Rovalpituzumab tesirine, Rovalpituzumab tesirine, Rovelizumab, Rozanolixizumab, Ruplizumab, Sacituzumab govitecan, Samalizumab, Samrotamab vedotin, Sapelizumab, Sarilumab, Satralizumab (SA237), Satumomab pendetide, Secukinumab, Selicrelumab, Seribantumab, Setoxaximab, Setrusumab, Sevirumab, Sibrotuzumab, SGN-CD19A, SGN-CD33A, SHP647, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Ticilimumab, Tildrakizumab, Tigatuzumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab, Tovetumab, Tralokinumab, Trastuzumab, Trastuzumab-anns, Trastuzumab-dkst, Trastuzumab-dttb, Trastuzumab emtansine, Trastuzumab-pkrb, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Xentuzumab, XMAB-5574, Zalutumumab, Zanolimumab, Zatuximab, Zenocutuzumab, Ziralimumab, Zolbetuximab (IMAB362, Claudiximab), Ziv-aflibercept, or Zolimomab aritox.

In other embodiments of the foregoing compositions and methods, the antibody is monoclonal. In certain embodiments, the monoclonal antibody includes but are not limited to 3F8, 8H9, Abatacept, Abagovomab, Abciximab, Abituzumab, Adalimumab-adbm, Adalimumab-atto, Adalimumab-bwwb, Abrilumab, Actoxumab, Abituzumab, Abrezekimab, Abrilumab, Actoxumab, Adalimumab, Adecatumumab, Ado-trastuzumab emtansine, Aducanumab, Afasevikumab, Afelimomab, Aflibercept, Afutuzumab, Alacizumab pegol, ALD518, Alefacept, Alemtuzumab, Alirocumab, Altumomab pentetate, Amatuximab, Anatumomab mafenatox, Andecaliximab, Anetumab ravtansine, Anifrolumab, Anrukinzumab (IMA-638) Apolizumab, Arcitumomab, Ascrinvacumab, Aselizumab, Atezolizumab, Atidortoxumab, Atinumab, Atlizumab (tocilizumab), Atorolimumab, Avelumab, Bapineuzumab, Basiliximab, Bevacizumab, Bevacizumab-awwb, BCD-100, Bectumomab, Begelomab, Belatacept, Belimumab, Bemarituzumab, Benralizumab, Bermekimab, Bersanlimab, Bertilimumab, Besilesomab, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camrelizumab, Canakinumab, Cantuzumab mertansine, Cantuzumab ravtansine, Caplacizumab, Capromab pendetide, Carlumab, Carotuximab, Catumaxomab, Cedelizumab, Cemiplimab, Certolizumab pegol, Cetrelimab, Cetuximab, Cibisatamab, Cirmtuzumab, Ch. 14.18, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, CR6261, Crizanlizumab, Crotedumab, Cusatuzumab, Dacetuzumab, Daclizumab, Dalotuzumab, Dapirolizumab pegol, Daratumumab, Dectrekumab, Demcizumab, Denileukin diftitox, Denintuzumab mafodotin, Denosumab, Derlotuximab biotin, Detumomab, Dezamizumab, Dinutuximab, Diridavumab, Domagrozumab, Dorlimomab aritox, Dostarlimab, Drozitumab, Duligotumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emibetuzumab, Emicizumab, Enavatuzumab, Enfortumab vedotin,

15

Enlimomab pegol, Enoblituzumab, Enokizumab, Enoti-cumab, Ensituximab, Epitumomab cituxetan, Epoetin-alfa, Epoetin-alfa-epbx, Epratuzumab, Eptinezumab, Erenumab, Erlizumab, Ertumaxomab, Etanercept, Etanercept-szzs, Eta-racizumab, Etigilimab, Etrolizumab, Evinacumab, Evo-locumab, Exbivirumab, Factor VIII Fc fusion protein, Factor IX Fc fusion protein, Fanolesomab, Faralimomab, Farici-mab, Farletuzumab, Fasinumab, FBTA05, Felvizumab, Fezakinumab, Fibatuzumab, Ficlatuzumab, Figitumumab, Filgrastim, Filgrastim-sndz, Firivumab, Flanvotumab, Fle-tikumab, Flotetuzumab, Fontolizumab, Foralumab, Fora-virumab, Fremanezumab, Fresolimumab, Frovocimab, Fru-nevetmab, Fulranumab, Futuximab, Galcanezumab, Galiximab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gos-uranemab, Guselkumab, Ibalizumab, IBI308, Ibritumomab tiuxetan, Icrucumab, Idarucizumab, Ifabotuzumab, Igov-omab, IMAB362, Imalumab, Imaprelimab, Imciromab, Imgatuzumab, Inclacumab, Indatuximab ravtansine, Indusa-tumab vedotin, Inebilizumab, Infliximab, Infliximab-abda, Infliximab-dyyb, Infliximab-qbtx, Intetumumab, Inolimo-mab, Inotuzumab ozogamicin, Ipilimumab, Iratumumab, Isatuximab, Iscalimab, Istiratumab, Itolizumab, Ixekizumab, Keliximab, Labetuzumab, Lacnotuzumab, Lambrolizumab, Lampalizumab, Lanadelumab, Landogrozumab, Larcavix-imab, Lebrikizumab, Lemalesomab, Lendalizumab, Lenver-vimab, Lenzilumab, Lerdelimumab, Leronlimab, Lesofa-vumab, Letolizumab, Lexatumumab, Libivirumab, Lifastuzumab vedotin, Ligelizumab, Lilotomab satet-raxetan, Lintuzumab, Lirilumab, Lodelcizumab, Lokiv-etmab, Lorvotuzumab mertansine, Lucatumumab, Luli-zumab pegol, Lumiliximab, Lumretuzumab, Lutikizumab, Mapatumumab, Margetuximab, Marstacimab, Maslimo-mab, Mavrilimumab, Matuzumab, Mepolizumab, Metelim-umab, Milatuzumab, Minretumomab, Mirikizumab, Mir-vetuximab soravtansine, Mitumomab, Modotuximab, Mogamulizumab, Monalizumab, Morolimumab, Mosu-netuzumab, Motavizumab, Moxetumomab pasudotox, Muromonab-CD3, Nacolomab tafenatox, Namilumab, Nap-tumomab estafenatox, Narnatumab, Natalizumab, Navicixi-zumab, Navivumab, Naxitamab, Nebacumab, Necitu-mumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onar-tuzumab, Ontuxizumab, Onvatilimab, Opicinumab, Opor-tuzumab monatox, Oregovomab, Orticumab, Otelixizumab, Otilimab, Otlertuzumab, Oxelumab, Ozanezumab, Pagibax-imab, Palivizumab, Pamrevlumab, Panitumumab, Pankomab, Panobacumab, Parsatuzumab, Pascolizumab, Pasotuxizumab, Pateclizumab, Patritumab, PDR001, Pegfil-grastim-jmdb, Pembrolizumab, Pemtumomab, Peraki-zumab, Pertuzumab, Pexelizumab, Pidilizumab, Pinatuzumab vedotin, Pintumomab, Placulumab, Plozali-zumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Tetulo-mab, Racotumomab, Radretumab, Rafivirumab, Ralpanci-zumab, Ramucirumab, Ranevetmab, Ranibizumab, Raxi-bacumab, Ravagalimab, Ravulizumab, Refanezumab, Regavirumab, Relatlimab, Remtolumab, Reslizumab, Rilonacept, Rilotumumab, Rinucumab, Risankizumab-rzaa, Rituximab, Rituximab-abbs, Rituximab-pvvr, Robatumumab, Rmab, Roledumab, Romilkimab, Romiplostim, Romosozumab, Rontalizumab, Rosmantuzumab, Roveli-zumab, Rozanolixizumab, Ruplizumab, Sacituzumab govitecan, Samalizumab, Sarilumab, Satralizumab (SA237), Satumomab pendetide, Secukinumab, Selicrelumab, Serib-antumab, Setoxaximab, Setrusumab, Sevirumab, Sibro-tuzumab, SGN-CD19A, SGN-CD33A, SHP647, Sifalim-umab, Siltuximab, Simtuzumab, Siplizumab, Sirukumab, Sofituzumab vedotin, Solanezumab, Solitomab, Sonepci-zumab, Sontuzumab, Spartalizumab, Stamulumab, Suleso-mab, Suptavumab, Sutimlimab, Suvizumab, Suvratoxumab, Tabalumab, Tacatuzumab tetraxetan, Tadocizumab, Tala-cotuzumab, Talizumab, Tamtuvetmab, Tanezumab, Taplitu-momab paptox, Tarextumab, Tavolimab, Tefibazumab, Teli-momab aritox, Tenatumomab, Teneliximab, Teplizumab, Tepoditamab, Teprotumumab, Tesidolumab, Tetulomab (lilotomab), Tezepelumab, TGN1412, Tibulizumab, Ticili-mumab (tremelimumab), Tildrakizumab, Tigatuzumab, Timigutuzumab, Timolumab, Tiragotumab, Tislelizumab, TNX-650, Tocilizumab (atlizumab), Tomuzotuximab, Toralizumab, Tosatoxumab, Tositumomab, Tovetumab, Tralokinumab, Trastuzumab, Trastuzumab-anns, Trastuzumab-dkst, Trastuzumab-dttb, Trastuzumab emtansine, Trastuzumab-pkrb, TRB S07, Tregalizumab, Tremelimumab, Trevogrumab, Tucotuzumab celmoleukin, Tuvirumab, Ublituximab, Ulocuplumab, Urelumab, Urtoxa-zumab, Ustekinumab, Utomilumab, Vanalimab, Vandor-tuzumab vedotin, Vantictumab, Vanucizumab, Vapaliximab, Varisacumab, Varlilumab, Vatelizumab, Vedolizumab, Vel-tuzumab, Vepalimomab, Vesencumab, Visilizumab, Vobarilizumab, Volociximab, Vonlerolizumab, Voprate-limab, Vorsetuzumab mafodotin, Votumumab, Xentuzumab, XMAB-5574, Zalutumumab, Zanolimumab, Zatuximab, Zenocutuzumab, Ziralimumab, Zolbetuximab (IMAB362, Claudiximab), Ziv-aflibercept, Zolimomab aritox or the cor-responding anti-drug antibody in a sample from a human patient. In preferred embodiments, the monoclonal antibody is Rituximab, Rituximab-abbs, or Rituximab-pvvr.

In some embodiments, the monoclonal antibody is a biosimilar. In other embodiments, the biosimilar includes but are not limited to Adalimumab-adbm, Adalimumab-atto, Adalimumab-bwwb, Bevacizumab-awwb, Epoetin alfa-epbx, Etanercept-szzs, Infliximab-abda, Infliximab-dyyb, Infliximab-qbtx, Filgrastim-sndz, Pegfilgrastim-jmdb, Peg-filgrastim-bmez, Risankizumab-rzaa, Rituximab-abbs, Rit-uximab-pvvr, Trastuzumab-anns, Trastuzumab-dttb, Trastuzumab-pkrb, or Trastuzumab-dkst. In certain embodi-ments, the active biosimilar substance is Adalimumab, Bevacizumab, Enoxaparin sodium, Epoetin alfa, Epoetin zeta, Etanercept, Filgrastim, Follitropin alfa, Infliximab, Insulin glargine, Insulin lispro, Pegfilgrastim, Risanki-zumab, Rituximab, Rituximab-abbs, Rituximab-pvvr, Somatropin, Teriparatide, or Trastuzumab. In preferred embodiments, the biosimilar is Rituximab, Rituximab-abbs, or Rituximab-pvvr.

In other embodiments, the targeting moiety is an antibody from an intact polyclonal antibody, an intact monoclonal antibody, an antibody fragment, a single chain Fv (scFv) mutant, a multispecific antibody, a bispecific antibody, a chimeric antibody, a humanized antibody, a human antibody, a fusion protein comprising an antigenic determinant portion of an antibody, or other modified immunoglobulin mol-ecules comprising antigen recognition sites.

Provided herein are compositions and methods for treat-ing cancer in a subject in need thereof, comprising admin-istering to the subject a pharmaceutically effective amount of a composition comprising: a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL. In certain embodiments, provided herein, are methods for treating non-Hodgkin's lymphoma (NHL) in a subject in need thereof, comprising administering to the subject a pharmaceutically effective amount of a composition comprising: a plurality of particles suspended in a low viscosity pharmaceutically acceptable liquid carrier, each particle comprising rituximab; wherein the particles have less than about 10% aggregation of the therapeutic biologic or salt thereof; and the concentration of the therapeutic biologic or salt thereof in the composition is about 20 mg/mL to about 700 mg/mL.

The term "treat" or "treating" or "treatment" generally refers to both therapeutic treatment and prophylactic or preventative measures, e.g., treating, preventing, reversing and/or down-regulating a disease or condition. As used herein, "treat" or "treating" means to administer a therapeutic biologic, such as a composition containing any of the antibodies or antigen binding fragments thereof of the present disclosure, internally or externally to a subject having one or more disease symptoms, or being suspected of having a disease, for which the biologic has therapeutic activity or prophylactic activity. Typically, the therapeutic biologic is administered in an amount effective to alleviate one or more disease symptoms in the treated subject or population, whether by inducing the regression of or inhibiting the progression of such symptom(s) by any clinically measurable degree. The amount of a therapeutic biologic that is effective to alleviate any particular disease symptom may vary according to factors such as the disease state, age, and weight of the subject or patient, and the ability of the therapeutic biologic to elicit a desired response in the subject or patient. Whether a disease symptom has been alleviated can be assessed by any clinical measurement typically used by physicians or other skilled healthcare providers to assess the severity or progression status of the symptom. The term further includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a human or animal subject with a disorder, disease or symptom, or with the potential to develop such a disorder, disease or symptom. As used herein, "treatment," as it applies to a human or veterinary subject, refers to therapeutic treatment, as well as diagnostic applications. "Treatment" as it applies to a human or veterinary subject, encompasses contact of the therapeutic biologic, e.g., antibodies or antigen binding fragments of the present disclosure to a human or animal subject. Subjects requiring treatment for cancer include those already having a benign, pre-cancerous, or non-metastatic tumor as well as those in which the occurrence or recurrence of cancer is to be prevented. In some embodiments, the objective or outcome of treating or treatment may be to reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. In some embodiments, the efficacy of treatment can be measured by assessing the duration of survival, time to disease progression, the response rates (RR), duration of response, and/or quality of life. The concentration of the therapeutic biologic in the composition is typically of about 20 mg/mL to about 700 mg/mL, e.g., about 20, 30, 50, 75, 100, 125, 150, 175, 200, 225, 250, 275, 300, 325, 350, 375, 400, 425, 450, 475, 500, 525, 550, 575, 600, 625, 650, 675 mg/mL to about 700 mg/mL. The therapeutic biologic in the composition may have about 0.5 to about 1.0 activity per unit, about 0.75 to about 1.0 activity per unit, or about 0.9 to about 1.0 activity per unit. Activity is measured relative to the same therapeutic biologic prior to particle formation. In preferred embodiments, the therapeutic biologic has an activity per unit of about 0.5 to about 1.0. The term "prevent" or "preventing" or "prevention" as used herein refers to any action that inhibits or delays the onset of a disease or condition in a subject in need thereof, comprising administering to the subject a pharmaceutically effective amount of a composition according to the present disclosure. In certain embodiments of the disclosure, "treating" a subject afflicted with a disease or condition shall include, without limitation, (i) slowing, stopping or reversing the progression of the disease or condition, (ii) slowing, stopping or reversing the progression of the symptoms of the disease or condition, (iii) reducing the likelihood of the recurrence of the disease or condition, and/or (iv) reducing the likelihood that the symptoms of the disease or condition will recur.

"Pre-cancerous" or "pre-neoplasia" generally refers to a condition or a growth that typically precedes or develops into a cancer. A "pre-cancerous" growth may have cells that are characterized by abnormal cell cycle regulation, proliferation, or differentiation, which can be determined by markers of cell cycle.

Examples of cancer include but are not limited to blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, leukemia or lymphoid malignancies, lung cancer including small-cell lung cancer (SGLG), non-small cell lung cancer (NSGLG), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

In some embodiments, "a condition or symptom associated with" may be any pathology that arises as a consequence of, preceding, or proceeding from the cancer. For example, where the cancer is a skin cancer, the condition or relevant symptom may be microbial infection. Where the cancer is a secondary tumor, the condition or symptom may relate to organ dysfunction of the relevant organ having tumor metastases. In other embodiments, the methods of treating described herein are for the minimization or treatment of a condition or symptom in an individual that is associated with a cancer in the individual. In certain embodiments, the subject is a mammal. In preferred embodiments, the subject is human.

Non-limiting examples of cancer which can be treated by the compositions and methods described herein, include but are not limited to any solid or non-solid cancer and/or cancer metastasis, including, but is not limiting to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B-cell, Burkitt, cutaneous T cell, histiocytic, lymphoblastic, T cell, thymic, B-cell non-Hodgkin lymphoma), gliomas, adenocarcinoma, adrenal tumor, hereditary adrenocortical carcinoma, brain malignancy (tumor), various other carcinomas (e.g., bronchogenic large cell, ductal, malignant ascites, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B-cell), hypernephroma, insulinoma, islet tumor, keratoma, leiomyoblastoma, leiomyosarcoma, leukemia (e.g., acute lymphatic, acute lymphoblastic, acute lymphoblastic pre-B-cell, acute lymphoblastic T cell leukemia, acute-megakaryoblastic, monocytic, acute myelogenous, acute myeloid, acute myeloid with eosinophilia, B-cell, basophilic, chronic myeloid, chronic, B-cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B-cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), osteoporosis, bone metastasis, papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, or Turcot syndrome with glioblastoma.

According to some embodiments of the disclosure, the compositions and methods described herein, further comprises an anti-cancer agent suitable for a treatment, include but are not limited to chemotherapy, biological therapy, photodynamic therapy, nutritional therapy, brachiotherapy, immunotherapy, or cellular therapy. In some embodiments, the anti-cancer agent may kill cancer cells (cytotoxic agent). In other embodiments, the anti-cancer agent may prevent cancer cells from multiplying (cytostatic agent).

In some embodiments, the compositions and methods described herein, further comprises at least one pharmaceutically acceptable cytotoxic or cytostatic agent. In other embodiments, the cytotoxic or cytostatic agent includes but are not limited to Abiraterone Acetate, Abitrexate (Methotrexate), Adriamycin (Doxorubicin Hydrochloride), Adrucil (Fluorouracil), Afatinib Dimaleate, Afinitor (Everolimus), Aldesleukin, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Asparaginase *Erwinia chrysanthemi*, Axitinib, Azacitidine, Becenum (Carmustine), Beleodaq (Belinostat), Belinostat, Bendamustine Hydrochloride, Bexarotene, Bicalutamide, BiCNU (Carmustine), Bleomycin, Bortezomib, Bosulif (Bosutinib), Bosutinib, Busulfan, Busulfex (Busulfan), Cabazitaxel, Cabozantinib-S-Malate, Camptosar (Irinotecan Hydrochloride), Capecitabine, Carboplatin, CARBOPLATIN-TAXOL, Carfilzomib, Carmubris (Carmustine), Carmustine, Casodex (Bicalutamide), CeeNU (Lomustine), Ceritinib, Cerubidine (Daunorubicin Hydrochloride), Chlorambucil, CHLORAMBUCIL-PREDNISONE, Cisplatin, Clafen (Cyclophosphamide), Clofarabine, Clofarex (Clofarabine), Clolar (Clofarabine), Cometriq (Cabozantinib-S-Malate), Cosmegen (Dactinomycin), Crizotinib, Cyclophosphamide, Cyfos (Ifosfamide), Cytarabine, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Dexrazoxane Hydrochloride, Docetaxel, Doxorubicin Hydrochloride, DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Everolimus, Evista (Raloxifene Hydrochloride), Exemestane, Fareston (Toremifene), Farydak (Panobinostat), Faslodex (Fulvestrant), Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRINOX, FOLFOX, Folotyn (Pralatrexate), Fulvestrant, Gefitinib, Gemcitabine Hydrochloride, GEMCITABINE-CISPLATIN, GEMCITABINE-OXALIPLATIN, Gemzar (Gemcitabine Hydrochloride), Gilotrif (Afatinib Dimaleate), Gleevec (Imatinib Mesylate), Gliadel (Carmustine Implant), Glucarpidase, Goserelin Acetate, Halaven (Eribulin Mesylate), Hycamtin (Topotecan Hydrochloride), Ibrance (Palbociclib), Ibrutinib, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Inlyta (Axitinib), Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Keoxifene (Raloxifene Hydrochloride), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), Lomustine, Lupron (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), Mozobil (Plerixafor), Mustargen (Mechlorethamine Hydrochloride), Mutamycin (Mitomycin C), Myleran (Busulfan), Mylosar (Azacitidine), Navelbine (Vinorelbine Tartrate), Nelarabine, Neosar (Cyclophosphamide), Nexavar (Sorafenib Tosylate), Nilotinib, Nolvadex (Tamoxifen Citrate), Nplate (Romiplostim), Olaparib, Omacetaxine Mepesuccinate, Ontak (Denileukin Diftitox), Oxaliplatin, Paclitaxel, Palbociclib, Palonosetron Hydrochloride, Pamidronate Disodium, Panobinostat, Paraplat (Carboplatin), Paraplatin (Carboplatin), Pazopanib Hydrochloride, Pemetrexed Disodium, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Promacta (Eltrombopag Olamine), Purinethol (Mercaptopurine), Purixan (Mercaptopurine), Radium 223 Dichloride, Raloxifene Hydrochloride, Regorafenib, Revlimid (Lenalidomide), Rheumatrex (Methotrexate), Romidepsin, Romiplostim, Rubidomycin (Daunorubicin Hydrochloride), Ruxolitinib Phosphate, Sorafenib Tosylate, Sprycel (Dasatinib), Stivarga (Regorafenib), Sunitinib Malate, Sutent (Sunitinib Malate), Synovir (Thalidomide), Synribo (Omacetaxine Mepesuccinate), Tafinlar (Dabrafenib), Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Totect (Dexrazoxane Hydrochloride), Trametinib, Treanda (Bendamustine Hydrochloride), Trisenox (Arsenic Trioxide), Tykerb (Lapatinib Ditosylate), Vandetanib, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vinorelbine Tartrate, Vismodegib, Vorinostat, Votrient (Pazopanib Hydrochloride), Wellcovorin (Leucovorin Calcium), Xalkori (Crizotinib), Xeloda (Capecitabine), Xofigo (Radium 223 Dichloride), Xtandi (Enzalutamide), Zaltrap (Ziv-Aflibercept), Zelboraf (Vemurafenib), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate), or combinations thereof. In preferred embodiments, the cancer is non-Hodgkin's lymphoma (NHL).

As described herein, CD20 (also known as Bp35) is a B-lymphocyte-restricted differentiation antigen that is expressed during early pre-B-cell development and remains until plasma cell differentiation. CD20 can be a useful target for B-cell lymphomas as this antigen is expressed at very high densities on the surface of malignant B-cells, i.e., B-cells wherein unabated proliferation can lead to B-cell lymphomas. The Food and Drug Administration (FDA) has approved the therapeutic use of an anti-CD20 antibody, rituximab (RITUXAN®), for use in relapsed and previously treated low-grade non-Hodgkin's lymphoma (NHL). Rituximab acts by binding to the CD20 antigen on B-cells which results in the lysis of the B-cell by a mechanism thought to involve complement-dependent cytotoxicity (CDC) and antibody-dependent cell mediated cytotoxicity (ADCC). In certain embodiments, the therapeutic biologic is an antibody. In preferred embodiments, the antibody is an anti-CD20 antibody.

In some embodiments, the therapeutic biologic is an immunotherapy. In other embodiments, the immunotherapy is an anti-CD20 antibody. In certain embodiments, the anti-CD20 antibody is rituximab. In preferred embodiments of the compositions and methods described herein, may be useful for the treatment of non-Hodgkin's lymphoma (NHL) in a subject in need thereof, comprising administering to the subject a pharmaceutically effective amount of a composition comprising: a plurality of particles suspended in a low viscosity pharmaceutically acceptable liquid carrier, each particle comprising rituximab; wherein the particles have less than about 10% aggregation of the therapeutic biologic or salt thereof; and the concentration of the therapeutic biologic or salt thereof in the composition is about 20 mg/mL to about 700 mg/mL. As described herein, any antibody capable of binding the CD20 antigen may be used in the methods of the instant disclosure. Antibodies which bind the CD20 antigen include, for example: C2B8 (rituximab; RITUXAN®) (U.S. Pat. No. 5,736,137, expressly incorporated herein by reference); the yttrium-[90]-labeled 2138 murine antibody designated Y2B8 (U.S. Pat. No. 5,736,137, expressly incorporated herein by reference); murine IgG2a 131 optionally labeled with 131 1 to generate the 131 1-B1 antibody (BEXXAR®) (U.S. Pat. No. 5,595, 721, expressly incorporated herein by reference); murine monoclonal antibody 1F5 (Press et al. Blood 69(2): 584-591 (1987)); chimeric 2H7 antibody (U.S. Pat. No. 5,677,180 expressly incorporated herein by reference); and monoclonal antibodies L27, G28-2, 93-1 133, B--Cl or NU--B2 available from the International Leukocyte Typing Workshop (Valentine et al., In: Leukocyte TypingIII (McMichael, Ed., p. 440, Oxford University Press (1987)).

In certain embodiments of the disclosure, the anti-CD20 antibody is rituximab. Rituximab is a genetically engineered chimeric murine/human monoclonal antibody. Rituximab is an IgG, kappa immunoglobulin containing murine light and heavy chain variable region sequences and human constant region sequences. Rituximab has a binding affinity for the CD20 antigen of approximately 8.0 nM and is commercially available, e.g., from Genentech (South San Francisco, CA).

In other embodiments, the anti-CD20 antibody used in the present disclosure may be administered along with standard of care chemotherapeutic agents/combinations, for example, CHOP chemotherapy regimen, which is a regimen consisting of the combination of cyclophosphamide, doxorubicin, vincristine and prednisolone. Rituximab has been approved in combination with CHOP chemotherapy for the treatment of certain types of lymphomas and the combination has become known as RCHOP chemotherapy. In certain embodiments, the composition further comprises at least one of cyclophosphamide, doxorubicin, vincristine or prednisolone.

In certain embodiments, the antibody described herein is an antibody that binds tumor cells, such as an antibody against a cell surface receptor or a tumor-associated antigen (TAA). In attempts to discover effective cellular targets for cancer therapy, those skilled in the art have sought to identify transmembrane or otherwise tumor-associated polypeptides that are specifically expressed on the surface of one or more particular types of cancer cell as compared to on one or more normal non-cancerous cells. Often, such tumor-associated polypeptides are more abundantly expressed on the surface of the cancer cells as compared to the surface of the non-cancerous cells. Such cell surface receptor and tumor-associated antigens are known in the art and can be prepared for use in generating antibodies using methods and information which are known in the art.

Exemplary examples of cell surface receptors and TAAs to which the antibodies described herein may be targeted include, but are not limited to, the various receptors and TAAs listed under nucleic acid and protein sequence identification conventions of the National Center for Biotechnology Information (NCBI). Nucleic acid and protein sequences corresponding to any listed cell surface receptors and TAAs are available in public databases such as GenBank and are known in the art.

Also provided herein are methods for treating an inflammatory disease and/or pain condition in a subject in need thereof, comprising administering to the subject a pharmaceutically effective amount of a composition comprising: a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof and the concentration of the therapeutic biologic or salt thereof in the composition is about 20 mg/mL to about 700 mg/mL. In certain embodiments, the methods further comprise a non-steroidal anti-inflammatory drug (NSAID). In still other embodiments, the NSAID may include, but not limited to salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, or a mixture thereof.

In some embodiments of any of the methods described herein, the inflammatory disease or condition includes but are not limited to a joint disease, an ophthalmic disease, retinal disease, Crohn's disease, irritable bowel syndrome, Sjogren's disease, tissue graft rejection, asthma, multiple sclerosis, scleroderma, Goodpasture's syndrome, atherosclerosis, chronic idiopathic thrombocytopenic purpura, Addison's disease, Parkinson's disease, Alzheimer's disease, diabetes, septic shock, myasthenia gravis, inflammatory pelvic disease, inflammatory bowel disease, urethritis, uveitis, sinusitis, pneumonitis, encephalitis, meningitis, myocarditis, osteomyelitis, myositis, hepatitis, gastritis, enteritis, appendicitis, pancreatitis, or cholocystitis.

In other embodiments, the inflammatory disease or condition is a joint disease. In some embodiments, the joint disease includes but are not limited to osteoarthritis, rheumatoid arthritis, spondyloarthritis, systemic juvenile idiopathic arthritis, psoriatic arthritis, gout, ankylosing spondylitis, or juvenile rheumatoid arthritis. In certain embodiments, the subject has previously been diagnosed as having an inflammatory condition.

In some embodiments, the methods provided herein are methods for reducing inflammation, pain, or fever in a subject in need thereof. In other embodiments, the pain includes but are not limited to nociceptive pain, neuropathic pain, psychogenic pain, breakthrough pain, incident pain, back pain, musculoskeletal pain, post-operative pain, operative pain, visceral pain, joint pain, acute pain, inflammatory pain, or chronic pain. In certain embodiments, the inflammation that is reduced is in a joint in the subject. In still other embodiments of any of the methods described herein, the subject has a joint disease.

In some embodiments, the inflammatory and/or pain disease or condition include but are not limited to a joint pain, musculoskeletal pain, back pain, neuropathic pain, nociceptive pain, acute pain, chronic pain, inflammatory pain, operative pain, post-operative pain, visceral pain, incident pain, breakthrough pain, psychogenic pain, Crohn's disease, irritable bowel syndrome (IBS), inflammatory bowel disease (IBD), Sjogren's disease, tissue graft rejection, asthma, multiple sclerosis, scleroderma, Goodpasture's syndrome, atherosclerosis, Addison's disease, Parkinson's disease, Alzheimer's disease, diabetes, septic shock, myasthenia gravis, inflammatory pelvic disease, inflammatory bowel disease, urethritis, uveitis, sinusitis, pneumonitis, encephalitis, meningitis, myocarditis, osteomyelitis, myositis, hepatitis, gastritis, enteritis, appendicitis, pancreatitis, or cholocystitis. In some examples, the inflammatory condition is a joint disease. Non-limiting examples of a joint disease include osteoarthritis, rheumatoid arthritis, spondyloarthritis, systemic juvenile idiopathic arthritis, psoriatic arthritis, gout, ankylosing spondylitis, or juvenile rheumatoid arthritis.

In other embodiments, the inflammatory and/or pain disease or condition is a chronic or acute inflammatory process. In certain embodiments, the chronic or acute inflammatory process can be rheumatoid arthritis, Crohn's disease, colitis ulcerosa, or sepsis.

In some embodiments, the inflammatory and/or pain disease or condition includes but are not limited to a metabolic syndrome or disease, ulcerative colitis, Crohns disease, irritable bowel syndrome (IBS), or inflammatory bowel disease (IBD). In other embodiments, the inflammatory bowel disease (IBD) is small bowel Crohn's disease (CDSB), Colonic Crohn's disease (CDC), or Ulcerative Colitis (UC). In certain embodiments, the metabolic syndrome or disease involves inflammation, such as type II diabetes, obesity, or fatty acid metabolism disorders.

In other embodiments, the compositions and methods described herein, are useful for treating immune disease, acquired hypogammaglobulinemia secondary to hematological malignancies, chronic inflammatory demyelinating polyneuropathy (CIDP), Guillain-Barre Syndrome, Idiopathic thrombocytopenic purpura, inflammatory myopathies, Lambert-Eaton myasthenic syndrome, multifocal motor neuropathy, Myasthenia Gravis, Moersch-Woltmann syndrome, secondary hypogammaglobulinaemia specific antibody deficiency, Acute disseminated encephalomyelitis, Autoimmune haemolytic anaemia; Cicatricial pemphigoid, Evans syndrome, Foeto-maternal/neonatal alloimmune thrombocytopenia (FMAIT/NAIT), Haemophagocytic syndrome, high-risk allogeneic haemopoietic stem cell transplantation, IgM paraproteinaemic neuropathy, kidney transplantation, multiple sclerosis, Opsoclonus myoclonus ataxia, Post-transfusion purpura, Toxic epidermal necrolysis/Steven Johnson syndrome (TEN/SJS), Toxic shock syndrome, Alzheimer's Disease, multiple myeloma, sepsis; B-cell tumors, trauma, or a bacterial, viral, fungal infection.

In some embodiments of any of the methods described herein, the immune disease is common variable immunodeficiency (CVID), congenital agammaglobulinemia, Wiskott-Aldrich syndrome, severe combined immunodeficiency (SCID), primary hypogammaglobulinemia, primary immunodeficiency diseases with antibody deficiency, X-linked agammaglobulinemia (XLA), hypogammaglobulinemia of infancy, or paraneoplastic cerebellar degeneration with no antibodies.

In other embodiments, the immune disease is an autoimmune disease. In certain embodiments, the autoimmune disease include but are not limited to multiple sclerosis, scleroderma, type-I diabetes, rheumatoid arthritis, thyroiditis, Reynaud's syndrome, Sjorgen's syndrome, autoimmune uveitis, autoimmune myocarditis, inflammatory bowel disease, amyotrophic lateral sclerosis (ALS), systemic lupus, neuromyelitis optica, idiopathic thrombocytopenic purpura, myasthenia gravis, ulcerative colitis, Crohn's disease, polyarthritis, graft-versus-host reactions, juvenile-onset diabetes, Hashimoto's thyroiditis, Grave's disease, pernicious anaemia, chronic active (lupoid) hepatitis, psoriatic arthritis, or neurodermatitis.

In certain embodiments, the immune disease can be classified according to low antibody levels, impaired functioning of white blood cells due to T-lymphocyte problems, T-lymphocyte problems, B-lymphocyte problems, killing and malfunctioning of white blood cells, abnormal white blood cell movement, or abnormal complement system. In other embodiments, the infectious disease may be an immune disease, namely common variable immunodeficiency, selective antibody deficiency, transient hypogammaglobulinemia of infancy, X-linked agammaglobulinemia (Bruton's agammaglobulinemia), Chronic mucocutaneous candidiasis, DiGeorge anomaly, Ataxia-telangiectasia, Severe combined immunodeficiency disease, Wiskott-Aldrich syndrome, X-linked lymphoproliferative syndrome, Human Immunodeficiency Virus, Chediak-Higashi syndrome, Leukocyte glucose-6-phosphate dehydrogenase deficiency, Myeloperoxidase, Hyperimmunoglobulinemia E (Job-Buckles syndrome), Leukocyte adhesion defect, Complement component 3 (C3) deficiency, Complement component 6 (C6) deficiency, Complement component 7 (C7) deficiency, or Complement component 8 (C8) deficiency.

In other embodiments, the methods described herein, further comprise administering to the patient a therapeutic agent. In certain embodiments, the therapeutic agent is an anti-inflammatory, an antihistamine, an analgesic or a corticosteroid. In still other embodiments, the methods further comprise a non-steroidal anti-inflammatory drug (NSAID). In some embodiments, the NSAID can be salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, or a mixture thereof.

In some embodiments, the methods are useful for treating neuroblastoma, sarcoma, brain cancer, metastatic brain cancers, ovarian cancer, prostate and breast cancer, lymphoma, colorectal cancer, metastatic colorectal cancer, colorectal carcinoma, colorectal tumors, non-small cell lung cancer, carcinoma, hematological cancers, hematological malignancies, hematologic tumors, gastrointestinal cancers, non-Hodgkin's lymphoma, Hodgkin's lymphoma, B-cell non-Hodgkin lymphoma, metastatic cancer, squamous cell carcinoma, malignant ascites, gastric cancer, head and neck cancer, squamous cell carcinoma of the head and neck, solid tumors, pancreatic cancer, bone metastases, recurrent glioblastoma multiforme, malignant melanoma, melanoma, multiple myeloma, cancer expressing Nectin-4, chronic lymphocytic leukemia, adrenocortical carcinoma, non-small cell lung carcinoma, B-cell lymphoma, B-cell cancers, acute myelogenous leukemia, clear cell renal cell carcinoma, renal cell carcinoma, gastrointestinal adenocarcinomas, pancreatic tumor, gastrointestinal adenocarcinomas, pancreatic tumor, stomach cancer, nasopharyngeal cancer, glioma, acute lymphoblastic leukemia, follicular lymphoma, T-cell lymphoma, platelet aggregation inhibition, inflammatory bowel disease, ulcerative colitis, Crohn's disease, Clostridium difficile colitis, rheumatoid arthritis, plaque psoriatic arthritis, ankylosing spondylitis, juvenile idiopathic arthritis, hemolytic disease of the newborn, multiple sclerosis, amyotrophic lateral sclerosis, hypercholesterolemia, asthma, allergic asthma, chronic asthma, severe allergic disorders, allergic reaction, inflammatory lesions, inflammation, retinopathy of prematurity, thromboembolism, thrombosis, oncology/immune indications, treatment of autoimmune diseases, invasive Candida infection, reduction of scarring after glaucoma surgery, white blood cell diseases, systemic scleroderma, Bacillus anthracis spores, anthrax (prophylaxis and treatment), immunologically mediated inflammatory disorders, immunological diseases, Pseudomonas aeruginosa infection, tumor necrosis factor, reduction of side effects of cardiac surgery, macular degeneration (wet form), neovascular age-related macular degeneration, recovery of motor function after stroke, inflammations of the airways, non-malignant skin cancer, inflammations of the gastrointestinal tract, uveitis, polymyositis, choroidal and retinal neovascularization, muscular dystrophy, muscle atrophy due to orthopedic, sarcopenia, pain, diarrhea caused by E. coli, Alzheimer's disease, sepsis, sepsis caused by gram-negative bacteria, sepsis (Staphylococcus), viral infections, osteoporosis, osteomyelitis, bleeding, infectious disease/influenza A, atopic diseases, paroxysmal nocturnal hemoglobinuria, heart attack, stroke, traumatic shock, hepatitis B, chronic hepatitis B, appendicitis, acute sciatic pain, respiratory syncytial virus infection, respiratory syncytial virus prevention, rabies (prophylaxis), idiopathic pulmonary fibrosis, pain, HIV infection, cytomegalovirus infection, hemorrhagic shock, fibrosis, percutaneous coronary intervention, Staphylococcus aureus infection, prevention of organ transplant rejections, graft versus host disease, reversal of anticoagulant effects of dabigatran, antineoplastic agent, myostatin inhibitor, dyslipidemia, diabetes, diabetes mellitus type 1, cardiac imaging, diagnostic agent, or tumor detection. In other embodiments, the organ transplant rejections (host-versus-graft reactions) is a prophylaxis for transplant rejections. In certain embodiments, the methods are useful for treating non-malignant skin cancer. In preferred embodiments, the methods are useful for treating non-malignant skin cancer.

Provided herein are methods of treating renal disease in a subject in need thereof, comprising administering to the subject a pharmaceutically effective amount of a composition comprising: a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL. In certain embodiments, provided herein, are methods for treating membranoproliferative glomerulonephritis (MPGN), membranoproliferative glomerulonephritis (MPGN) pathogenesis, focal segmental glomerulosclerosis (FSGS), membranous nephropathy (MN), severe membranous nephropathy (MN), steroid-resistant nephrotic syndrome, vasculitis, or a combination thereof, in a subject in need thereof, comprising administering to the subject a pharmaceutically effective amount of a composition comprising: a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

By "treatment", with respect to renal disease, is meant by: (1) inhibiting development of symptoms of the disease, e.g., causing the clinical symptoms of the disease not to develop in an animal (e.g., a human) that may have or be predisposed to develop the disease but does not yet experience or display symptoms of the disease; (2) inhibiting the disease, e.g., arresting the development of the disease or one or more of its clinical symptoms; or (3) relieving or ameliorating the disease, e.g., causing regression of the disease or one or more of its clinical symptoms. For example, treatment can refer to relieving one or more symptoms associated with renal disease. Treatment of renal disease does not require a total absence of disease. For example, a decrease of at least 25% or at least 50% of one or more of the symptoms or undesired consequences of the disease can be sufficient.

By "decrease" or "reduce" is meant becoming less or smaller, as in number, amount, size, or intensity. In certain embodiments, decreasing the risk of a disease (e.g., such as focal segmental glomerulosclerosis (FSGS)) includes a decrease in the likelihood of developing the disease by at least about 20%, for example by at least about 30%, 40%, 50%, 60%, 70%, 80%, or 90%. In other embodiments, decreasing the risk of a disease includes a delay in the development of the disease, for example a delay of at least about six months, such as about one year, such as about two years, about five years, or about ten years.

The term "renal disease" or "kidney disease", as generally used herein, is meant to be a disorder that specifically leads to damage of the kidneys. Renal diseases include but are not limited to focal segmental glomerulosclerosis (FSGS), hypertensive end stage renal disease (ESRD), nephropathy secondary to systemic lupus erythematosus, diabetic nephropathy, hypertensive nephropathy, IgA nephropathy, IgA nephritis, HIV-associated nephropathy, non-diabetic chronic kidney disease, chronic kidney disease, reflux nephropathy, glomerulonephritis, glomerulonephrosis, polycystic renal disease, or xanthine oxidase deficiency, or a combination thereof. Renal disease can be chronic or acute. Chronic renal disease, as described herein, in certain embodiments, can progress from stage 1 (slightly diminished kidney function) to stage 2 (mild reduction in function), stage 3 (moderate reduction in function), stage 4 (severe reduction in function), or stage 5 (established kidney failure).

In some embodiments, "a condition or symptom associated with" may be any pathology that arises as a consequence of, preceding, or proceeding from the renal disease. For example, where the renal disease is focal segmental glomerulosclerosis (FSGS), the condition or relevant symptom may be microbial infection. In other embodiments, the methods of treating described herein are for the minimization or treatment of a condition or symptom in an individual that is associated with a renal disease in the individual. In certain embodiments, the subject is a mammal. In preferred embodiments, the subject is human.

In some embodiments, a desired response is to prevent the development of renal disease (e.g., focal segmental glomerulosclerosis (FSGS)). In other embodiments, a desired response is to delay the development or progression of renal disease (e.g., focal segmental glomerulosclerosis (FSGS)), for example, by at least about three months, at least about six months, at least about one year, at least about two years, at least about five years, or at least about ten years. In certain embodiments, a desired response is to decrease the signs and symptoms of renal disease (e.g., focal segmental glomerulosclerosis (FSGS)), such as scarring of the tissues of the kidney, and/or neurological symptoms in the limbs or associated with speaking.

As disclosed herein, the methods can be used for treating renal disease. In some embodiments, the renal disease is antineutrophil cytoplasmic antibodies (ANCA)-associated vasculitis (AAV), idiopathic membranous nephropathy, membranoproliferative glomerulonephritis (MPGN), lupus nephritis, systemic lupus erythematosus (SLE), minimal change disease (MCD), focal segmental glomerulosclerosis (FSGS), antibody-mediated renal transplant rejection, membranous nephropathy (MN), severe membranous nephropathy (MN), severe membranous nephropathy (MN), steroid-resistant nephrotic syndrome, vasculitis, IgA nephritis, diabetic nephropathy, chronic kidney disease, reflux nephropathy, glomerulonephritis, glomerulonephrosis, polycystic renal disease, or as part of desensitizing regimens enabling ABO-/human leucocyte antigen (HLA)-incompatible kidney transplantation. In preferred embodiments, the methods can be used for treating membranoproliferative glomerulonephritis (MPGN), membranoproliferative glomerulonephritis (MPGN) pathogenesis, focal segmental glomerulosclerosis (FSGS), membranous nephropathy (MN), severe membranous nephropathy (MN), steroid-resistant nephrotic syndrome, vasculitis, or a combination thereof.

In certain embodiments, the methods described herein, may significantly reduce renal damage in people with a common form of kidney disease called membranous nephropathy. In preferred embodiments, the methods can be used as a first-line therapy for severe membranous nephropathy (MN).

In certain embodiments, the methods can show best treatment outcomes in patients with steroid-resistant nephrotic syndrome, particularly those with focal segmental glomerulosclerosis (FSGS) and young patients who suffer with recurrent FSGS.

In some embodiments, the methods described herein, can reduce the number of harmful antibodies called autoantibodies (ANCA) that a body produces by targeting and destroying B cells. ANCA's attack healthy tissue and cells and are produced by B cells. The autoantibodies target specific white blood cells called neutrophils and the ANCA's cause neutrophils to stick and clump to the walls of small blood vessels in different tissues and organs of the body. In other embodiments, the methods can be used for treating vasculitis that can harm the kidneys.

In certain other embodiments, the methods can be used to treat or reduce the likelihood of developing focal segmental glomerulosclerosis (FSGS) in a subject who has not had a kidney transplant, or in a subject having been identified as being at risk of developing the renal disease.

In some embodiments, the subject is an end stage renal disease (ESRD) patient, a patient on immunosuppressive therapy, an AIDS patient, a diabetic patient, a neonate, a transplant patient, a patient with malfunctioning immune system, an elderly person, a patient with autoimmune disease, a burn patient, a cancer patient, or a patient in an acute care setting.

The methods as described herein, may be administered in combination with other known therapies for the treatment of renal disease. In some embodiments, the composition further comprises at least one therapeutic agent. For example, a subject treated with composition of the disclosure may also be treated with a blood pressure medication, a steroid, and/or an immunosuppressive agent. Examples of therapeutics include blood pressure medications (e.g., a diuretic (e.g., chlorthalidone, chlorothiazide, furosemide, hydrochlorothiazide, indapamide, metolazone, amiloride hydrochloride, spironolactone, triamterene, bumetanide, or a combination thereof), an alpha adrenergic antagonist (e.g., alfuzosin, doxazosin, prazosin, terazosin, or tamsulosin, or a combination thereof), a central adrenergic inhibitor (e.g., clonidine, guanfacine, or methyldopa, or a combination thereof), an angiotensin converting enzyme (ACE) inhibitor (e.g., benazepril, captopril, enalapril, fosinopril, lisinopril, moexipril, perindopril, quinapril, ramipril, or trandolapril, or combinations thereof), an angiotensin II receptor blocker (e.g., candesartan, eprosartan, irbesartan, losartan, olmesartan, telmisartan, or valsartan, or combinations thereof), an alpha blocker (e.g., doxazosin, prazosin, or terazosin, or a combination thereof), a beta blocker (e.g., acebutolol, atenolol, betaxolol, bisoprolol, carteolol, metoprolol, nadolol, nebivolol, penbutolol, pindolol, propranolol, solotol, or timolol, or a combination thereof), a calcium channel blocker (e.g., amlodipine, bepridil, diltiazem, felodipine, isradipine, nicardipine, nifedipine, nisoldipine, or verapamil, or combination thereof), a vasodilator (e.g., hydralazine or minoxidil, or combination thereof), and a renin inhibitor (e.g., aliskiren), or combinations thereof), a steroid (e.g., a corticosteroid, such as cortisone, prednisone, methylprednisolone, or prednisolone), or an anabolic steroid (anatrofin, anaxvar, annadrol, bolasterone, decadiabolin, decadurabolin, dehydropiandrosterone (DHEA), delatestryl, dianiabol, dihydrolone, durabolin, dymethazine, enoltestovis, equipose, gamma hydroxybutyrate, maxibolin, methatriol, methyltestosterone, parabolin, primobolin, quinolone, therabolin, trophobolene, and winstrol), or an immunosuppressive agent, such as a glucocorticoid, a cytostatic, an antibody, or an anti-immunophilin and/or mychophenolate mofetil (MMF), FK-506, azathioprine, cyclophosphamide, methotrexate, dactinomycin, antithymocyte globulin (AT-GAM), a muromonoab-CD3 antibody, basilizimab, daclizumab, cyclosporin, tacrolimus, voclosporin, sirolimus, an interferon, infliximab, etanercept, adalimumab, fingolimod, and/or myriocin). In preferred embodiments, the composition further comprises at least one of a steroid, diphenhydramine, acetaminophen, a blood pressure medication, immunosuppressive agent, or a combination thereof.

Also provided herein are methods of treating skin disease or condition in a subject in need thereof, comprising administering to the subject a pharmaceutically effective amount of a composition comprising: a plurality of particles suspended in a low viscosity pharmaceutically acceptable liquid carrier, each particle comprising at least one therapeutic biologic or a salt thereof wherein the particles have less than about 10% aggregation of the therapeutic biologic or salt thereof and the concentration of the therapeutic biologic or salt thereof in the composition is about 20 mg/mL to about 700 mg/mL. In certain embodiments, the methods further comprise a non-steroidal anti-inflammatory drug (NSAID). In still other embodiments, the NSAID may include, but not limited to salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, or a mixture thereof.

The methods as described herein, may be administered in combination with other known therapies for the treatment of skin disease. In some embodiments, the composition further comprises at least one therapeutic agent. For example, a subject treated with composition of the disclosure may also be treated with a blood pressure medication, a steroid, and/or an immunosuppressive agent. Examples of therapeutics include blood pressure medications (e.g., a diuretic (e.g., chlorthalidone, chlorothiazide, furosemide, hydrochlorothiazide, indapamide, metolazone, amiloride hydrochloride, spironolactone, triamterene, bumetanide, or a combination thereof), an alpha adrenergic antagonist (e.g., alfuzosin, doxazosin, prazosin, terazosin, or tamsulosin, or a combination thereof), a central adrenergic inhibitor (e.g., clonidine, guanfacine, or methyldopa, or a combination thereof), an angiotensin converting enzyme (ACE) inhibitor (e.g., benazepril, captopril, enalapril, fosinopril, lisinopril, moexipril, perindopril, quinapril, ramipril, or trandolapril, or combinations thereof), an angiotensin II receptor blocker (e.g., candesartan, eprosartan, irbesartan, losartan, olmesartan, telmisartan, or valsartan, or combinations thereof), an alpha blocker (e.g., doxazosin, prazosin, or terazosin, or a combination thereof), a beta blocker (e.g., acebutolol, atenolol, betaxolol, bisoprolol, carteolol, metoprolol, nadolol, nebivolol, penbutolol, pindolol, propranolol, solotol, or timolol, or a combination thereof), a calcium channel blocker (e.g., amlodipine, bepridil, diltiazem, felodipine, isradipine, nicardipine, nifedipine, nisoldipine, or verapamil, or combination thereof), a vasodilator (e.g., hydralazine or minoxidil, or combination thereof), and a renin inhibitor (e.g., aliskiren), or combinations thereof), a steroid (e.g., a corticosteroid, such as cortisone, prednisone, methylprednisolone, or prednisolone), or an anabolic steroid (anatrofin, anaxvar, annadrol, bolasterone, decadiabolin, decadurabolin, dehydropiandrosterone (DHEA), delatestryl, dianiabol, dihydrolone, durabolin, dymethazine, enoltestovis, equipose, gamma hydroxybutyrate, maxibolin, methatriol, methyltestosterone, parabolin, primobolin, quinolone, therabolin, trophobolene, and winstrol), or an immunosuppressive agent, such as a glucocorticoid, a cytostatic, an antibody, or an anti-immunophilin and/or mychophenolate mofetil (MMF), FK-506, azathioprine, cyclophosphamide, methotrexate, dactinomycin, antithymocyte globulin (AT-GAM), a muromonoab-CD3 antibody, basilizimab, daclizumab, cyclosporin, tacrolimus, voclosporin, sirolimus, an interferon, infliximab, etanercept, adalimumab, fingolimod, and/or myriocin). In preferred embodiments, the composition further comprises at least one of a steroid, diphenhydramine, acetaminophen, a blood pressure medication, immunosuppressive agent, or a combination thereof. In particular, the Food and Drug Administration (FDA) has approved the use for rituximab for granulomatosis with polyangiitis and microscopic polyangiitis in adult patients in combination with systemic steroids. In preferred embodiments, the composition further comprises at least one steroid.

The term "skin disease" or "skin condition", as generally used herein, is meant to be a disorder that specifically leads to damage of the skin. Skin diseases include but are not limited to dermatitis, contact dermatitis, eczema, urticaria, rosacea, scarring psoriatic lesions in the skin, psoriasis, atopic dermatitis, contact sensitivity, acne, dermatomyositis, leukoderma vulgaris, ichthyosis vulgaris, photoallergic sensitivity, infantile hemangioma, verruca vulgaris, psoriasis, neurofibromatosis, epidermolysis bullosa, atopic eczema, food allergy, granulomatosis with polyangiitis (e.g., Wegener granulomatosis), cutaneous vasculitis (e.g., acute haemorrhagic oedema, Henoch-Schönlein purpura, hypersensitivity vasculitis), primary blistering diseases, dermatomyositis, atopic dermatitis (e.g., eczema), lupus erythematosus, or primary blistering diseases (e.g., autoimmune bullous disorders), which are associated with autoantibodies directed against various structural support proteins in the epidermis and dermoepidermal junction, *Pemphigus vulgaris* and treatment-resistant cases (e.g., *Pemphigus foliaceus*, paraneoplastic pemphigus associated with CD20+ lymphoma, bullous pemphigoid, epidermolysis bullosa acquisita, mucous membrane pemphigoid), refractory cutaneous lupus erythematosus, thrombotic thrombocytopenic purpura, or a combination thereof.

In some embodiments, as described herein, the subject in need or recognized need is suffering from skin disease which includes, by way of example, is dermatitis, contact dermatitis, eczema, urticaria, rosacea, scarring psoriatic lesions in the skin, psoriasis, atopic dermatitis, contact sensitivity, acne, dermatomyositis, leukoderma vulgaris, ichthyosis vulgaris, photoallergic sensitivity, infantile hemangioma, verruca vulgaris, psoriasis, neurofibromatosis, epidermolysis bullosa, atopic eczema, food allergy, granulomatosis with polyangiitis (e.g., Wegener granulomatosis), cutaneous vasculitis (e.g., acute haemorrhagic oedema, Henoch-Schönlein purpura, hypersensitivity vasculitis), primary blistering diseases, dermatomyositis, atopic dermatitis (e.g., eczema), lupus erythematosus, or primary blistering diseases (e.g., autoimmune bullous disorders), which are associated with autoantibodies directed against various structural support proteins in the epidermis and dermoepidermal junction, *Pemphigus vulgaris* and treatment-resistant cases (e.g., *Pemphigus foliaceus*, paraneoplastic pemphigus associated with CD20+ lymphoma, bullous pemphigoid, epidermolysis bullosa acquisita, mucous membrane pemphigoid), refractory cutaneous lupus erythematosus, thrombotic thrombocytopenic purpura, or a combination thereof.

In other embodiments, the skin disease is granulomatosis with polyangiitis (e.g., Wegener granulomatosis), cutaneous vasculitis (e.g., acute haemorrhagic oedema, Henoch-Schönlein purpura, hypersensitivity vasculitis), primary blistering diseases, dermatomyositis, atopic dermatitis (e.g., eczema), lupus erythematosus, or primary blistering diseases (e.g., autoimmune bullous disorders), which are associated with autoantibodies directed against various structural support proteins in the epidermis and dermoepidermal junction, *Pemphigus vulgaris* and treatment-resistant cases (e.g., *Pemphigus foliaceus*, paraneoplastic pemphigus associated with CD20+ lymphoma, bullous pemphigoid, epidermolysis bullosa acquisita, mucous membrane pemphigoid), refractory cutaneous lupus erythematosus, thrombotic thrombocytopenic purpura, or a combination thereof.

In certain embodiments, the skin disease is granulomatosis with polyangiitis, e.g., Wegener granulomatosis, or microscopic polyangiitis. Granulomatosis with polyangiitis is a potentially fatal form of vasculitis in which, for example, there is an immune reaction in which antibodies damage small blood vessel walls and surrounding tissues. In certain embodiments, patients affected with granulomatosis with polyangiitis suffer from ulcers of the skin, e.g., palpable purpura, nodules, papules and vesicles, pyoderma gangrenosum, Raynaud phenomenon, or a combination thereof.

In certain other embodiments, the skin disease is cutaneous vasculitis. Cutaneous vasculitis is a group of disorders in which there are inflamed blood vessels, e.g., capillaries, venules, arterioles, lymphatics, in the skin. Classification of cutaneous vasculitis include, but are not limited to: capillaritis, e.g., progressive pigmented purpura: the most common form of capillaritis, itching purpura, pigmented purpuric lichenoid dermatosis, *Purpura annularis* telangiectodes, capillaritis in association with contact allergy, lichen *aureus*; small vessel vasculitis, e.g., idiopathic, drug or infection-induced cutaneous small vessel vasculitis (hypersensitivity vasculitis), Henoch-Schönlein purpura, Acute haemorrhagic oedema of infancy, urticarial vasculitis, exercise-induced vasculitis, erythema elevatum diutinum, malignant atrophic papulosis (degos), cryoglobulinaemia, recurrent cutaneous necrotising eosinophilic vasculitis, ANCA-associated vasculitis, microscopic polyangiitis, eosinophilic granulomatosis with polyangiitis/Churg-Strauss, granulomatosis with polyangiitis, lymphomatoid granulomatosis; medium vessel vasculitis, cutaneous polyarteritis nodosa, Kawasaki disease, nodular vasculitis; or large vessel vasculitis, e.g., temporal arteritis, Takayasu disease, giant cell arteritis. Vasculitis is classified as a type-III hypersensitivity reaction involving immune complexes, i.e., antibodies bound to antigens in the affected blood vessels. In still other embodiments, the skin disease is atopic dermatitis. Atopic dermatitis (eczema) results from a complex interaction between various immune cells and proteins and in many patients is characterized by high levels of serum IgE.

Human immunodeficiency virus (HIV) affects specific cells of the immune system, called CD4 cells or T cells. Over time, HIV can destroy these cells to a point where the body cannot fight off infections and disease. HIV disease has a well-documented progression. Untreated, HIV is almost universally fatal because it eventually overwhelms the immune system resulting in acquired immunodeficiency syndrome (AIDS). HIV treatment helps people at all stages of the disease and can slow or prevent progression from one stage to the next. As is known in the art, the clinical signs and symptoms of HIV infection are primarily due to a profound loss of lymphocytes marked with the CD3 and CD4 antigens (CD4.sup.+ T-cells). It is also generally accepted that the infectious agent in AIDS is HIV. Non-limiting examples of symptoms of HIV infection within the first couple of weeks following contact with the virus include: fever, headache, sore throat, swollen lymph glands, and rash. Additional symptoms of HIV infection that can appear later include: mild infections, swollen lymph nodes, diarrhea, weight loss, fever, cough, and shortness of breath. HIV infection typically progresses to AIDS in about 10 years. By the time AIDS develops, the subject's immune system has been severely damaged. Later symptoms of HIV infection or AIDS include: soaking night sweats, shaking chills or fever higher than 38° C. for several weeks, cough or shortness of breath, chronic diarrhea, persistent white spots or unusual lesions on the tongue or in mouth, headaches, persistent unexplained fatigue, blurred or distorted vision, weight loss, and skin rashes or bumps. Subjects having HIV infection or AIDS also have an increased risk of developing a number of opportunistic infections, e.g., bacterial, viral, fungal, and protozoal infections, and cancers. Non-limiting examples of opportunistic bacterial infections include bacterial strains that cause diarrhea (e.g., *Salmonella* sp., *Campylobacter* sp., *Shigella* sp.), bacterial strains that cause pneumonia (e.g., *Streptococcus pneumonia, Haemophilus influenzae, Pseudomonas aeruginosa, Staphylococcus aureus, Legionella pneumophila, Mycoplasma pneumonia*, and *Chlamydia pneumoniae*), *Mycobacterium avium, Treponema pallidum*, and *Mycobacterium tuberculosis*. Non-limiting examples of opportunistic viral infections include: cytomegalovirus (CMV), hepatitis C, herpes simplex virus (oral and genital herpes), herpes zoster virus (shingles), human papilloma virus (HPV), molluscum contagiosum virus (MCV), Epstein-Barr virus (EBV), and JC polyomavirus. Non-limiting examples of opportunistic fungal infections include: *Aspergillus, Candida albicans, Coccidioides immitis, Coccidioides posadasii, Crytococcus neoformans*, and *Histoplasma capsulatum*. Non-limiting examples of protozoal opportunistic infections include: *Crytposporidium* sp., *Isospora belli, Microsporidium* sp. (e.g., *Enterocytozoon bieneusi*), *Pneumocystis jiroveci*, and *Toxoplasma gondii*. Subjects with an HIV infection or AIDS also have an increased risk of developing a cancer, including but limited to: anal dysplasia or cancer, cervical dysplasia or cancer, Kaposi's sarcoma, and lymphomas.

As used herein, the term "human immuno deficiency virus (HIV) infection" is meant by the presence of at least one HIV virion in a subject, a detectable level of HIV virions in a subject, or the presence or a detectable level of HIV genomic nucleic acid in a subject. Non-limiting examples of methods for detecting the presence or the levels of HIV virions or HIV genomic nucleic acid in a subject are known in the art. For examples, methods for detecting or measuring the level of an HIV genomic nucleic acid in a subject are known in the art, e.g., reverse transcriptase polymerase chain reaction. Methods for detecting the presence of an HIV virion indirectly are also known in the art, e.g., measurement of anti-HIV antibody titers in a subject. With respect to human immuno deficiency virus (HIV) infection, "reduce" refers to decrease in number, amount, or level. For example, reducing HIV viral load refers to a reduction or decrease in the amount of HIV in an involved body fluid. Reduction generally can be compared to an initial of starting number, amount, or level, but can also be compared to a control or to a standard number, amount, or level.

In some embodiments, compounds that inhibit HIV infection of CD4 T cells include, for example, entry inhibitors, such as C—C chemokine receptor type 5 (CCR5) inhibitors, C-X-X chemokine receptor type 4 (CXCR4) inhibitors, CD4 inhibitors, gp120 inhibitors, and gp41 inhibitors (such as enfuvirtide); and anti-inflammatories, such as hydroxychloroquine, chloroquine, PD-1 inhibitors, type I interferons, IL6, cyclo-oxygenase-2 inhibitors, peroxisome proliferator-activated receptor-c (PPAR-c) agonists (such as pioglitazone and leflunomide), methotrexate, mesalazine, and anti-fibrotic agents (such as angiotensin-converting enzyme (ACE) inhibitors). Examples of CCR5 inhibitors include maraviroc, aplaviroc, and vicriviroc. Examples of other entry inhibitors include TNX-355, PRO 140, BMS-488043, plerixafor, epigallocatechin gallate, anti-gp120 antibody, such as antibody b12, griffithsin, DCM205, and Designed Ankyrin Repeat Proteins (DARPins). HAART is used to reduce the likelihood of the virus developing resistance. Compounds for HAART are well known and include, for example, a combination of two or more nucleoside reverse transcriptase inhibitors (NRTIs), such as tenofovir, emtricitabine, zidovudine (AZT), lamivudine (3TC), abacavir, and tenofovir alafenamide fumarate; and one or more non-nucleotide reverse transcriptase inhibitors (NNRTIs), such as efavirenz, rilpivirine, and etravirine; integrase inhibitors, such as raltegravir and elvitegravir; and/or protease inhibitors, such as ritonavir, darunavir, atazanavir, lopinavir, and cobicistat. HAART medicines that are most often used to treat HIV infection include nucleoside/nucleotide reverse transcriptase inhibitors, such as tenofovir, emtricitabine, and abacavir; and non-nucleoside reverse transcriptase inhibitors (NNRTIs), such as efavirenz, nevirapine, or etravirine; protease inhibitors (PIs), such as atazanavir, ritonavir, or darunavir; fusion and entry inhibitors, such as enfuvirtide and maraviroc; and integrase inhibitors, such as raltegravir. In other embodiments, compounds that stimulate reactivation of latent HIV include, for example, histone deacetylase (HDAC) inhibitors, such as vorinostat, pomidepsin, panobinostat, givinostat, belinostat, valproic acid, CI-994, MS-275, BML-210, M344, NVP-LAQ824, mocetinostat, and sirtuin inhibitors; NF-κB-inducing agents, such as anti-CD3/CD28 antibodies, tumor necrosis factor alpha (TNFα), prostratin, ionomycin, bryostatin-1, and picolog; histone methyltransferase (HMT) inhibitors, such as BIX-01294 and chaetocin; pro-apoptotic and cell differentiating molecules, such as JQ1, nutlin3, disulfiram, aphidicolin, hexamethylene bisacetamide (HMBA), dactinomycin, aclarubicin, cytarabine, Wnt small molecule inhibitors, and Notch inhibitors; immune modulators, such as anti-PD-1 antibodies, anti-CTLA-4 antibodies, anti-TRIM-3 antibodies, and BMS-936558; and CD4 T cell vaccines. Combinations of such stimulators can also be used. The effects of some stimulators on reactivation of HIV can also be enhanced by combination with other compounds.

In other embodiments, "symptoms of HIV infection" is meant any physical manifestation of an HIV infection or AIDS in a human subject that is measurable or detectable. One or more symptoms of an HIV infection can be detected during physical examination by a health care professional. Non-limiting examples of symptoms of HIV infection in a human include: fever, headache, muscle and joint pain, sore throat, rash, diarrhea, swollen lymph nodes, e.g., neck, axilla, or groin lymph nodes, night sweats, poor appetite, fatigue, weight loss, dry cough, shortness of breath, depression, peripheral neuropathy, confusion, changes in the level of consciousness, lesions on the tongue or in the mouth, blurred or distorted vision, or a combination thereof. In certain embodiments, "symptom of HIV infection" also includes the presentation of one or more opportunistic infections, e.g., bacterial, viral, fungal, and/or parasitic infection in a subject. An opportunistic infection typically is not observed in human subjects with healthy immune systems, e.g., immunocompetent subjects. Non-limiting examples of opportunistic infections include: cytomegalovirus (CMV) infection, *Pneumocystis carinii* pneumonia (PCP) (*Pneumocystis jirovecii*), *Mycobacterium tuberculosis* infection, recurrent pneumonia, Candidiasis infection (thrush), coccidiomycosis, cryptococcosis, herpes simplex virus infection, e.g., herpes simplex virus-1 infection, *Salmonella* infection, *Shigella* infection, *Listeria* infection, *Campylobacter* infection, cryptosporidiosis, microsporidiosis, *Myocobacterium avium* complex (MAC or MAI), astorvirus, histoplasmosis, isosporiasis, adenovirus infection, rotavirus infection, *Clostridium difficile* infection, toxoplasmosis (*Toxoplasma gondii*), *Cryptococcus neoformans* infection, *Penicillium marneffei* infection, or a combination thereof.

In some embodiments, the administering of the composition comprising: a plurality of particles comprising at least one therapeutic biologic or a salt thereof, reduces an opportunistic infection in a subject having an HIV infection or AIDS or reduces the risk of developing an opportunistic infection in a subject having an HIV infection or AIDS. For example, the methods described herein may result in a significant decrease in the number or the severity, frequency, or duration of one or more symptoms of an opportunistic bacterial, fungal, viral, or parasitic infection, e.g., any of the exemplary opportunistic bacterial, fungal, viral, or parasitic infections described herein, in a subject having an HIV infection or AIDS that has such an opportunistic infection. In other embodiments, the methods described herein, decrease the risk of developing an opportunistic bacterial, viral, fungal, or parasitic infection, e.g., any of the exemplary opportunistic bacterial, fungal, viral, or parasitic infections described herein, in a subject having an HIV infection or AIDS and not having an opportunistic bacterial, viral, fungal, or parasitic infection, e.g., as compared to a subject or group of subjects having an HIV infection or AIDS and not receiving the treatment or receiving an alternative form of treatment. In still other embodiments, the methods described herein decrease the risk of developing cancer, e.g., any of the exemplary cancers described herein, in a subject having an HIV infection or AIDS, e.g., as compared to a subject or group of subjects having an HIV infection or AIDS and not receiving the treatment or receiving an alternative form of treatment. In certain other embodiments, the administering of the composition comprising: a plurality of particles suspended in a low viscosity pharmaceutically acceptable liquid carrier, each particle comprising at least one therapeutic biologic or a salt thereof, results in a decrease, e.g., a significant or detectable decrease, e.g., at least about 5%, 10%, 15%, 20%, 25%, or about 30% decrease in HIV titer in the subject.

Pharmaceutical Compositions

In certain embodiments, the disclosure relates to a composition, e.g., pharmaceutical composition, comprising a plurality of particles suspended in a low viscosity pharmaceutically acceptable liquid carrier, each particle comprising any one of the aforementioned therapeutic biologics.

In one aspect, the disclosure provides a composition, e.g., a pharmaceutically effective composition, comprising: a plurality of particles suspended in a low viscosity pharmaceutically acceptable liquid carrier, each particle comprising at least one therapeutic biologic or a salt thereof; wherein the particles have less than about 10% aggregation of the therapeutic biologic or salt thereof; and the concentration of the therapeutic biologic or salt thereof in the composition is about 20 mg/mL to about 700 mg/mL.

Patients, including but not limited to humans, can be treated by administering to the patient an effective amount of a pharmaceutical composition comprising the active therapeutic biologic or a pharmaceutically acceptable prodrug or salt thereof in the presence of a pharmaceutically acceptable liquid, carrier or diluent. The active materials can be administered by any appropriate route, for example, parenteral, intradermally, or subcutaneously, in liquid form. Parenteral dosage forms are intended for administration as an injection. Common injection types are intravenous (into a vein), subcutaneous (under the skin), and intramuscular (into muscle). Infusions typically are given by intravenous route.

The concentration of active therapeutic biologic in the composition will depend on absorption, inactivation and excretion rates of the drug as well as other factors known to those of skill in the art. It is to be noted that dosage values will also vary with the severity of the condition to be alleviated, and possible drug-drug interactions with antiretroviral medications. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

The therapeutic biologic or a pharmaceutically acceptable prodrug or salts thereof can also be mixed with other additives or active materials that do not impair the desired action, or with materials that supplement the desired action, such as antibiotics, antifungals, anti-inflammatories or other antivirals, including but not limited to nucleoside compounds. Solutions, suspensions or compositions used herein for intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates, histidine, succinates, phosphates, or a combination thereof, and agents for the adjustment of tonicity, such as sodium chloride or dextrose, or combinations thereof. The parental preparation can be enclosed in disposable syringes or cartridges made of glass or plastic or the like. In certain embodiments, the composition is dispensed from a prefilled syringe.

The compositions and methods of the present disclosure may be utilized to treat a subject in need thereof. In certain embodiments, the subject is a mammal such as a human, or a non-human mammal. When administered to a mammal, such as a human, the composition is preferably administered as a pharmaceutical composition comprising, for example, a composition of the disclosure and a pharmaceutically acceptable liquid carrier. Pharmaceutically acceptable liquid carriers are known in the art and include, for example, aqueous solutions such as water or physiologically buffered saline or other solvents or vehicles such as glycols, glycerol, oils such as olive oil or injectable organic esters. In preferred embodiments, when such pharmaceutical compositions are for human administration, e.g., for parenteral administration, the aqueous solution is pyrogen-free, or substantially pyrogen-free. In certain preferred embodiments, the pharmaceutically acceptable liquid carrier is non-aqueous.

In some embodiments, a pharmaceutically acceptable carrier can contain physiologically acceptable agents that act, for example, to stabilize or to increase the absorption of a therapeutic biologic of the disclosure. Such physiologically acceptable agents include, for example, carbohydrates, such as glucose, sucrose, trehalose or dextrans; antioxidants, such as ascorbic acid or glutathione; chelating agents; low molecular weight proteins; or other stabilizers or excipients. The choice of a pharmaceutically acceptable carrier, including a physiologically acceptable agent, depends, for example, on the route of administration of the composition. In preferred embodiments, the composition is administered by subcutaneous syringe injection.

The phrase "pharmaceutically acceptable" is employed herein to refer to those therapeutic biologics, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The term "pharmaceutically acceptable" can refer to therapeutic biologics and compositions that do not produce an adverse, allergic, or other untoward reaction when administered to a mammal, such as a human, as appropriate. The preparation of a pharmaceutical composition comprising an antibody or additional active ingredient will be known to those of skill in the art in light of the present disclosure. Moreover, for mammal, e.g., human, administration, it will be understood that preparations should meet sterility, pyrogenicity, general safety, and purity standards as required by FDA Office of Biological Standards.

The phrase "pharmaceutically acceptable carrier" as used herein, means a pharmaceutically acceptable material, composition or vehicle, such as a liquid, diluent, excipient, or solvent. Each carrier must be "acceptable" in the sense of being compatible with the other ingredients of the compositions and not injurious to the patient. Some examples of materials which can serve as pharmaceutically acceptable carriers include but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions. One skilled in the art may dilute or increase the volume of the therapeutic biologic with an inert material. These diluents could include carbohydrates, especially trehalose, mannitol, a-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell. The term "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

In some embodiments, pharmaceutical compositions or formulations for parenteral administration include aqueous solutions of the active therapeutic biologics in water-soluble form. Preferably, suspensions of the active therapeutic biologics may be prepared as appropriate oily injection compositions. Suitable lipophilic solvents or vehicles include fatty oils (e.g., sesame oil, corn oil), or synthetic fatty acid esters (e.g., ethyl oleate or triglycerides), or liposomes. Optionally, the composition may also contain suitable stabilizers or agents which increase the solubility of the therapeutic biologics to allow for the preparation of highly concentrated solutions. A pharmaceutical composition can also include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In certain cases, it will be preferable to include isotonic agents, for example, sugars or sodium chloride.

Suitable buffering agents include: acetic acid and a salt (1-2% w/v); citric acid and a salt (1-3% w/v); boric acid and a salt (0.5-2.5%) w/v); or phosphoric acid and a salt (0.8-2%>w/v). Suitable preservatives include benzalkonium chloride (0.003-0.03%) w/v); chlorobutanol (0.3-0.9% w/v); parabens (0.01-0.25% w/v) or thimerosal (0.004-0.02% w/v).

A pharmaceutical composition, e.g., formulation, as disclosed herein, can be administered to a subject by any of a number of routes of administration including, for example, parenterally (including intramuscularly, intravenously, subcutaneously or intrathecally as, for example, a sterile solution or suspension); intraperitoneally; or subcutaneously. In some embodiments, the composition is administered by parenteral, subcutaneous, oral, epidermal, intradermal, intramuscular, interarterial, intraperitoneal, or intravenous injection. In certain embodiments, a composition may be simply suspended in a non-aqueous liquid carrier. Details of appropriate routes of administration and compositions suitable for same can be found in, for example, U.S. Pat. Nos. 6,110,973; 5,763,493; 5,731,000; 5,541,231; 5,427,798; 5,358,970 and 4,172,896, as well as in patents cited therein. The term "pharmaceutical composition" or "formulation" as disclosed herein, refers to a preparation which is in such form as to permit a therapeutic biologic in the composition to be effective, e.g., when administered to a subject, and which contains no additional components which are unacceptably toxic to a subject to which the composition or formulation would be administered. Such compositions or formulations are sterile. A "sterile" composition or formulation is aseptic or free from all living microorganisms and their spores.

The compositions may conveniently be presented in unit dosage form and may be prepared by any methods known in the art of pharmacy. The amount of active ingredient which can be combined with a liquid carrier material to produce a single dosage form will vary depending upon the host being treated and the particular mode of administration. The amount of active ingredient that can be combined with a carrier material to produce a single dosage form will generally be that amount of the therapeutic biologic which produces a therapeutic effect. Generally, out of one hundred percent, this amount will range about 1% to about 99% of active ingredient, preferably about 50% to about 99%, most preferably about 70% to about 98%.

In some embodiments of the present disclosure, the composition that is suitable for use in the disclosure may be administered parenterally, and in particular subcutaneously.

An effective amount of the composition may be administered in a single dose per day or in fractional doses over the day, for example, two to three times a day. By way of example, the administration of a composition according to the disclosure may be performed at a rate, for example, of 3 times a day or more, generally over a prolonged period of at least a week, 2 weeks, 3 weeks, 4 weeks, or even 4 to 15 weeks, optionally comprising one or more periods of stoppage or being repeated after a period of stoppage. In some embodiments, the composition is administered one or more times a day, e.g., 1, 2, 3, 4, 5, 6, 7, 8, 9, 10, or more times a day. In other embodiments, the composition is administered for about 1 to about 31 days, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In certain embodiments, the composition is administered for at least 1 day. In still other embodiments, the composition is administered for one or more weeks, e.g., 1, 2, 3, 4, 5, 6, 7, 8, 9, 10, 11, 12, 13, 14, or more weeks. In yet other embodiments, the composition is administered for one or more months, e.g., 1, 2, 3, 4, 5, 6, 7, 8, 9, 10, 11, 12, or more months.

In certain embodiments, the therapeutic biologic may be administered at a dose of about 1 mg to about 1,500 mg per day, about 5 mg to about 1,300 mg per day, about 10 mg to about 900 mg per day, about 20 mg to about 600 mg per day, about 40 mg to about 300 mg per day, about 150 mg to about 350 mg per day, about 40 to about 150 mg per day, about 25 mg to about 150 mg per day, about 2.5 mg to about 150 mg per day, about 20 mg to about 80 mg per day, or about 1 mg to about 30 mg per day. In still other embodiments, the therapeutic biologic may be administered at a dose of about 1,300 mg/day, about 900 mg/day, about 600 mg/day, about 350 mg/day, about 300 mg/day, about 250 mg/day, about 200 mg/day, about 150 mg/day, about 80 mg/day, about 75 mg/day, about 60 mg/day, about 40 mg/day, about 30 mg/day, about 20 mg/day, about 15 mg/day, about 10 mg/day, about 5 mg/day, or about 2.5 mg/day. In some embodiments, the therapeutic biologic is administered at a dose of about 10 g to about 1000 mg per day.

In other embodiments, daily doses measured in terms of therapeutic biologic will be, for human subjects, of about 0.01 mg/kg per day to about 1500 mg/kg per day. Dosage may be adjusted appropriately to achieve desired drug levels, local or systemic, depending upon the administration. For example, it is expected that subcutaneous administration would be from one order to several orders of magnitude higher dose per day compared to IV infusion. In the event that the response in a subject is insufficient at such doses, even higher doses (or effective higher doses by a more localized delivery route) may be employed to the extent that patient tolerance permits. Multiple doses per day may be contemplated to achieve appropriate systemic levels of therapeutic biologics.

For any therapeutic biologic composition described herein, the therapeutically effective amount can be initially determined from animal models. A therapeutically effective dose can also be determined from human data for therapeutic biologics of the disclosure which have been tested in humans and for therapeutic biologics which are known to exhibit similar pharmacological activities, such as other related active agents. Higher doses may be required for parenteral administration. The applied dose can be adjusted based on the relative bioavailability and potency of the administered therapeutic biologic. Adjusting the dose to achieve maximal efficacy based on the compositions and methods described above and other methods as are well-known in the art and is well within the capabilities of the ordinarily skilled artisan.

To aid dissolution of the therapeutic biologic into the aqueous environment, a surfactant might be added as an additive. Surfactants may include anionic detergents such as sodium lauryl sulfate, dioctyl sodium sulfosuccinate or dioctyl sodium sulfonate. Cationic detergents which can be used and can include benzalkonium chloride or benzethonium chloride. Potential non-ionic detergents that could be included in the compositions as surfactants include lauro-macrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose or carboxymethyl cellulose. These surfactants could be present in the composition of the therapeutic biologic of the disclosure or derivative either alone or as a mixture in different ratios.

This disclosure includes the use of pharmaceutically acceptable salts of therapeutic biologics in the methods of the present disclosure. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, or other acids. In some embodiments, pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of a therapeutic biologic. As another example, the salt may comprise less than one inorganic or organic acid molecule per molecule of base, such as two molecules of a therapeutic biologic per molecule of tartaric acid.

In certain embodiments, contemplated salts of the disclosure include, but are not limited to, arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, L-lysine, magnesium, 4-(2-hydroxy ethyl)morpholine, piperazine, potassium, 1-(2-hydroxyethyl)pyrrolidine, sodium, triethanolamine, tromethamine, or zinc salts. In other embodiments, contemplated salts of the disclosure include, but are not limited to, Na, Ca, K, Mg, Zn or other metal salts. In further embodiments, contemplated salts of the disclosure include, but are not limited to, alkyl, dialkyl, trialkyl or tetra-alkyl ammonium salts. The pharmaceutically acceptable salts can also exist as various solvates, such as with water, methanol, ethanol, dimethylformamide, or the like. Mixtures of such solvates can also be prepared. The source of such solvate can be from the solvent of crystallization, inherent in the solvent of preparation or crystallization, or adventitious to such solvent.

In still other embodiments, the proteinaceous compositions may be formulated into a neutral or salt form. Pharmaceutically acceptable salts, include acid addition salts (formed with the free amino groups of the protein) and which are formed with inorganic acids such as, for example, hydrochloric or phosphoric acids, or such organic acids as acetic, oxalic, tartaric, mandelic, or the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine or the like.

As one of skill in the art will appreciate, compositions of the present disclosure, not having adverse effects upon administration to a subject, may be administered daily to the subject.

Preferred embodiments of this disclosure are described herein. Of course, variations, changes, modifications and substitution of equivalents of those preferred embodiments will become apparent to those of ordinary skill in the art upon reading the foregoing description. The inventors expect skilled artisans to employ such variations, changes, modifications and substitution of equivalents as appropriate, and the inventors intend for the disclosure to be practiced otherwise than specifically described herein. Those skilled in the art will readily recognize a variety of non-critical parameters that could be changed, altered or modified to yield essentially similar results. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

While each of the elements of the present disclosure is described herein as containing multiple embodiments. It should be understood that unless indicated otherwise, each of the embodiments of a given element of the present disclosure is capable of being used with each of the embodiments of the other elements of the present disclosure and each such use is intended to form a distinct embodiment of the present disclosure.

It will be understood by one of ordinary skill in the relevant arts that other suitable modifications and adaptations to the compositions and methods described herein are readily apparent from the description of the disclosure contained herein in view of information known to the ordinarily skilled artisan, and may be made without departing from the scope of the disclosure or any embodiment thereof.

Definitions

For purposes of the present disclosure, the following definitions will be used unless expressly stated otherwise:

The terms "a", "an", "the" and similar referents used in the context of describing the present disclosure are to be construed to cover both the singular and the plural, unless otherwise indicated herein or clearly contradicted by context. All compositions and methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of the disclosure otherwise claimed. No language in the present specification should be construed as indicating any unclaimed element is essential to the practice of the disclosure.

The term "about" in relation to a given numerical value, such as for temperature and period of time, is meant to include numerical values within 10% of the specified value.

As used herein, the term "administering" means the actual physical introduction of a composition into or onto (as appropriate) a subject. Any and all methods of introducing the composition into subject are contemplated according to the disclosure; the method is not dependent on any particular means of introduction and is not to be so construed. Means of introduction are known to those skilled in the art, and are also exemplified herein.

As used herein, an "amino acid" or "residue" refers to any naturally or non-naturally occurring amino acid, any amino acid derivative or any amino acid mimic known in the art. Included are the L- as well as the D-forms of the respective amino acids, although the L-forms are usually preferred. In some embodiments, the term relates to any one of the 20 naturally occurring amino acids: glycine (Gly), alanine (Ala), valine (Val), leucine (Leu), isoleucine (Ile), proline (Pro), cysteine (Cys), methionine (Met), serine (Ser), threonine (Thr), glutamine (Gin), asparagine (Asn), glutamic acid (Glu), aspartic acid (Asp), lysine (Lys), histidine (His), arginine (Arg), phenylalanine (Phe), tryptophan (Trp), and tyrosine (Tyr) in their L-form. In certain embodiments, the amino acid side-chain may be a side-chain of Gly, Ala, Val, Leu, Ile, Met, Cys, Ser, Thr, Trp, Phe, Lys, Arg, His, Tyr, Asn, Gln, Asp, Glu, or Pro.

As used herein, except where the context requires otherwise, the term "comprise" and variations of the term, such as "comprising", "comprises" and "comprised", are not intended to exclude further additives, components, integers or steps. The terms "including" and "comprising" may be used interchangeably. As used herein, the phrases "selected from the group consisting of," "chosen from," and the like, include mixtures of the specified materials. Where a numerical limit or range is stated herein, the endpoints are included. Also, all values and subranges within a numerical limit or range are specifically included as if explicitly written out. References to an element in the singular is not intended to mean "one and only one" unless specifically stated, but rather "one or more." Unless specifically stated otherwise, terms such as "some" refer to one or more, and singular terms such as "a," "an" and "the" refer to one or more.

As used herein, the terms "effective amount", "effective dose", "sufficient amount", "amount effective to", "therapeutically effective amount", "pharmaceutically effective amount" or grammatical equivalents thereof mean a dosage sufficient to produce a desired result, to ameliorate, or in some manner, reduce a symptom or stop or reverse progression of a condition and provide either a subjective relief of a symptom(s) or an objectively identifiable improvement as noted by a clinician or other qualified observer. Amelioration of a symptom of a particular condition by administration of a pharmaceutical composition described herein refers to any lessening, whether permanent or temporary, lasting, or transitory, that can be associated with the administration of the pharmaceutical composition. As stated above, an "effective amount" refers to any amount that is sufficient to achieve a desired biological effect. Combined with the teachings provided herein, by choosing among the various active therapeutic biologics and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular therapeutic biologic of the disclosure being administered, the size of the subject, or the severity of the disease or condition. One of ordinary skill in the art can empirically determine the effective amount of a particular therapeutic biologic of the disclosure and/or other therapeutic agent without necessitating undue experimentation. It is preferred generally that a maximum dose be used, that is, the highest safe dose according to some medical judgment. Multiple doses per day may be contemplated to achieve appropriate systemic levels of therapeutic biologics. Appropriate systemic levels can be determined by, for example, measurement of the patient's peak or sustained plasma level of the drug. "Dose" and "dosage" are used interchangeably herein. The term "dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise about 1 μg/kg/body weight to about 1000 mg/kg/body weight (this such range includes intervening doses) or more per administration, and any range derivable therein. In non-limiting examples of a derivable range from the numbers listed herein, a range of about 5 μg/kg/body weight to about 100 mg/kg/body weight, about 5 μg/kg/body weight to about 500 mg/kg/body weight, etc., can be administered. The practitioner responsible for administration will, in any event, determine the concentration of active ingredient(s) in a composition and appropriate dose(s) for the individual subject.

The term "oligopeptide" is used to refer to a peptide with fewer members of amino acids as opposed to a polypeptide or protein. Oligopeptides described herein, are typically comprised of about two to about forty amino acid residues. Oligopeptides include dipeptides (two amino acids), tripeptides (three amino acids), tetrapeptides (four amino acids), pentapeptides (five amino acids), hexapeptides (six amino acids), heptapeptides (seven amino acids), octapeptides (eight amino acids), nonapeptides (nine amino acids), decapeptides (ten amino acids), undecapeptides (eleven amino acids), dodecapeptides (twelve amino acids), icosapeptides (twenty amino acids), tricontapeptides (thirty amino acids), tetracontapeptides (forty amino acids), etc. Oligopeptides may also be classified according to molecular structure: aeruginosins, cyanopeptolins, microcystins, microviridins, microginins, anabaenopeptins and cyclamides, etc. Homo-oligopeptides are oligopeptides comprising the same amino acid. In preferred embodiments, homo-oligopeptides comprise 10 amino acid poly-valine, poly-alanine, and poly-glycine hexamers.

The meaning of the term "peptides" are defined as small proteins of two or more amino acids linked by the carboxyl group of one to the amino group of another. Accordingly, at its basic level, peptide synthesis of whatever type comprises the repeated steps of adding amino acid or peptide molecules to one another or to an existing peptide chain. The term "peptide" generally has about 2 to about 100 amino acids, whereas a polypeptide or protein has about 100 or more amino acids, up to a full length sequence which may be translated from a gene. Additionally, as used herein, a peptide can be a subsequence or a portion of a polypeptide or protein. In certain embodiments, the peptide consists of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues. In preferred embodiments, the peptide is about 30 to about 100 amino acids in length. In some embodiments, the peptide is about 40 to about 100 amino acids in length.

As used herein, the term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a federal or state government or listed in the U.S. Pharmacopeia or other generally recognized pharmacopeia for use in animals, and more particularly in humans.

As used herein, a therapeutic that "prevents" a disorder or condition refers to a therapeutic biologic that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the term "prodrug" is intended to encompass therapeutic biologics which, under physiologic conditions, are converted into the therapeutically active biologics of the present disclosure. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates, e.g., esters or carbonates of alcohols or carboxylic acids, are preferred prodrugs of the present disclosure. In certain embodiments, some or all of the molecules in a composition represented above can be replaced with the corresponding suitable prodrug, e.g., wherein a hydroxyl in the parent molecule is presented as an ester or a carbonate or carboxylic acid present in the parent therapeutic biologic is presented as an ester.

The meaning of the term "protein" is defined as a linear polymer of about 20 different amino acids. The type and the sequence of amino acids in a protein are specified by the DNA that produces them. In certain embodiments, the sequences can be natural and unnatural. The sequence of amino acids determines the overall structure and function of a protein. In some embodiments, proteins can contain 50 or more residues. In preferred embodiments, proteins can contain greater than about 101 residues in length. A protein's net charge can be determined by two factors: 1) the total count of acidic amino acids vs. basic amino acids; and 2) the specific solvent pH surroundings, which expose positive or negative residues. As used herein, "net positively or net negatively charged proteins" are proteins that, under non-denaturing pH surroundings, have a net positive or net negative electric charge. In general, those skilled in the art will recognize that all proteins may be considered "net negatively charged proteins", regardless of their amino acid composition, depending on their pH and/or solvent surroundings. For example, different solvents can expose negative or positive side chains depending on the solvent pH. Proteins or peptides are preferably selected from any type of enzyme or antibodies or fragments thereof showing substantially the same activity as the corresponding enzyme or antibody. Proteins or peptides may serve as a structural material, e.g. keratin, as enzymes, as hormones, as transporters, e.g. hemoglobin, as antibodies, or as regulators of gene expression. Proteins or peptides are required for the structure, function and regulation of cells, tissues and organs.

The term "substantially free of" as used herein, refers to a majority of, or mostly, as in at least about 51%, 60%, 70%, 80%, 90%, 95%, 96%, 97%, 98%, 99%, 99.5%, 99.9%, 99.99%, or at least about 99.999% or more.

The term "treating" is art-recognized and includes administration to the host of one or more of the subject compositions, e.g., to diminish, ameliorate, or stabilize the existing unwanted condition or side effects thereof.

It is understood that the specific order or hierarchy of steps in the methods or processes disclosed is an illustration of exemplary approaches. Based upon design preferences, it is understood that the specific order or hierarchy of steps in the methods or processes may be rearranged. Some of the steps may be performed simultaneously. Other steps may be performed continuously or intermittently with on/off time periods, e.g., occurring at regular or irregular intervals, and the duration of the time periods and/or the ration between them may be changed in either a structured or unstructured manner. The accompanying methods claims present elements of the various steps in a sample order, and are not meant to be limited to a specific hierarchy or order presented. A phrase such as "embodiment" does not imply that such embodiment applies to all configurations of the subject technology. A disclosure relating to an embodiment may apply to all embodiments, or one or more embodiments. A phrase such as an embodiment may refer to one or more embodiments and vice-versa.

Methods of the Disclosure

Where a clinical application of a therapeutic composition comprising a therapeutic biologic, e.g., mAb, is undertaken, it will generally be beneficial to prepare a pharmaceutical or therapeutic composition that is appropriate for the intended application. In certain embodiments, pharmaceutical compositions may comprise, for example, at least about 0.1% of an active therapeutic biologic. In other embodiments, an active therapeutic biologic may comprise about 2% to about 99% of the weight of the unit, or about 50% to about 99%, for example, and any range derivable therein.

With large molecule biologics, e.g., mAbs, protein instability and high viscosities can result from intermolecular interactions in solution. High viscosities can make it difficult to handle and inject the drug composition. Protein instability can reduce the effective dose as less of the protein than therapeutically useful and can form aggregates which may harm the patient.

As described herein, microparticle-based compositions or suspension formulations can directly address the current challenges of subcutaneous therapeutic biologic, e.g., mAb, protein, delivery by enabling high concentrations (>400 mg/mL) of therapeutic biologic, while maintaining an injectable, e.g., syringeable format with excellent mAb or protein stability. The terms "particle" and "microparticle" are used herein interchangeably in the broadest sense. In some embodiments, the solid microparticles limit the intermolecular interactions responsible for high viscosities and instabilities in aqueous compositions. In other embodiments, the particles are suspended in a liquid carrier vehicle to prevent dissolution until injection. The compositions described herein can be filled in a prefilled syringe or injection device format, e.g., needle-free injection, eliminating the need for complex, error-prone reconstitution procedures. The highly dispersible nature of the particles in the composition that are described herein, enables easy resuspension by gentle shaking, allowing for a patient-friendly subcutaneous injection. Within the subcutaneous space, the therapeutic biologic comprising the particles described herein, readily return to their original monomeric state upon injection, enabling full bioavailability. In preferred embodiments, the compositions do not compromise the therapeutic biologic quality and achieve higher loading, thus, allowing the therapeutic biologic, e.g., mAbs, to be delivered in a prefilled syringe by subcutaneous injection.

Provided herein are compositions and methods useful for treating a disease or condition in a subject in need thereof, comprising administering to the subject a pharmaceutically effective amount of a composition comprising: a plurality of particles suspended in a low viscosity pharmaceutically acceptable liquid carrier, each particle comprising at least one therapeutic biologic or a salt thereof; wherein the particles have less than about 10% aggregation of the therapeutic biologic; and the concentration of the therapeutic biologic in the composition is about 20 mg/mL to about 700 mg/mL.

In some embodiments, the disease or condition is cancer. In other embodiments, the disease or condition is inflammatory disease or condition. In certain embodiments, the disease or condition is an immune disease. In certain other embodiments, the disease or condition is renal disease. In still other embodiments, the disease or condition is a skin disease or condition. In yet other embodiments, the disease or condition is a human immuno deficiency virus (HIV) infection.

Viscosity can play an important role in the handling and administration of injectable products. For suspension products, high viscosities can prevent settling of the suspension, however, the drug product may be difficult to deliver through a 27-gauge needle since it takes greater force to actuate the injection device, e.g., syringe. Alternatively, using a wider needle or requiring longer injection times can reduce patient compliance to therapy.

Particle size and dispersity also impacts injectability, e.g., syringeability. Particles are often recommended to be at least 3-10 times smaller than the inner diameter of the needle. Even if a small fraction of the particle population is larger than the inner diameter of the needle, they may clog the needle and cause the entire dosage to go to waste. As described herein, the plurality of particles comprising at least one therapeutic biologic in suspension can achieve lower viscosities at higher concentrations. In some embodiments, the plurality of particles as described herein, can achieve protein loadings greater than 90% while maintaining stability of the protein. The compositions described herein, comprises therapeutic biologic concentrations of about 400 mg/mL below about 100 mPa·s, enabling subcutaneous delivery of therapeutic biologic, e.g., protein, mAb, drug compositions without compromising structure and functional bioactivity.

The particles described herein are discrete, spheroidal, and of controlled dispersity with a characteristic size from sub-micrometers to tens of micrometers, in contrast to, e.g., a porous monolithic "cake", which is typically produced during conventional lyophilization. This morphology typically allows for a flowable powder (as described by low Hausner ratios) without post-processing.

In some embodiments, the particles have diameters of about 0.1 to about 1000 μm, e.g., about 1 to about 400 μm, about 1 to about 200 μm, about 1 to about 100 μm, about 1 to about 50 μm, about 1 to about 25 μm, about 1 to about 10 μm, about 10 to about 100 μm, about 50 to about 100 μm, about 50 to about 75 μm, or about 75 to about 100 μm. In other embodiments, the particles have diameters of about 1 to about 100 μm, e.g., about 4 to about 100 μm, about 10 to about 100 μm, or about 20 to about 50 μm.

In certain embodiments, the particles may include one or more agents, e.g., therapeutic biologic. In other embodiments, the particles can have diameters of about 0.1 to about 1000 μm, e.g., about 0.1 to about 90 μm, about 90 to about 230 μm, or about 0.1 to about 1 μm. In still other embodiments, the particles can have a size dispersity of about 0 to about 0.9, e.g., about 0 to about 0.7, of about 0 to about 0.5, or of about 0 to about 0.2. Methods of measuring the particle size and distribution include imaging flow cytometry and image analysis of scanning electron micrographs of the particles in which an average spherical radius or diameter can be calculated on the basis of the cross-sectional areas of the particles projected onto the plane of the image.

In some embodiments, the sphericity of the particles may range about 0.1 to about 1, e.g., at least about 0.2, about 0.4, about 0.6, or about 0.8. Methods of measuring particle sphericity include image analysis of scanning electron micrographs of the particles in which the average roundness is calculated on the basis of the cross-sectional shapes of the particles projected onto the plane of the image. Such roundness factors can be extended to identify the corresponding sphericity.

In other embodiments, the particles have less than about 20% aggregation or less than about 20% fragmentation of the therapeutic biologic, e.g., less than about 19, 18, 17, 16, 15, 14, 13, 12, 10, 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1%. In some embodiments, the particles have less than about 10% aggregation or less than about 10% fragmentation of the therapeutic biologic, e.g., less than about 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1%. In certain embodiments, the particles have about 3% to about 1% aggregation of the therapeutic biologic. In certain other embodiments, the particles have about 1% to about 0.5% aggregation of the therapeutic biologic. In preferred embodiments, the particles are substantially free from any aggregation of the therapeutic biologic. In still other embodiments, the particles are substantially free from any fragmentation of the therapeutic biologic. Suitable methods for measuring aggregation and fragmentation of a biologic can be accomplished by using size-exclusion chromatography (SEC).

In some embodiments, the process of particle formation provides less than about 50% change in charge variants in the population of a therapeutic biologic, e.g., an antibody or an antibody fragment, (e.g., less than about 40, 30, 20, 10, 8, 5, 4, 3, or 1%) as compared to the therapeutic biologic prior to particle formation. Charge variants may be acidic, basic, or neutral, and the variation may be caused post-translation modifications at terminal amino acids, such as asparagine deamidation or lysine glycation. For example, charge variants include the loss of a positive charge by the loss of a C-terminal lysine residue, covalent bonding of the amine portions of two lysine residues by reducing sugars, or the conversion of an N-terminal amine to a neutral amide by the cyclization of N-terminal glutamines. Negative charges on proteins, e.g., antibodies, can appear by the conversion of asparagine residues to aspartic acid and/or isoaspartic residues via a deamidation reaction.

Exemplary methods of measuring charge variants include cation exchange chromatography (CIEX), where the variants are quantified by dividing the area under the peak corresponding to the variant, e.g., acidic, basic, or neutral population by the cumulative area contained beneath all peaks in the sample spectrum. Changes in charge variant population percentage between two samples, e.g., Sample A and Sample B, are computed as the numerical difference in the respective population variant percentages, i.e., by subtracting the specific variant, e.g., acidic, percentage of Sample B from the specific variant, e.g., acidic, percentage of Sample A, or vice versa. In certain embodiments, the analysis may be extended similarly for all variants within a population.

In certain embodiments, the particle has less than about 50% change in charge variants of the therapeutic biologic, e.g., less than about 45, 40, 35, 30, 25, 20, 15, 10, 9, 8, 7, 6, 5, 4, 3, 2, 1, 0.5, 0.1%, compared to the starting therapeutic biologic prior to particle formation. In preferred embodiments, the particle is substantially free from any change in charge variants of the therapeutic biologic compared to the starting therapeutic biologic prior to particle formation. Suitable methods for measuring a change in charge variants of a therapeutic biologic can be accomplished by using cation exchange chromatography (CIEX).

The particles according to the disclosure are circular. Circularity can serve as an indicator of the shape of the particle. The particles described herein, can have a characteristic circularity, e.g., have a relative shape, that is substantially circular. This characteristic describes and defines the form of a particle on the basis of its circularity. The circularity is 1.0 when the particle has a completely circular structure. Particles as described herein, can have a circularity of about 0.8, 0.85, 0.9, 0.95, 0.96, 0.97, 0.98, or about 0.99. The diameter and the circularity of the particles can be determined by the image processing of an image observed under an electron microscope or the like or a flow-type particle image analyzer. The circularity can also be determined by subjecting particles to circularity measurement and averaging the resulting values. For example, circularity (circ) can be calculated using the following formula:

$$circ = 4 * \pi * \frac{\text{Area}}{\text{Perimeter}^2}. \qquad \text{Eq. 1}$$

The term "perimeter", as used herein, refers to the boundary of a closed plane figure or the sum of all borders of a two-dimensional image. As used herein, the term "area", refers to the crossectional area of a two-dimensional image of a particle. The circularity of a particle can also be described as the ratio of the smallest diameter of the particle to its largest diameter. For a perfect circle, the ratio is 1. The percentage circularity can be calculated by multiplying the circularity by 100. The circularity can be calculated, for example, by measuring the aspect ratio using any software adapted to deal with images, for example, images obtained by microscopy, in particular, scanning electron microscopy (SEM) or transmission electron microscopy (TEM). In some embodiments, the particles have a circularity of about 0.10 to about 1.00, e.g., about 0.20, 0.30, 0.40, 0.50. 0.60, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99 to about 1.00. In other embodiments, the particles have a circularity of about 0.80 to about 1.00. In still other embodiments, the particles have a circularity of about 0.85 to about 1.00. In certain other embodiments, the particles have a circularity of about 0.90 to about 1.00. In certain embodiments, the particles have a circularity of about 0.95 to about 1.00. In certain preferred embodiments, the particles have a circularity of about 0.98 to about 1.00. In preferred embodiments, the particles have a circularity of about 1.00. In some embodiments, methods of measuring particle circularity include image analysis of scanning electron micrographs of the particles in which the average roundness is calculated on the basis of the cross-sectional shapes of the particles projected onto the plane of the image. Such roundness factors can be extended to identify the corresponding circularity.

In other embodiments, the residual moisture and/or solvent content of the dry component is less than about 7% by weight, e.g., less than about 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% by weight. In some embodiments, the particles have less than about 7% residual moisture by weight. In still other embodiments, the particles have less than about 5% residual moisture by weight. In certain embodiments, the particles have less than about 3% residual moisture by weight. In preferred embodiments, the particles have less than about 1% residual moisture by weight.

In some embodiments, the particles have about 7% to about 1% residual moisture by weight. In still other embodiments, the particles have about 5% to about 1% residual moisture by weight. In preferred embodiments, the particles have about 3% to about 1% residual moisture by weight. In certain preferred embodiments, the particles are substantially free from any residual moisture by weight.

Exemplary methods for the measurement of moisture content include chemical titration methods, e.g., Karl Fischer titration involving an oven. A variety of solvents, including water, may also be measured using weight loss methods involving thermal excitation. Exemplary methods include Thermogravimetric Analysis with Infrared Spectroscopy (TGA-IR) or Gas Chromatography Flame Ionization Detector Gas Chromatography (GC-FID/MS).

In some embodiments, the particles have less than about 50% internal void spaces, e.g., less than about 45, 40, 35, 30, 25, 20, 15, 10, 9, 8, 7, 6, 5, 4, 3, 2, 1, 0.5, 0.1%. In certain embodiments, the particles may include less than 25% internal void spaces, less than 10% internal void spaces, less than 5% internal void spaces, less than 3% internal void spaces, less than 1% internal void spaces, or less than 0.1% internal void spaces. In preferred embodiments, the particles are substantially free from any internal void spaces. Suitable methods for determining internal void space can be accomplished by using Focused Ion Beam Scanning Electron Microscopy (FIB-SEM), which can be used to visualize "accessible" and "inaccessible" void spaces, or gas displacement pycnometry (Micromeritics Instrument Corporation of Norcross, Ga.), which can determine "accessible" voids (void spaces accessible from the surface rather than those resembling a core-shell structure that are "unaccessible form the surface"). Gas pycnometry is a common analytical technique that uses a gas displacement method to measure volume. Inert gases, such as helium or nitrogen, are used as the displacement medium. True volume is total volume minus volume accessible to the gas. Density is calculated by dividing sample weight with true volume. The sample is sealed in the instrument compartment of a known volume, the appropriate inert gas is admitted, and then expanded into another precision internal volume. The pressure before and after expansion is measured and used to compute the sample volume. Dividing this volume into the sample weight gives the gas displacement density. Cross-sections of typical particles of the disclosure indicate an absence of pores (substantially free from any internal void spaces) and low particle porosity as shown by FIB-SEM or by gas pycnometry using helium at temperatures at about 22° C. to provide densities typically averaging about 1.3 g/cm³ with standard deviations at about 0.0005 g/cm³.

In other embodiments, the particles exhibit a skeletal density of about 1 to about 6 g/cm³, e.g., about 1 to about 5 g/cm³, about 1 to about 3 g/cm³, about 1 to about 2 g/cm³, about 1 to about 1.5 g/cm³, or about 1.1 to about 1.4 g/cm³. Exemplary methods of skeletal density measurements include gas displacement pycnometry. In certain embodiments, the particles exhibit a density of about 0.1 to about 5 g/cm³, e.g., about 0.1 to about 2.5 g/cm³, about 0.1 to about 1.4 g/cm³, about 0.5 to about 1.4 g/cm³, or about 1.0 to about 1.4 g/cm³. In certain embodiments, the particles have a density of about 1000 mg/mL to about 1500 mg/mL, about 1050 mg/mL to about 1500 mg/mL, about 1100 mg/mL to about 1500 mg/mL, about 1150 mg/mL to about 1500 mg/mL, about 1200 mg/mL to about 1500 mg/mL, about 1250 mg/mL to about 1500 mg/mL, about 1300 mg/mL to about 1500 mg/mL, about 1310 mg/mL to about 1500 mg/mL, about 1320 mg/mL to about 1500 mg/mL, about 1330 mg/mL to about 1500 mg/mL, about 1340 mg/mL to about 1500 mg/mL, about 1350 mg/mL to about 1500 mg/mL, about 1360 mg/mL to about 1500 mg/mL, about 1370 mg/mL to about 1500 mg/mL, about 1380 mg/mL to about 1500 mg/mL, about 1390 mg/mL to about 1500 mg/mL, about 1400 mg/mL to about 1500 mg/mL, about 1410 mg/mL to about 1500 mg/mL, about 1420 mg/mL to about 1500 mg/mL, about 1430 mg/mL to about 1500 mg/mL, about 1440 mg/mL to about 1500 mg/mL, about 1450 mg/mL to about 1500 mg/mL, about 1460 mg/mL to about 1500 mg/mL, about 1470 mg/mL to about 1500 mg/mL, about 1480 mg/mL to about 1500 mg/mL, or about 1490 mg/mL to about 1500 mg/mL. In preferred embodiments, the particles have a density of about 1000 mg/mL to about 1500 mg/mL, about 1300 mg/mL to about 1500 mg/mL, or about 1320 mg/mL to about 1500 mg/mL.

In some embodiments, the particles have greater than about 60% therapeutic biologic by weight, e.g., greater than about 65, 70, 75, 80, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% therapeutic biologic by weight.

In some embodiments, the particles further comprise a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, a nutrient media, or a combination thereof. In certain embodiments, the particles further comprise a carbohydrate, a pH adjusting agent, a salt, a surfactant, a protein stabilizer, an emulsifier, an amino acid, or a combination thereof.

In other embodiments, the carbohydrate may be from the families of monosaccharides, disaccharides, oligosaccharides, or polysaccharides. In some embodiments, the carbohydrate is dextran, trehalose, sucrose, agarose, mannitol, lactose, sorbitol, maltose, starch, alginates, xanthan, galactomanin, agar, agarose, or a combination thereof. In certain embodiments, the carbohydrate is dextran, trehalose, sucrose, agarose, mannitol, lactose, sorbitol, maltose, or a combination thereof. In preferred embodiments, the carbohydrate is trehalose, cyclodextrins, hydroxypropyl beta-cyclodextrin, sulfobutylether beta-cyclodextrin, or a combination thereof. Cyclodextrins are available in three different forms α, β, and γ based on the number of number of glucose monomers. The number of glucose monomers in α, β, and γ cyclodextrin can be 6, 7, or 8, respectively.

In some embodiments, the pH adjusting agent is acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, monosodium glutamate, sodium hydroxide, potassium hydroxide, or a combination thereof. In other embodiments, the pH adjusting agent is citrate, histidine, phosphate, succinate, sodium hydroxide, potassium hydroxide, or a combination thereof. In certain embodiments, the pH adjusting agent is hydrochloric acid or citric acid.

In other embodiments, the salt is sodium chloride, calcium chloride, potassium chloride, sodium hydroxide, stannous chloride, magnesium sulfate, sodium glucoheptonate, sodium pertechnetate, guanidine hydrochloride, potassium hydroxide, magnesium chloride, potassium nitrate, or a combination thereof. In preferred embodiments, the salt is sodium chloride.

In some embodiments, the chelator is disodium edetate, ethylenediaminetetraacetic acid, pentetic acid, or a combination thereof. In other embodiments, the mineral is calcium, zinc, titanium dioxide, or a combination thereof. In certain embodiments, the polymer is propyleneglycol, glucose star polymer, silicone polymer, polydimethylsiloxane, polyethylene glycol, carboxymethylcellulose, poly(glycolic acid), poly(lactic-co-glycolic acid), polylactic acid, polycaprolactone (PCL), polyvinylpyrrolidone (PVP), ficoll, dextran, or a combination thereof.

In other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, Aerosol-OT (sodium bis(2-ethylhexyl) sulfosuccinate), sodium laureth sulfate, lecithin, sorbitan esters, or a combination thereof. In some embodiments, the surfactant includes, but is not limited to: (i) cationic surfactants such as; cetyltrimethylammonium chloride, hexadecyltrimethylammonium chloride, benzalkonium chloride, benzethonium chloride, dioctadecyldimethylammonium bromide; (ii) anionic surfactants such as magnesium stearate, sodium dodecyl sulfate, dioctyl sodium sulfosuccinate, sodium myreth sulfate, perfluorooctanesulfonate, alkyl ether phosphates; (iii) non-ionic surfactants such as alkylphenol ethoxylates (TritonX-100), fatty alcohol ethoxylates (octaethylene glycol monododecyl ether, cocamide diethanolamine, poloxamers, glycerolmonostearate, fatty acid esters of sorbitol (sorbitan monolaurate, Tween 80, Tween 20; and (iv) zwitterionic surfactants such as cocamidopropyl hydroxysultaine, and 3-[(3-Cholamidopropyl)dimethylammonio]-1-propanesulfonate (CHAPS). In certain embodiments, the surfactant is polysorbate, docusate, lecithin or sorbitan esters. In preferred embodiments, the surfactant is sorbitan esters, polysorbate 20, polysorbate 60, or polysorbate 80. In certain preferred embodiments, the surfactant is sorbitan esters, polysorbate 20 or polysorbate 80. In certain other embodiments, the fatty acid ester of sorbitol is a sorbitan ester, e.g., span 20, span 40, span 60, span 80, span 85, or the like.

In some embodiments, the protein stabilizer is acetyltryptophanate, caprylate, N-acetyltryptophan, trehalose, polyethylene glycol (PEG), polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, mannitol, or a combination thereof. In certain embodiments, the protein stabilizer is trehalose, polyethylene glycol (PEG), polyoxamers, polyvinylpyrrolidone, polyacrylic acids, poly(vinyl) polymers, polyesters, polyaldehydes, tert-polymers, polyamino acids, hydroxyethyl starch, N-methyl-2-pyrrolidone, sorbitol, sucrose, mannitol, cyclodextrin, saccharides, hydroxypropyl beta-cyclodextrin, sulfobutylether beta-cyclodextrin, or a combination thereof. In preferred embodiments, the protein stabilizer is trehalose, cyclodextrin, hydroxypropyl beta-cyclodextrin, sulfobutylether beta-cyclodextrin, or a combination thereof. The stabilizers, used synonymously with the term "protein stabilizer" or "stabilizing agent", as described herein, can be a salt, a carbohydrate, saccharides or amino acids, preferably a carbohydrate or saccharide admitted by the authorities as a suitable additive or excipient in pharmaceutical compositions. In preferred embodiments, the PEG is PEG 200, PEG 300, PEG 3350, PEG 8000, PEG 10000, PEG 20000, or a combination thereof.

Examples of emulsifiers suitable for use in the particles include, but are not limited to, lipophilic agents having an HLB of less than 7, such as mixed fatty acid monoglycerides; mixed fatty acid diglycerides; mixtures of fatty acid mono- and diglycerides; lipophilic polyglycerol esters; glycerol esters including glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; or a combination thereof. In some embodiments, the emulsifier is polysorbate 80, polysorbate 60, polysorbate 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, a poloxamer, or a combination thereof. In preferred embodiments, the fatty acid ester of sorbitol is a sorbitan ester, e.g., span 20, span 40, span 60, span 80, span 85, or the like. In certain preferred embodiments, the emulsifier is polysorbate 80, sorbitan monooleate, or a combination thereof.

In other embodiments, the antiseptic is phenol, m-cresol, benzyl alcohol, 2-phenyloxyethanol, chlorobutanol, neomycin, benzethonium chloride, gluteraldehyde, beta-propiolactone, or a combination thereof.

In certain embodiments, the amino acid is alanine, aspartic acid, cysteine, isoleucine, glutamic acid, leucine, methionine, phenylalanine, pyrrolysine, serine, selenocysteine, threonine, tryptophan, tyrosine, valine, asparagine, arginine, histidine, glycine, glutamine, proline, or a combination thereof. In preferred embodiments, the amino acid is arginine, histidine, proline, asparagine, or a combination thereof.

In some embodiments, the antioxidant is glutathione, ascorbic acid, cysteine, N-acetyl-L-tryptophanate, tocopherol, histidine, methionine, or a combination thereof. In other embodiments, the protein is protamine, protamine sulfate, gelatin, or a combination thereof. In certain embodiments, the organic solvent is dimethyl sulfoxide, N-methyl-2-pyrrolidone, or a combination thereof. In still other embodiments, the preservative is methyl hydroxybenzoate, thimerosal, a paraben, formaldehyde, castor oil, or a combination thereof. The paraben can be a parahydroxybenzoate. In some embodiments, the bactericide is benzalkonium chloride (cationic surfactants), hypochlorites, peroxides, alcohols, phenolic compounds (e.g. carbolic acid), or a combination thereof.

In other embodiments, the fungicide is acibenzolar, 2-phenylphenol, anilazine, carvone, natamycin, potassium azide, or a combination thereof. In certain embodiments, the vitamin is thiamine, riboflavin, niacin, pantothenic acid, biotin, vitamin B6, vitamin B12, folate, niacin, ascorbic acid, calciferols, retinols, quinones, or a combination thereof. In still other embodiments, the preservative is sodium nitrate, sulfur dioxide, potassium sorbate, sodium sorbate, sodium benzoate, benzoic acid, methyl hydroxybenzoate, thimerosal, parabens, formaldehyde, castor oil, or a combination thereof.

A number of nutrient media, preferably serum free, alone or in combination, may be used in the present disclosure, including commercially available media or other media known in the art. Examples of such media (all without serum or having had the serum removed) include ADC-1, LPM (Bovine Serum Albumin-free), F10 (HAM), F12 (HAM), DCCM1, DCCM2, RPMI 1640, BGJ Medium (Fitton-Jackson Modification), Basal Medium Eagle (BME—with the addition of Earle's salt base), Dulbecco's Modified Eagle Medium (DMEM-without serum), Glasgow Modification Eagle Medium (GMEM), Leibovitz L-15 Medium, McCoy's 5 A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA—with non-essential amino acids), among numerous others. In addition, serum-containing nutrient media may also be used in compositions according to the present disclosure, but the use of serum-containing media is less preferred because of the possibility that the serum may be contaminated with microbial agents and because the patient may develop immunological reactions to certain antigenic components contained in the serum.

The plurality of particles comprising at least one therapeutic biologic described herein, can be prepared in a number of ways, as well as any methods of forming the particles disclosed in, for example, PCT/US2017/063150, PCT/US2018/043774, PCT/US2019/033875, PCT/US20/15957, U.S. 62/799,696, U.S. 62/899,907, U.S. 62/899,981, U.S. 62/978,641 and U.S. 63/011,820, each of which is hereby incorporated by reference in its entirety.

Particles of the disclosure can be suspended in an aqueous liquid carrier, non-aqueous liquid carrier, e.g., an organic liquid, an ionic liquid carrier, a gel carrier, or a combination thereof to form a suspension composition. The medium for suspension may further include, e.g., a carbohydrate, a pH adjusting agent, a salt, a chelator, a mineral, a polymer, a surfactant, an amino acid, an oligopeptide, a biologic excipient, a chemical excipient, an antiseptic, an antioxidant, a paraben, a bactericide, a fungicide, a vitamin, a preservative, an analgesic, and/or nutrient media. In some embodiments, each of the other components is, independently, at 0.0001 to 99% (w/v) of the medium, e.g., at 0.0001 to 90% (w/v), at 0.0001 to 50% (w/v), at 0.0001 to 10% (w/v), at 0.0001 to 1% (w/v), or at 0.0001 to 0.1% (w/v).

For aqueous or non-aqueous suspension compositions or formulations, high concentration trehalose solutions can be used to stabilize the particles in suspension and prevent premature dissolution. In certain instances, the sugar acts as a steric stabilizer if adsorbed onto the particle surface but if non-absorbing can also act as a "crowder" molecule. A crowder molecule may function by enhancing depletion repulsions. This stabilizing effect has also been described for other crowding agents such as (i) polymers, e.g., PEG 200, PEG 300, PEG 3350, PEG 8000, PEG 10000, PEG 20000, polyoxamers, polyvinylpyrrolidone, polyacrylic acids, poly (vinyl) polymers, polyesters, polyaldehydes, tert-polymers, polyamino acids, or hydroxyethylstarch, etc. (note that these may be used alone or in combination); (ii) organic molecules, e.g., N-methyl-2-pyrrolidone (Miller et al. J. Pharm. Sci., 2012, 101, 3763-3778), and (iii) sugars or sugar alcohols such as sorbitol, sucrose, and mannitol, among others. Other "crowding agents" include salts such as ammonium sulfate which can compete for water in hydration, and water soluble organic liquids such as N-methyl pyrrolidone (NMP) which can lower the solvent dielectric constant and produce excluded volume effects.

In some embodiments, the surfactant in the liquid carrier (either aqueous and non-aqueous) can act as a charge stabilizer. The surfactant adsorbs onto the surface of the particles to control electrostatic interactions between them. The repulsive electrostatic force generated upon the addition of surfactant to the composition is sufficient in certain embodiments to prevent significant aggregation of the particles. The surfactant can also prevent attachment to the container or vessel. In other embodiments, a polymer can be added to the liquid carrier, to act as a steric stabilizer.

The term "viscosity" is used to describe the property of a fluid acting to resist shearing flow. For the purposes of the present disclosure, viscosity can be determined using a rheometer, e.g., AR-G2 Rheometer (TA Instruments, USA), fitted with a cone and plate (2°/40 mm) at 25° C. at a specified shear rate. In certain embodiments, the viscosity is measured at a shear rate in the Newtonian regime. In other embodiments, the viscosity is measured at a shear rate of $100 \text{ s}^{-1}$ or greater, e.g., at $1000 \text{ s}^{-1}$ or greater than $1000 \text{ s}^{-1}$, or greater than $10,000 \text{ s}^{-1}$ or greater than $50,000 \text{ s}^{-1}$. The term "low viscosity" as used herein, describes a composition, e.g., a liquid carrier, having a viscosity of less than about 200 mPa·s.

In some embodiments, the composition has a viscosity of less than about 200 mPa·s, less than about 150 mPa·s, less than about 125 mPa·s, less than about 100 mPa·s, less than about 95 mPa·s, less than about 90 mPa·s, less than about 85 mPa·s, less than about 80 mPa·s, less than about 75 mPa·s, less than about 70 mPa·s, less than about 65 mPa·s, less than about 60 mPa·s, less than about 55 mPa·s, less than about 50 mPa·s, less than about 45 mPa·s, less than about 40 mPa·s, less than about 35 mPa·s, less than about 30 mPa·s, less than about 25 mPa·s, less than about 20 mPa·s, less than about 19 mPa·s, less than about 18 mPa·s, less than about 17 mPa·s, less than about 16 mPa·s, less than about 15 mPa·s, less than about 14 mPa·s, less than about 13 mPa·s, less than about 12 mPa·s, less than about 11 mPa·s, less than about 10 mPa·s, less than about 9.5 mPa·s, less than about 9 mPa·s, less than about 8.5 mPa·s, less than about 8 mPa·s, less than about 7.5 mPa·s, less than about 7 mPa·s, less than about 6.5 mPa·s, less than about 6 mPa·s, less than about 5.5 mPa·s, less than about 5 mPa·s, less than about 4.5 mPa·s, less than about 4 mPa·s, less than about 3.5 mPa·s, less than about 3 mPa·s, less than about 2.5 mPa·s, less than about 2 mPa·s, less than about 1.5 mPa·s, less than about 1 mPa·s, less than about 0.5 mPa·s, less than about 0.1 mPa·s, less than about 0.05 mPa·s, or less than about 0.01 mPa·s (one millipascal-second). In other embodiments, the composition has a viscosity of about 0.01 mPa·s to about 10,000 mPa·s, e.g., about 0.01 mPa·s to about 1,000 mPa·s, about 0.01 mPa·s to about 100 mPa·s, about 0.01 mPa·s to about 50 mPa·s, about 0.01 mPa·s to about 25 mPa·s, about 0.01 mPa·s to about 10 mPa·s, about 0.01 mPa·s to about 5 mPa·s, or about 0.01 mPa·s to about 1 mPa·s. In certain embodiments, the viscosity of the composition can range of about 0.27 mPa·s to about 200 mPa·s, e.g., about 0.27 mPa·s to about 50 mPa·s, about 1 mPa·s to about 30 mPa·s, or about 20 mPa·s to about 50 mPa·s. In still other embodiments, the viscosity of the composition ranges of about 0.27 mPa·s to about 200 mPa·s, e.g., about 0.27 mPa·s to about 100 mPa·s, about 0.27 mPa·s to about 50 mPa·s, about 0.27 mPa·s to about 30 mPa·s, about 1 mPa·s to about 20 mPa·s, or about 1 mPa·s to about 15 mPa·s. In certain embodiments, the viscosity is measured at a shear rate in the Newtonian regime. In other embodiments, the viscosity is measured at a shear rate of about 100 s-1 or greater, e.g., at about 1000 s-1 or greater than about 1000 s-1. The composition may include about 5 to about 90% particles by volume, e.g., e.g., about 20 to about 90%, about 40 to about 80%, about 50 to about 60%, or about 70 to about 90%. The composition may have a concentration of the therapeutic biologic of about 0.0001 to about 1000 mg/mL, e.g., about 100 to about 900, about 150 to about 800, or about 200 to about 700 mg/mL. Methods of controlling viscosity include temperature regulation and viscosity modifying additives. Mixtures of liquids may also be used to control viscosity. The units "mPa·s" and "cP" are used herein interchangeably in the broadest sense.

In other embodiments, the composition has a viscosity of less than about 200 mPa·s. In some embodiments, the composition has a viscosity of less than about 150 mPa·s. In certain embodiments, the composition has a viscosity of less than about 100 mPa·s. In still other embodiments, the composition has a viscosity of less than about 80 mPa·s. In certain other embodiments, the composition has a viscosity of less than about 50 mPa·s. In some embodiments, the composition has a viscosity of less than about 40 mPa·s. In other embodiments, the composition has a viscosity of less than about 30 mPa·s. In certain embodiments, the composition has a viscosity of less than about 20 mPa·s. In still other embodiments, the composition has a viscosity of less than about 10 mPa·s. In certain other embodiments, the composition has a viscosity of less than about 5 mPa·s. In some embodiments, the composition has a viscosity of less than about 3 mPa·s. In other embodiments, the composition has a viscosity of less than about 2.5 mPa·s.

In certain embodiments of the disclosure described herein, high concentrations of the therapeutic biologic in the particles and high concentrations of particles in the liquid carrier are possible. In some embodiments, the latter may be achieved by mixing particles of various sizes.

In some embodiments, the treatment methods described herein, use a concentration of the therapeutic biologic in the composition of about 20 mg/mL to about 700 mg/mL, e.g., about 20, 30, 50, 75, 100, 125, 150, 175, 200, 225, 250, 275, 300, 325, 350, 375, 400, 425, 450, 475, 500, 525, 550, 575, 600, 625, 650, 675 mg/mL to about 700 mg/mL; about 20 mg/mL to about 650 mg/mL, e.g., about 20, 30, 50, 75, 100, 125, 150, 175, 200, 225, 250, 275, 300, 325, 350, 375, 400, 425, 450, 475, 500, 525, 550, 575, 600, 625 mg/mL to about 650 mg/mL; about 20 mg/mL to about 600 mg/mL, e.g., about 20, 30, 50, 75, 100, 125, 150, 175, 200, 225, 250, 275, 300, 325, 350, 375, 400, 425, 450, 475, 500, 525, 550, 575 mg/mL to about 600 mg/mL; about 20 mg/mL to about 575 mg/mL, e.g., about 20, 30, 50, 75, 100, 125, 150, 175, 200, 225, 250, 275, 300, 325, 350, 375, 400, 425, 450, 475, 500, 525, 550 mg/mL to about 575 mg/mL; about 20 mg/mL to about 550 mg/mL, e.g., about 20, 30, 50, 75, 100, 125, 150, 175, 200, 225, 250, 275, 300, 325, 350, 375, 400, 425, 450, 475, 500, 525 mg/mL to about 550 mg/mL; about 20 mg/mL to about 525 mg/mL, e.g., about 20, 30, 50, 75, 100, 125, 150, 175, 200, 225, 250, 275, 300, 325, 350, 375, 400, 425, 450, 475, 500 mg/mL to about 525 mg/mL; about 20 mg/mL to about 500 mg/mL, e.g., about 20, 30, 50, 75, 100, 125, 150, 175, 200, 225, 250, 275, 300, 325, 350, 375, 400, 425, 450, 475 mg/mL to about 500 mg/mL; about 20 mg/mL to about 475 mg/mL, e.g., about 20, 30, 50, 75, 100, 125, 150, 175, 200, 225, 250, 275, 300, 325, 350, 375, 400, 425, 450 mg/mL to about 475 mg/mL; about 20 mg/mL to about 450 mg/mL, e.g., about 20, 30, 50, 75, 100, 125, 150, 175, 200, 225, 250, 275, 300, 325, 350, 375, 400, 425 mg/mL to about 450 mg/mL; about 20 mg/mL to about 425 mg/mL, e.g., about 20, 30, 50, 75, 100, 125, 150, 175, 200, 225, 250, 275, 300, 325, 350, 375, 400 mg/mL to about 425 mg/mL; about 20 mg/mL to about 400 mg/mL, e.g., about 20, 30, 50, 75, 100, 125, 150, 175, 200, 225, 250, 275, 300, 325, 350, 375 mg/mL to about 400 mg/mL; about 20 mg/mL to about 375 mg/mL, e.g., about 20, 30, 50, 75, 100, 125, 150, 175, 200, 225, 250, 275, 300, 325, 350 mg/mL to about 375 mg/mL; about 20 mg/mL to about 350 mg/mL, e.g., about 20, 30, 50, 75, 100, 125, 150, 175, 200, 225, 250, 275, 300, 325 mg/mL to about 350 mg/mL; about 20 mg/mL to about 325 mg/mL, e.g., about 20, 30, 50, 75, 100, 125, 150, 175, 200, 225, 250, 275, 300 mg/mL to about 325 mg/mL; or about 20 mg/mL to about 300 mg/mL, e.g., about 20, 30, 50, 75, 100, 125, 150, 175, 200, 225, 250, 275 mg/mL to about 300 mg/mL. In other embodiments, the concentration of the therapeutic biologic in the composition is about 20 mg/mL to about 650 mg/mL. In certain embodiments, the concentration of the therapeutic biologic in the composition is about 100 mg/mL to about 500 mg/mL. In still other embodiments, the concentration of the therapeutic biologic in the composition is about 200 mg/mL to about 400 mg/mL. In preferred embodiments, the concentration of the therapeutic biologic in the composition is about 300 mg/mL to about 400 mg/mL. In certain preferred embodiments, the concentration of the therapeutic biologic in the composition is about 350 mg/mL to about 400 mg/mL. In some embodiments, the concentration of the therapeutic biologic in the composition is about 300 mg/mL to about 500 mg/mL.

In certain embodiments, insoluble particulate matter with characteristic sizes greater than or equal to about 100 μm that persist upon dissolution in an aqueous liquid are referred to as Visible Particles (VP). In preferred embodiments of the disclosure described herein, the composition is substantially free of Visible Particles (VP). In certain preferred embodiments, the aqueous liquid is water, aqueous buffer or a physiologically relevant aqueous liquid. As used herein, the term "physiologically relevant aqueous liquid" refers to any water-containing body fluid distributed in the extracellular compartment, e.g., extracellular fluid, interstitial fluid, intravascular fluid (blood, plasma, and lymph) and cerebrospinal fluid.

In other embodiments, insoluble particulate matter with characteristic sizes of about 1 μm to about 100 μm that persist upon dissolution in an aqueous liquid are referred to as Subvisible Particles (SvPs). SvPs are present in quantities of about 0 to 100,000,000 per mL, e.g., about 0 to about 10,000,000 per mL, about 0 to about 1,000,000 per mL, about 0 to about 500,000 per mL, about 0 to about 100,000 per mL, about 0 to about 50,000 per mL, about 0 to about 10,000 per mL, about 0 to about 6,000 per mL, about 0 to about 1,000 per mL, about 0 to about 600 per mL, about 0 to about 250 per mL, about 0 to about 100 per mL, about 0 to about 60 per mL, or about 0 to about 10 per mL. In other embodiments, the count of particles with characteristic size greater than or equal to 10 μm is about 0 to about 6,000 per mL, e.g., about 0 to about 1,000 per mL, about 0 to about 100 per mL, about 0 to about 10 per mL, about 0 to about 5 per mL, about 0 to about 3 per mL, or about 0 to about 1 per mL. In certain embodiments, the count of particles with characteristic size greater than or equal to 25 μm is about 0 to about 600 per mL, e.g., about 0 to about 100 per mL, about 0 to about 10 per mL, about 0 to about 3 per mL, about 0 to about 1 per mL, about 0 to about 0.5 per mL, or about 0 to about 0.1 per mL. Exemplary methods of measuring SvPs include analysis of the therapeutic biologic with a Coulter Counter, HIAC Royco, or micro-flow imaging system after reconstitution and dilution of the therapeutic biologic to a standard concentration, e.g., about 100 mg/mL or about 1 mg/mL. In still other embodiments, the composition has a concentration of insoluble Subvisible Particles (SvPs) of about 0 per mL to about 100,000,000 per mL of greater than about 10 μm particles upon dissolution in an aqueous liquid. In certain embodiments, the composition has a concentration of insoluble Subvisible Particles (SvPs) of about 0 per mL to about 6000 per mL of greater than about 10 μm particles upon dissolution in an aqueous liquid. In preferred embodiments, the composition has a concentration of insoluble Subvisible Particles (SvPs) of about 0 per mL to about 600 per mL of greater than about 25 μm particles upon dissolution in an aqueous liquid. In certain preferred embodiments, the composition is substantially free of insoluble Subvisible Particles (SvPs) upon dissolution in an aqueous liquid.

In certain embodiments, the composition has a concentration of insoluble Subvisible Particles (SvPs) having a characteristic size of greater than about 10 μm of about 0 per mL to about 100,000,000 per mL upon dissolution in an aqueous liquid. In some embodiments, the composition has a concentration of insoluble Subvisible Particles (SvPs) having a characteristic size of greater than about 10 μm of about 0 per mL to about 6000 per mL upon dissolution in an aqueous liquid. In other embodiments, the composition has a concentration of insoluble Subvisible Particles (SvPs) having a characteristic size of greater than about 25 μm of about 0 per mL to about 600 per mL upon dissolution in an aqueous liquid. In preferred embodiments, the aqueous liquid is water, aqueous buffer or a physiologically relevant aqueous liquid.

In some embodiments, insoluble particulate matter with characteristic sizes of about 100 nm to about 1 μm that persist upon dissolution in an aqueous liquid are referred to as submicron particles (SMP) and sometimes known as nanoparticles. The presence of such SMPs is thought to contribute to immunogenicity and thus should be avoided to minimize such effects. Quantitatively, SMPs are present in quantities of about 0 to $5\times10^{12}$ per mL, e.g., about 0 to about $0.5\times10^{12}$ per mL, about 0 to about $50\times10^{9}$ per mL, about 0 to about $10\times10^{9}$ per mL, about 0 to about $5\times10^{9}$ per mL, about 0 to about $0.5\times10^{9}$ per mL, about 0 to about $50\times10^{6}$ per mL, about 0 to about $1\times10^{6}$ per mL, about 0 to about 500,000 per mL, about 0 to about 200,000 per mL, about 0 to about 100,000 per mL, about 0 to about 10,000 per mL, about 0 to about 5000 per mL, or about 0 to about 1000 per mL. Exemplary methods of measuring SMPs quantitatively include analysis of the therapeutic biologic with a Nano-Sight, micro-flow imaging system, asymmetric field flow fractionation coupled to a multi-angle laser light scattering (AF4 MALS), Dynamic Light Scattering (DLS), or Flow-Cam imaging after reconstitution and dilution of the therapeutic biologic to a standard concentration, e.g., about 100 mg/mL, about 1 mg/mL, or about 1 μg/mL. Qualitatively, SMPs are within a range comparable to the starting monomeric therapeutic biologic solution. In preferred embodiments, the composition is substantially free of submicron particles (SMP) upon dissolution in an aqueous liquid. In certain preferred embodiments, the aqueous liquid is water, aqueous buffer or a physiologically relevant aqueous liquid.

As disclosed herein, the term "immunogenicity" refers to the induction of an immune response by an injected composition of the therapeutic biologic (the antigen), while "antigenicity" refers to the reaction of the composition of the therapeutic biologic with preexisting antibodies. Collectively, antigenicity and immunogenicity are referred to as "immunoreactivity". In preferred embodiments, the composition has substantially similar immunogenicity compared to an aqueous composition comprising the therapeutic biologic in monomeric form. In certain preferred embodiments, the composition is substantially non-immunogenic.

The ratio between toxicity and therapeutic effect for a particular composition is its therapeutic index and can be expressed as the ratio between $LD_{50}$ (the amount of compound lethal in 50% of the population) and $ED_{50}$ (the amount of compound effective in 50% of the population). Compositions that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized, e.g., subcutaneous injection. See, e.g. Fingl et al., In: THE PHARMACOLOGICAL BASIS OF THERAPEUTICS, Ch. 1, p. 1, 1975. The exact composition, route of administration and dosage can be chosen by the individual physician in view of the patient's condition and the particular method in which the composition is delivered.

Oncology or anti-inflammatory drugs often have significant side effects that are due to off-target toxicity such as hematologic toxicity, neurological toxicity, cardiotoxicity, hepatotoxicity, nephrotoxicity, ototoxicity, or encephalotoxicity. For example, taxanes such as docetaxel may cause the following adverse effects: infections, neutropenia, anemia, febrile neutropenia, hypersensitivity, thrombocytopenia, myelotoxicity, myelosuppression, neuropathy, dysgeusia, dyspnea, constipation, anorexia, nail disorders, fluid retention, asthenia, pain, nausea, diarrhea, vomiting, fatigue, non-specific neuro cognitive problems, vertigo, encephalopathy, mucositis, alopecia, skin reactions, myalgia, or a combination thereof.

In some embodiments of the disclosure described herein, the toxicity is hematologic toxicity, neurological toxicity, gastrointestinal toxicity, cardiotoxicity, hepatotoxicity, nephrotoxicity, ototoxicity or encephalotoxicity. In other embodiments, the side effects that are associated with toxicity can be neutropenia, leukopenia, thrombocytopenia, myelotoxicity, myelosuppression, neuropathy, fatigue, non-specific neurocognitive problems, vertigo, encephalopathy, anemia, dysgeusia, dyspnea, constipation, anorexia, nail disorders, fluid retention, asthenia, pain, nausea, vomiting mucositis, alopecia, skin reactions, myalgia, hypersensitivity, anaphylaxis, or a combination thereof.

In certain embodiments, the composition has substantially similar toxicity compared to an aqueous composition comprising monomeric therapeutic biologics. In preferred embodiments, the composition has reduced toxicity compared to an aqueous composition comprising the therapeutic biologic in monomeric form. In certain preferred embodiments, the composition is substantially non-toxic.

The present disclosure as described herein, concerns a highly concentrated composition comprising a plurality of particles suspended in a low viscosity pharmaceutically acceptable liquid carrier, each particle comprising at least one therapeutic biologic, wherein the composition upon dissolution in water, buffers or other physiologically relevant aqueous liquids, e.g., biological fluids in the patients' body, have a substantially similar turbidity compared to a similar aqueous composition comprising monomeric therapeutic biologics. The term "turbidity" means the cloudiness or haziness of a fluid caused by individual particles that remain insoluble after dissolution at the desired concentration in water, buffer or other physiologically relevant aqueous liquids, e.g., biological fluids in the patients' body. As used herein, "physiologically relevant" conditions as may be encountered inside a mammal or human, can apply. The skilled artisan will be able to determine the set of conditions most appropriate for testing in accordance with the ultimate application of the compositions described herein. In some embodiments, the composition upon dissolution in an aqueous liquid has a substantially similar turbidity compared to an aqueous composition comprising monomeric therapeutic biologics. In preferred embodiments, the composition upon dissolution in an aqueous liquid is substantially free of turbidity. In certain preferred embodiments, the aqueous liquid is water, aqueous buffer or a physiologically relevant aqueous liquid.

In certain embodiments, the disclosure concerns highly concentrated compositions of low turbidity comprising a carbohydrate, a pH adjusting agent, a salt, a surfactant, a protein stabilizer, an emulsifier, an amino acid, and a plurality of particles comprising a therapeutic biologic, in a non-aqueous liquid carrier. In preferred embodiments, the disclosure concerns highly concentrated compositions of low turbidity comprising trehalose, arginine hydrochloride, sodium succinate, succinic acid, citric acid, sodium citrate, histidine, histidine hydrochloride, sodium chloride, hydroxypropyl beta-cyclodextrin, sulfobutylether beta-cyclodextrin, polysorbate, or sorbitan monooleate, and a plurality of particles comprising an antibody, in ethyl oleate. In certain preferred embodiments, the composition upon dissolution in water, aqueous buffer or any physiologically relevant aqueous liquid is substantially free of turbidity.

In certain embodiments, the particles can be suspended in a non-aqueous or aqueous liquid carrier, thereby forming a non-aqueous or aqueous pharmaceutically acceptable composition. Importantly, the process of generating non-aqueous or aqueous composition with at least one therapeutic biologic does not significantly alter the structure or bioactivity of the biologic as described herein. In addition, in certain other embodiments, the present disclosure allows for the delivery of higher doses of therapeutic biologics while minimizing the delivery volume, shortening administration time, and/or reducing pain.

In some embodiments, the liquid carrier is non-aqueous or aqueous. In other embodiments, the liquid carrier is non-aqueous. In still other embodiments, the liquid carrier is aqueous.

In other embodiments, the non-aqueous liquid carrier is an organic solvent or an ionic liquid. In some embodiments, the organic solvent is benzyl benzoate, coconut oil, cottonseed oil, fish oil, grape seed oil, hazelnut oil, hydrogenated vegetable oils, olive oil, palm seed oil, peanut oil, peppermint oil, safflower oil, sesame oil, soybean oil, sunflower oil, walnut oil, corn oil, acetone, ethyl acetate, ethyl lactate, dimethylacetamide, dimethyl isosorbide, dimethyl sulfoxide, glycofurol, diglyme, methyl tert-butyl ether, N-methyl pyrrolidone, perfluorodecalin, polyethylene glycol, 2-pyrrolidone, tetrahydrofurfuryl alcohol, triglycerides, e.g., Miglyol, triglycerides of the fractionated plant fatty acids C8 and C10, propylene glycol diesters of saturated plant fatty acids C8 and C10, ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, polyoxyl 40 hydrogenated castor oil, polyoxyl 35 castor oil, simple alcohols such as ethanol, octanol, hexanol, decanol, propanol, and butanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, diethylene glycol monoethyl ether, propylene carbonate, solketal, isosorbide dimethyl ether, ethyl formate, ethyl hexyl acetate, or a combination thereof. In still other embodiments, the ionic liquid comprises pyridinium, pyridazinium, pyrimidinium, pyrazinium, imidazolium, pyrazolium, thiazolium, oxazolium, triazolium, ammonium, sulfonium, halides, sulfates, sulfonates, carbonates, phosphates, bicarbonates, nitrates, acetates, $PF_6$—, $BF_4$—, triflate, nonaflate, bis(trifyl)amide, trifluoroacetate, heptafluorobutanoate, haloaluminate, or a combination thereof. In preferred embodiments, the organic solvent is ethyl oleate, trigylcerides, e.g., Miglyol, ethyl laureate, ethyl macadamiate, ethyl caprate, diethyl succinate, diethylene glycol monoethyl ether, propylene carbonate, or a combination thereof. In certain preferred embodiments, the organic solvent is ethyl oleate or trigylcerides.

In some embodiments, the aqueous liquid carrier is water, 0.9% saline, lactated Ringer's solution, dextrose 5%, or a buffer. In other embodiments, the buffer is acetate buffer, histidine buffer, succinate buffer, HEPES buffer, tris buffer, carbonate buffer, citrate buffer, phosphate buffer, phosphate-buffered saline, glycine buffer, barbital buffer, cacodylate buffer, ammonium formate buffer, urea solution, or a combination thereof. In preferred embodiments, the aqueous liquid carrier is water.

In certain embodiments, the non-aqueous or aqueous liquid carrier further comprises a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, a nutrient media, analgesic, or a combination thereof. In preferred embodiments, the non-aqueous or aqueous liquid carrier further comprises a carbohydrate, a pH adjusting agent, a salt, a surfactant, a protein stabilizer, an emulsifier, an amino acid, or a combination thereof. In certain preferred embodiments, the aqueous liquid carrier further comprises a carbohydrate, a pH adjusting agent, a salt, a surfactant, a protein stabilizer, an emulsifier, an amino acid, or a combination thereof.

In other embodiments, the carbohydrate may be from the families of monosaccharides, disaccharides, oligosaccharides, or polysaccharides. In some embodiments, the carbohydrate is dextran, trehalose, sucrose, agarose, mannitol, lactose, sorbitol, maltose, starch, alginates, xanthan, galactomanin, agar, agarose, or a combination thereof. In certain embodiments, the carbohydrate is dextran, trehalose, sucrose, agarose, mannitol, lactose, sorbitol, maltose, or a combination thereof. In preferred embodiments, the carbohydrate is trehalose, cyclodextrins, hydroxypropyl beta-cyclodextrin, sulfobutylether beta-cyclodextrin, or a combination thereof. Cyclodextrins are available in three different forms α, β, and γ based on the number of number of glucose monomers. The number of glucose monomers in α, β, and γ cyclodextrin can be 6, 7, or 8, respectively.

In some embodiments, the pH adjusting agent is acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, monosodium glutamate, sodium hydroxide, potassium hydroxide, or a combination thereof. In other embodiments, the pH adjusting agent is citrate, histidine, phosphate, succinate, sodium hydroxide, potassium hydroxide, or a combination thereof. In certain embodiments, the pH adjusting agent is hydrochloric acid or citric acid.

In other embodiments, the salt is sodium chloride, calcium chloride, potassium chloride, sodium hydroxide, stannous chloride, magnesium sulfate, sodium glucoheptonate, sodium pertechnetate, guanidine hydrochloride, potassium hydroxide, magnesium chloride, potassium nitrate, or a combination thereof. In preferred embodiments, the salt is sodium chloride.

In some embodiments, the chelator is disodium edetate, ethylenediaminetetraacetic acid, pentetic acid, or a combination thereof. In other embodiments, the mineral is calcium, zinc, titanium dioxide, or a combination thereof. In certain embodiments, the polymer is propyleneglycol, glucose star polymer, silicone polymer, polydimethylsiloxane, polyethylene glycol, carboxymethylcellulose, poly(glycolic acid), poly(lactic-co-glycolic acid), polylactic acid, polycaprolactone (PCL), polyvinylpyrrolidone (PVP), ficoll, dextran, or a combination thereof.

In other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, Aerosol-OT (sodium bis(2-ethylhexyl) sulfosuccinate), sodium laureth sulfate, lecithin, sorbitan esters, or a combination thereof. In some embodiments, the surfactant includes, but is not limited to: (i) cationic surfactants such as; cetyltrimethylammonium chloride, hexadecyltrimethylammonium chloride, benzalkonium chloride, benzethonium chloride, dioctadecyldimethylammonium bromide; (ii) anionic surfactants such as magnesium stearate, sodium dodecyl sulfate, dioctyl sodium sulfosuccinate, sodium myreth sulfate, perfluorooctanesulfonate, alkyl ether phosphates; (iii) non-ionic surfactants such as alkylphenol ethoxylates (TritonX-100), fatty alcohol ethoxylates (octaethylene glycol monododecyl ether, cocamide diethanolamine, poloxamers, glycerolmonostearate, fatty acid esters of sorbitol (sorbitan monolaurate, Tween 80, Tween 20; and (iv) zwitterionic surfactants such as cocamidopropyl hydroxysultaine, and 3-[(3-Cholamidopropyl)dimethylammonio]-1-propanesulfonate (CHAPS). In certain embodiments, the surfactant is polysorbate, docusate, lecithin or sorbitan esters. In preferred embodiments, the surfactant is sorbitan esters, polysorbate 20 or polysorbate 80.

In some embodiments, the protein stabilizer is acetyltryptophanate, caprylate, N-acetyltryptophan, trehalose, polyethylene glycol (PEG), polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, mannitol, saccharides, or a combination thereof. In certain embodiments, the protein stabilizer is trehalose, polyethylene glycol (PEG), polyoxamers, polyvinylpyrrolidone, polyacrylic acids, poly(vinyl) polymers, polyesters, polyaldehydes, tert-polymers, polyamino acids, hydroxyethyl starch, N-methyl-2-pyrrolidone, sorbitol, sucrose, mannitol, cyclodextrin, hydroxypropyl beta-cyclodextrin, sulfobutylether beta-cyclodextrin, acetyltryptophanate, caprylate, N-acetyltryptophan, or a combination thereof. In preferred embodiments, the protein stabilizer is trehalose, polyethylene glycol (PEG), cyclodextrin, hydroxypropyl beta-cyclodextrin, sulfobutylether beta-cyclodextrin, or a combination thereof. In certain preferred embodiments, the PEG is PEG 200, PEG 300, PEG 3350, PEG 8000, PEG 10000, PEG 20000, or a combination thereof. The stabilizers, used synonymously with the term "stabilizing agent", as described herein, can be a salt, a carbohydrate, saccharides or amino acids, preferably a carbohydrate or saccharide admitted by the authorities as a suitable additive or excipient in pharmaceutical compositions.

Examples of emulsifiers suitable for use in the non-aqueous or aqueous liquid carrier include, but are not limited to, lipophilic agents having an HLB of less than 7, such as mixed fatty acid monoglycerides; mixed fatty acid diglycerides; mixtures of fatty acid mono- and diglycerides; lipophilic polyglycerol esters; glycerol esters including glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; or a combination thereof. In some embodiments, the emulsifier is polysorbate, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, a poloxamer, or a combination thereof. In preferred embodiments, the emulsifier is polysorbate 80, sorbitan monooleate, or a combination thereof.

In other embodiments, the antiseptic is phenol, m-cresol, benzyl alcohol, 2-phenyloxyethanol, chlorobutanol, neomycin, benzethonium chloride, gluteraldehyde, beta-propiolactone, or a combination thereof.

In certain embodiments, the amino acid is alanine, aspartic acid, cysteine, isoleucine, glutamic acid, leucine, methionine, phenylalanine, pyrrolysine, serine, selenocysteine, threonine, tryptophan, tyrosine, valine, asparagine, arginine, histidine, glycine, glutamine, proline, or a combination thereof. In preferred embodiments, the amino acid is arginine, histidine, proline, asparagine, or a combination thereof.

In some embodiments, the antioxidant is glutathione, ascorbic acid, cysteine, N-acetyl-L-tryptophanate, tocopherol, histidine, methionine, or a combination thereof. In other embodiments, the protein is protamine, protamine sulfate, gelatin, or a combination thereof. In certain embodiments, the organic solvent is dimethyl sulfoxide, N-methyl-2-pyrrolidone, or a combination thereof. In still other embodiments, the preservative is methyl hydroxybenzoate, thimerosal, a paraben, formaldehyde, castor oil, or a combination thereof. The paraben can be a parahydroxybenzoate. In some embodiments, the bactericide is benzalkonium chloride (cationic surfactants), hypochlorites, peroxides, alcohols, phenolic compounds, e.g. carbolic acid, or a combination thereof.

In other embodiments, the fungicide is acibenzolar, 2-phenylphenol, anilazine, carvone, natamycin, potassium azide, or a combination thereof. In certain embodiments, the vitamin is thiamine, riboflavin, niacin, pantothenic acid, biotin, vitamin $B_6$, vitamin $B_{12}$, folate, niacin, ascorbic acid, calciferols, retinols, quinones, or a combination thereof. In still other embodiments, the preservative is sodium nitrate, sulfur dioxide, potassium sorbate, sodium sorbate, sodium benzoate, benzoic acid, methyl hydroxybenzoate, thimerosal, parabens, formaldehyde, castor oil, or a combination thereof.

A number of nutrient media, preferably serum free, alone or in combination, may be used in the present disclosure, including commercially available media or other media known in the art. Examples of such media (all without serum or having had the serum removed) include ADC-1, LPM (Bovine Serum Albumin-free), F10 (HAM), F12 (HAM), DCCM1, DCCM2, RPMI 1640, BGJ Medium (Fitton-Jackson Modification), Basal Medium Eagle (BME—with the addition of Earle's salt base), Dulbecco's Modified Eagle Medium (DMEM-without serum), Glasgow Modification Eagle Medium (GMEM), Leibovitz L-15 Medium, McCoy's 5 A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA—with non-essential amino acids), among numerous others. In addition, serum-containing nutrient media may also be used in compositions according to the present disclosure.

In some embodiments, the analgesic is paracetamol, histamine receptor antagonist, e.g., an H1 or an H2 blocker, NSAIDs, COX-2 inhibitor, Celecoxib, Rofecoxib, Valdecoxib, Parecoxib, Lumiracoxib, Etoricoxib, Firocoxib, acetaminophen, opiates, Dextropropoxyphene, Codeine, Tramadol, Anileridine, Pethidine, Hydrocodone, Morphine, Oxycodone, Methadone, Diacetylmorphine, Hydromorphone, Oxymorphone, Levorphanol, Buprenorphine, Fentanyl, Sufentanil, Etorphine, Carfentanil, dihydromorphine, dihydrocodeine, Thebaine, Papaverine, diproqualone, Flupirtine, Tricyclic antidepressants, Acetaminophen or lidocaine, or a combination thereof. In certain embodiments, the analgesic is acetaminophen or lidocaine.

In preferred embodiments according to the disclosure as described herein, the particle composition has improved stability of the therapeutic biologic compared to an aqueous composition comprising the therapeutic biologic in monomeric form. A "stable" composition is one in which all the therapeutic biologic therein essentially retains their physical stability and/or chemical stability and/or biological activity upon storage at the intended storage temperature, e.g. 4-40° C. It is desired that the formulation essentially retains its physical and chemical stability, as well as its biological activity upon storage. The storage period is generally selected based on the intended shelf-life of the composition. Furthermore, the composition should be stable following freezing (to, e.g., −70° C.) and thawing of the composition, for example following 1, 2 or 3 cycles of freezing and thawing. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. In some embodiments, the composition is stable for at least one month. In still other embodiments, the composition is stable for at least two months. In certain other embodiments, the composition is stable for at least three months. In certain preferred embodiments, the composition is stable for at least three months at 40° C.

In certain embodiments, the composition further comprises at least one pharmaceutically acceptable additive, diluent, excipient, carrier, or a combination thereof.

In some embodiments, the compositions and methods disclosed herein, further comprise a pharmaceutically effective amount of at least one hyaluronan degrading agent that can be administered simultaneously, sequentially or intermittently with the composition. The subcutaneous tissue or the extracellular matrix is comprised of a network of fibrous proteins embedded within a viscoelastic gel of glycosaminoglycans. Hyaluronan is the prominent glycosaminoglycan of the subcutaneous tissue. Hyaluronan is secreted into the interstitium by fibroblasts as a viscous polymer that is subsequently degraded locally, in the lymph, through the action of hyaluronidases. Glycosaminoglycans are complex linear polysaccharides of the extracellular matrix and are characterized by repeating disaccharide structures of an N-substituted hexosamine and an uronic acid, as in the case of hyaluronan.

The hyaluronan degrading agent of the present disclosure can enhance the subcutaneous administration of the composition comprising a plurality of particles, for example, by enhancing and/or increasing the volume of the composition being administered by syringe injection thereby improving the absorption of the therapeutic biologic. The use of a hyaluronan degrading agent, such as hyaluronidase, can improve the subcutaneous administration of the therapeutic biologic into systemic circulation via the reversible hydrolyzation of hyaluronan, e.g., the reversible degradation of hyaluronan. The degradation of hyaluronan in the extracellular matrix temporarily opens channels in the subcutaneous tissue thereby allowing for larger volumes to be administered safely and comfortably into the subcutaneous tissue. Moreover, the degradation of hyaluronan temporarily decreases the viscosity of the subcutaneous tissue and promotes the dispersion of injected liquids facilitating their absorption. The effects of hyaluronidase are local and reversible with complete reconstitution of the hyaluronan tissue occurring within 24 to 48 hours. See, e.g. Frost, G. I., "Recombinant human hyaluronidase (rHuPH20): an enabling platform for subcutaneous drug and fluid administration", Expert Opinion on Drug Delivery, 2007; 4:427-440]. The increase in the permeability of the subcutaneous tissue through the degradation of hyaluronan correlates with the efficacy of hyaluronidase for their capability to increase the dispersion and absorption of compositions comprising a plurality of particles administered simultaneously, sequentially or intermittently.

In some embodiments, the composition further comprises at least one hyaluronan degrading agent, e.g., a pharmaceutically effective amount of at least one hyaluronan degrading agent. In certain embodiments, the hyaluronan degrading agent is a hyaluronidase enzyme, also referred to herein as a hyaluronidase. In some embodiments, the hyaluronidase is a soluble neutral-active hyaluronidase. In certain embodiments, the hyaluronidase is a mammalian hyaluronidase. In particular embodiments, the mammalian hyaluronidase is a human hyaluronidase. In preferred embodiments, the human hyaluronidase is a recombinant human hyaluronidase, e.g., a rHuPH20. Certain recombinant human hyaluronidases that are suitable for use in the compositions and methods disclosed herein are commercially available, e.g., rHuPH20 from Halozyme Therapeutics (San Diego, CA).

According to certain embodiments of the disclosure, the hyaluronan degrading agent can be administered simultaneously, sequentially or intermittently with the composition. As used herein, the term "simultaneous" or "near-simultaneous" administration refers to components that are administered at the same time, e.g. the simultaneous administration of both the composition and hyaluronan degrading agent. In some embodiments, the hyaluronan degrading agent and composition are administered in a single composition, e.g., co-formulated. In other embodiments, the hyaluronan degrading agent and composition are administered as separate formulations. However, one component could be administered within a few minutes or hours, for example, at the same medical appointment or doctor's visit. Such administration is referred to as "sequential" administration. In certain embodiments, sequential administration refers to the sequential administration of the hyaluronan degrading agent and the composition as described herein. In preferred embodiments, the hyaluronan degrading agent is administered first, followed by administration of one or more doses of the composition. In certain other embodiments, the components may be administered intermittently as co-formulations or separate formulations, e.g., every day, week or month. In preferred embodiments, the hyaluronan degrading agent is administered first. For example, an initial higher loading dose, followed by one or more lower doses of the hyaluronan degrading agent and/or composition may be administered. However, other dose regimens may be useful. The progress of these treatments can be easily monitored by conventional techniques and assays known to one skilled in the art.

The term "injectability" or "syringeability", refers to the relative ease with which a liquid composition or formulation can be administered to a subject through the use of an injection device. In particular, syringeability or injectability is influenced in part by the viscosity of the composition or formulation, the injection or transfer flow rate, and the needle characteristics, e.g., length and gauge. In some embodiments, the injectability or syringeability is determined by measuring the viscosity of the composition or formulation at various shear rates. In other embodiments, the injectability or syringeability is determined by measuring the breakaway and/or glide forces required to actuate a standard injection device consisting of a barrel, a plunger and a needle. In certain other embodiments, the barrel of the syringe has an inner diameter of at least 6 mm. As described herein, the injectability of the composition comprising a plurality of particles comprising at least one therapeutic biologic, is superior to that of an aqueous composition or formulation with about the same concentration of aqueous monomeric therapeutic biologics. The term "injectability" or "syringeability", can also refer to the injection performance of a pharmaceutical composition or formulation through a syringe equipped with a 16-33-gauge needle, optionally thin walled or ultra-thin walled (UTW). In certain embodiments, the syringe is equipped with a needle that is at least 13 mm in length. Injectability depends upon factors such as pressure or force required for injection, evenness of flow, aspiration qualities, and freedom from clogging. Injectability of the compositions may be assessed by comparing the injection force of a reduced-viscosity composition to a standard composition without added viscosity-lowering agents. The reduced viscosity compositions as described herein, can improve injectability with the injection force reduced by at least 10%, preferably by at least 30%, more preferably by at least 50%, and most preferably by at least 75% when compared to a standard composition having the same concentration of aqueous monomeric therapeutic biologic under otherwise the same conditions. Alternatively, injectability of the compositions can be assessed by comparing the time required to inject the same volume, such as about 2.0 mL, preferably about 1.5 mL, more preferably about 1.0 mL, and most preferably about 0.5 mL, of aqueous monomeric therapeutic biologic compositions when the syringe is depressed with the same force. The phrase "flow rate" refers to the volume of fluid that may pass through a given cross sectional area per unit time. In general, the flow rate formula is $Q=A \times v$, where Q is the flow rate, A is the cross-sectional area at a point in the path of the flow, and v is the average velocity of the liquid at that point. In certain embodiments, the flow rate is constant. In preferred embodiments, the flow rate is at least about 0.1 mL/sec.

The term "injection breakaway force" refers to the force required to overcome friction between the syringe barrel and plunger of a standard injection device before ejection of the contents of the syringe can take place at a steady rate, e.g., the maximum force required to break the static friction of the plunger. The force is applied at the outward-facing end of the syringe plunger shaft and directed along the axis of the syringe barrel. The contents of the syringe are ejected through a syringe needle of prescribed gauge and length. In certain embodiments, the injection breakaway force is measured through a load cell placed at the outward-facing end of the syringe plunger during actuation.

The term "injection glide force", "glide force" or "syringe force" refers to the force required to maintain a steady ejection of the contents of a standard injection device, e.g., the force required to maintain plunger movement once static friction has been overcome. The force is applied at the outward-facing end of the syringe plunger shaft and directed along the axis of the syringe barrel. The contents of the syringe are ejected through a syringe needle of prescribed gauge and length. The term "Newtonian regime" or "N" means a range of shear rates which are linearly proportional or nearly linearly proportional to the local strain rate at every point.

In some embodiments, the composition is dispensed using a syringe force of about 2 N to about 80 N. In other embodiments, the composition is dispensed using a syringe force of about 2 N to about 40 N. In still other embodiments, the composition is dispensed using a syringe force of about 2 N to about 30 N. In certain other embodiments, the composition is dispensed using a syringe force of about 2 N to about 25 N. In certain embodiments, the composition is dispensed using a syringe force of about 2 N to about 20 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20 N; about 2 N to about 19 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19 N; about 2 N to about 18 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18 N; about 2 N to about 17 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17 N; about 2 N to about 16 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16 N; about 2 N to about 15.5 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5 N; about 2 N to about 15 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15 N; about 2 N to about 14.5 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 N; about 2 N to about 14 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14 N; about 2 N to about 13.5 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5 N; about 2 N to about 13 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5, 13 N; about 2 N to about 12.5 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12, 12.5 N; about 2 N to about 12 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5, 12 N; about 2 N to about 11.5 N, e.g., about 2 N to about 2.5, 3, 3.5, 4, 4.5, 5, 5.5, 6, 6.5, 7, 7.5, 8, 8.5, 9, 9.5, 10, 10.5, 11, 11.5 N; about 2 N to about 11 N, e.g., about 2 N to about 2.5, 3, 3.5, 4, 4.5, 5, 5.5, 6, 6.5, 7, 7.5, 8, 8.5, 9, 9.5, 10, 10.5, 11 N; about 2 N to about 10.5 N, e.g., about 2 N to about 2.5, 3, 3.5, 4, 4.5, 5, 5.5, 6, 6.5, 7, 7.5, 8, 8.5, 9, 9.5, 10, 10.5 N; about 2 N to about 10 N, e.g., about 2 N to about 2.5, 3, 3.5, 4, 4.5, 5, 5.5, 6, 6.5, 7, 7.5, 8, 8.5, 9, 9.5, 10 N; about 2 N to about 9.5 N, e.g., about 2 N to about 2.5, 3, 3.5, 4, 4.5, 5, 5.5, 6, 6.5, 7, 7.5, 8, 8.5, 9, 9.5 N; about 2 N to about 9 N, e.g., about 2 N to about 2.5, 3, 3.5, 4, 4.5, 5, 5.5, 6, 6.5, 7, 7.5, 8, 8.5, 9 N; about 2 N to about 8.5 N, e.g., about 2 N to about 2.5, 3, 3.5, 4, 4.5, 5, 5.5, 6, 6.5, 7, 7.5, 8, 8.5 N; about 2 N to about 8 N, e.g., about 2 N to about 2.5, 3, 3.5, 4, 4.5, 5, 5.5, 6, 6.5, 7, 7.5, 8 N; about 2 N to about 7.5 N, e.g., about 2 N to about 2.5, 3, 3.5, 4, 4.5, 5, 5.5, 6, 6.5, 7, 7.5 N; about 2 N to about 7 N, e.g., about 2 N to about 2.5, 3, 3.5, 4, 4.5, 5, 5.5, 6, 6.5, 7 N; about 2 N to about 6.5 N, e.g., about 2 N to about 2.5, 3, 3.5, 4, 4.5, 5, 5.5, 6, 6.5 N; about 2 N to about 6 N, e.g., about 2 N to about 2.5, 3, 3.5, 4, 4.5, 5, 5.5, 6 N; about 2 N to about 5.5 N, e.g., about 2 N to about 2.5, 3, 3.5, 4, 4.5, 5, 5.5 N; about 2 N to about 5 N, e.g., about 2 N to about 2.5, 3, 3.5, 4, 4.5, 5 N; about 2 N to about 4.5 N, e.g., about 2 N to about 2.5, 3, 3.5, 4, 4.5 N; about 2 N to about 4 N, e.g., about 2 N to about 2.5, 3, 3.5, 4 N; or about 2 N to about 3.5 N, e.g., about 2 N to about 2.5, 3, 3.5 N. In preferred embodiments, the syringe force is about 2 N to about 15 N.

In other embodiments, the composition is dispensed using a syringe force of about 3 N to about 80 N. In some embodiments, the composition is dispensed using a syringe force of about 3 N to about 40 N. In still other embodiments, the composition is dispensed using a syringe force of about 3 N to about 30 N. In certain other embodiments, the composition is dispensed using a syringe force of about 3 N to about 25 N. In certain embodiments, the composition is dispensed using a syringe force of about 3 N to about 20 N, e.g., about 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, to about 20 N; about 3.5 N to about 19 N, e.g., about 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, to about 19 N; about 4 N to about 15 N, e.g., about 4.5, 5, 5.5, 6, 6.5, 7, 7.5, 8, 8.5, 9, 9.5, 10, 10.5, 11, 11.5, 12, 12.5, 13, 13.5, 14, 14.5, to about 15 N; about 4 N to about 14.5 N, e.g., about 4 N to about 4.5, 5, 5.5, 6, 6.5, 7, 7.5, 8, 8.5, 9, 9.5, 10, 10.5, 11, 11.5, 12, 12.5, 13, 13.5, 14, 14.5 N; about 4 N to about 14 N, e.g., about 4 N to about 4.5, 5, 5.5, 6, 6.5, 7, 7.5, 8, 8.5, 9, 9.5, 10, 10.5, 11, 11.5, 12, 12.5, 13, 13.5, 14 N; about 4 N to about 13.5 N, e.g., about 4 N to about 4.5, 5, 5.5, 6, 6.5, 7, 7.5, 8, 8.5, 9, 9.5, 10, 10.5, 11, 11.5, 12, 12.5, 13, 13.5 N; about 4 N to about 13 N, e.g., about 4 N to about 4.5, 5, 5.5, 6, 6.5, 7, 7.5, 8, 8.5, 9, 9.5, 10, 10.5, 11, 11.5, 12, 12.5, 13 N; about 4 N to about 12.5 N, e.g., about 4 N to about 4.5, 5, 5.5, 6, 6.5, 7, 7.5, 8, 8.5, 9, 9.5, 10, 10.5, 11, 11.5, 12, 12.5 N; about 4 N to about 12 N, e.g., about 4 N to about 4.5, 5, 5.5, 6, 6.5, 7, 7.5, 8, 8.5, 9, 9.5, 10, 10.5, 11, 11.5, 12 N; or about 4 N to about 11.5 N, e.g., about 4 N to about 4.5, 5, 5.5, 6, 6.5, 7, 7.5, 8, 8.5, 9, 9.5, 10, 10.5, 11, 11.5 N. In preferred embodiments, the syringe force is about 2 N to about 25 N. In other preferred embodiments, the syringe force is about 2 N to about 20 N. In certain preferred embodiments, the syringe force is about 2 N to about 15 N. In some embodiments, the syringe force increases at a lower rate than the viscosity of the composition as the concentration of the therapeutic biologic in the composition is increased.

Figure 7:
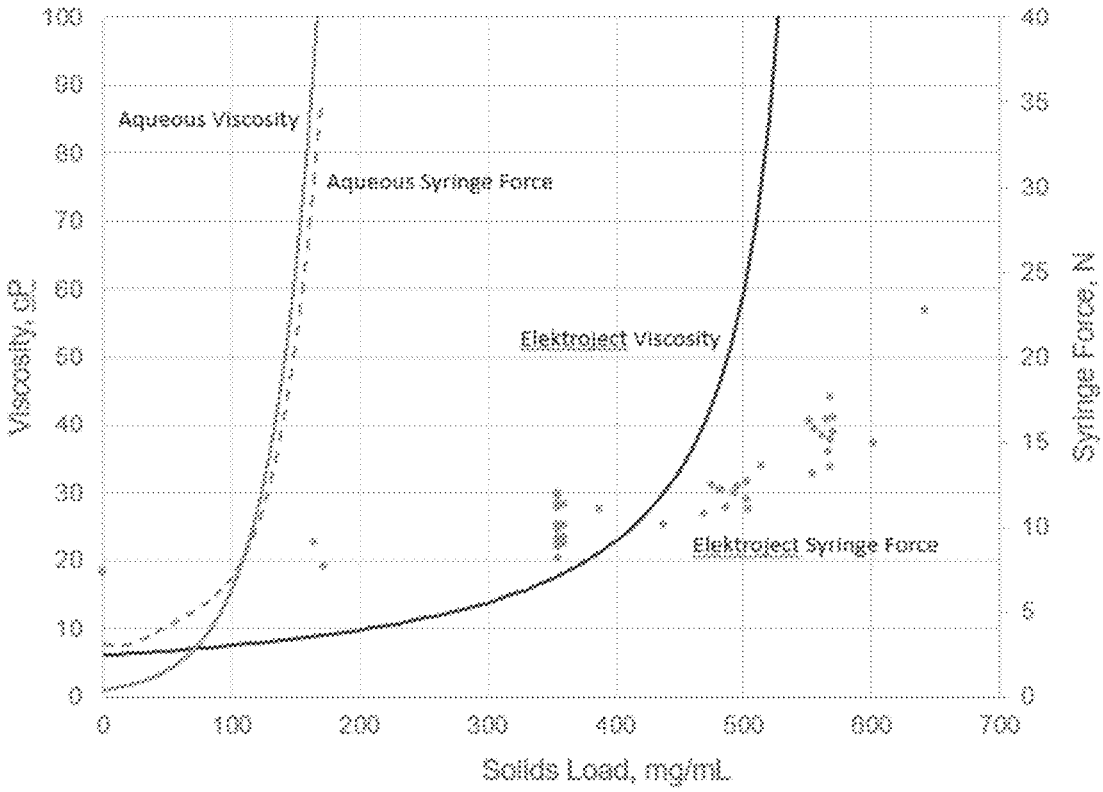
FIG. 7 shows a graph representing the viscosity and syringe force versus the solids load for the aqueous formulation and the particle composition (Elektroject).

As shown in FIG. 1, a syringe force versus the particle composition was studied using a 27-gauge ultra-thin walled (UTW) needle with a 4.7 mm inner diameter syringe barrel. The results in FIG. 1 showed that when the average glide force was plotted against the composition concentration of up to 600 mg/mL, the particle composition was dispensed using a syringe force of up to about 11.5 N. The data was fitted using the Krieger-Dogherty model for concentrated suspensions of solid, spherical particles. 20 N (Newtons) were plotted as reference to typical glide force limits. See Example 6. In other embodiments of the methods and compositions described herein, the syringe force increases at a lower rate than the viscosity of the composition as the concentration of the therapeutic biologic in the composition is increased. As shown in FIG. 7, the viscosity of the particle composition (Elektroject) and syringe force diverge as the protein concentration of the particle composition increases as compared to the viscosity and syringe force of the aqueous formulation which remain proportional.

The therapeutic compositions of the present embodiments are advantageously administered in the form of injectable compositions comprising a plurality of particles suspended in a low viscosity pharmaceutically acceptable liquid carrier, each particle comprising at least one therapeutic biologic or a salt thereof. In some embodiments, the composition is administered by parenteral, subcutaneous, oral, epidermal, intradermal, intramuscular, interarterial, intraperitoneal, or intravenous injection. In other embodiments, the composition is administered by subcutaneous injection. In certain embodiments, the composition is administered by syringe injection. In certain preferred embodiments, the composition is dispensed from a prefilled syringe.

The therapeutic biologics described herein can be formulated for parenteral administration, e.g., formulated for injection via the intravenous, intramuscular, subcutaneous, intravaginal or even intraperitoneal routes. Typically, such compositions can be prepared as suspensions; and, the particle preparations can also be emulsified. In some embodiments, the composition is administered by a prefilled device, e.g., needle-free injection device, cartridge or syringe injection. In other embodiments, the composition is administered by subcutaneous syringe injection. In certain embodiments, the composition is administered in one or more doses. In preferred embodiments, the composition is administered in a single dose. In certain other embodiments, the composition is administered in multiple doses.

The pharmaceutical compositions suitable for injectable use include sterile non-aqueous or aqueous liquid carriers; compositions including sesame oil, peanut oil, corn oil, or aqueous propylene glycol; and sterile particles for the extemporaneous preparation of sterile injectable solutions or dispersions. In all cases the composition must be sterile and must be fluid to the extent that it can be easily injected. It also should be stable under the conditions of current good manufacture procedures (cGMP) and storage and must be preserved against the contaminating action of microorganisms, such as bacteria and/or fungi.

The administering of the methods described herein, may comprise administering the composition using a 16-33-gauge needle. The 16-33-gauge needle may have a length of about 19 mm (¾-inch) or less; or preferably about 13 mm (½-inch) or less. In certain embodiments, the administering of the methods described herein, comprise administering the composition using a 27-33-gauge needle. In still other embodiments, the 27-33-gauge needle has a length of about 13 mm (½-inch) or less. In other embodiments, the composition is dispensed from a 25-gauge to a 33-gauge needle, e.g., a 26, 27, 28, 29, 30, 31, 32-gauge to a 33-gauge needle; a 26-gauge to a 33-gauge needle, e.g., a 27, 28, 29, 30, 31, 32-gauge to a 33-gauge needle; a 27-gauge to a 33-gauge needle, e.g., a 28, 29, 30, 31, 32-gauge to a 33-gauge needle; a 28-gauge to a 33-gauge needle, e.g., a 29, 30, 31, 32-gauge to a 33-gauge needle; a 29-gauge to a 33-gauge needle, e.g., a 30, 31, 32-gauge to a 33-gauge needle; or a 30-gauge to a 33-gauge needle, e.g., a 31, 32-gauge to a 33-gauge needle. In certain embodiments, the composition is dispensed from a 27-gauge to a 30-gauge needle; e.g., a 28, 29-gauge to a 30-gauge needle. In preferred embodiments, the composition is dispensed from a 27-gauge needle. In certain preferred embodiments, the composition is dispensed from a 30-gauge needle.

The administering of any one of the methods described herein, may comprise administering a dose of the composition to the subject in a single subcutaneous administration. In any one of the methods described herein, the method may further comprise co-administering at least one additional therapeutic agent, e.g., hyaluronidase, cytotoxic or cytostatic agent, a non-steroidal anti-inflammatory drug (NSAID), a pharmaceutically acceptable additive, diluent, excipient, carrier, or a combination thereof, to the subject.

The compositions as described herein, can be administered to a human or animal subject in vivo using a variety of known routes and techniques. For example, the composition may be provided as an injectable solution, suspension or emulsion, and administered via parenteral, subcutaneous, oral, epidermal, intradermal, intramuscular, interarterial, intraperitoneal, intravenous injection, using a conventional needle and syringe. Alternatively, needle-free injection devices are also suitable for administration. In some embodiments, the composition is administered by syringe injection or needle-free injection. In other embodiments, the composition is administered by needle-free injection. In certain other embodiments, the needle-free injection is liquid jet injection. Needle free injection encompasses a wide range of drug delivery systems that drive drugs through the skin using Lorentz, shock wave, pressure by gas or electrophoresis forces which propels the drug through the skin, eliminating the use of hypodermic needles. The term "jet injection", as used herein, refers to a needle-free injection method, wherein the composition is forced through an orifice, thereby generating an ultra-fine liquid stream of high pressure that is capable of penetrating mammalian skin. In certain embodiments, the jet injection is used for parenteral, subcutaneous, oral, epidermal, intradermal, intramuscular, interarterial, intraperitoneal, or intravenous injection of the composition according to the disclosure. In preferred embodiments, the jet injection is used for subcutaneous injection.

In some embodiments, the composition dissolves after administration to the subject in less than about 5 h, e.g., 4, 3, 2, 1 h. In other embodiments, the composition dissolves after administration to the subject in less than about 60 min, e.g., 59, 58, 57, 56, 55, 54, 53, 52, 51, 50, 49, . . . 10, 9, 8, 7, 6, 5, 4, 3, 2, 1 min. In still other embodiments, the composition dissolves after administration to the subject in less than about 20 min. In certain embodiments, the composition dissolves after administration to the subject in less than about 10 min. In certain preferred embodiments, the composition dissolves after administration to the subject in less than about 60 s, e.g., 59, 58, 57, 56, 55, 54, 53, 52, 51, 50, 49, . . . 10, 9, 8, 7, 6, 5, 4, 3, 2, 1 s.

In preferred embodiments according to the disclosure described herein, when the composition is administered, complete dissolution can occur within seconds mitigating any immunological risks posed by the particles that are persisting in the subcutaneous space. For example, compared to an equal dose of aqueous monomeric mAbs, dosing of particles comprising mAb has shown to produce a similar pharmacokinetic (PK) profile (AUC, Cmax and Tmax) and efficacy (tumor growth reduction) as described herein. In certain preferred embodiments, the composition immediately dissolves after administration to the subject.

The methods described herein, demonstrate the subcutaneous delivery of high concentration Abs (300-400 mg/mL protein) compositions without the loss of bioactivity. This has been achieved for a variety of Abs by using ethyl oleate (EO) as the liquid carrier. Ethyl oleate is a fatty acid ester with low viscosity of about 6 mPa·s at 25° C., and does not chemically interact with the particles during storage or in vivo dissolution. In some embodiments, ethyl oleate prevents aggregation and allows for easy resuspendability of the particles prior to injection.

The production of dense (1.32 g/cm$^3$), round, particles with controllable size distribution (polydispersity index <0.2) can be accomplished using a variety of Abs described herein. Focused Ion Beam Scanning Electron Microscopy (FIB-SEM) can be used to determine if the particles contain no void spaces which is vital for reaching high protein loadings in the composition and X-ray Photoelectron Spectroscopy (XPS) can be used to control the radial distribution of the particles. In certain embodiments, the particles size can be about 5 to about 10 which is preferable for reaching low viscosity compositions but small enough to prevent syringe clogging in a 27-gauge needle. By loading the particles at about 400 mg/mL (protein concentration 380 mg/mL, stabilizing excipient 20 mg/mL) in an ethyl oleate (EO) liquid carrier, a therapeutic composition can be formed with a viscosity of about 20 mPa·s (correlating to a syringe force of about 4 N) which is useful to store in a prefilled syringe.

As described herein, characterization of the structural stability of the particles in the composition was accomplished using size-exclusion chromatography (SEC), differential scanning fluorimetry (DSF), circular dichroism (CD), Cation Exchange Chromatography (CIEX) and Subvisible particle (SvP) analysis. In addition, preservation of bioactivity was analyzed using flow cytometry and Antibody Dependent Cellular Cytotoxicity (ADCC) assays.

Also described herein, SEC data confirmed that no aggregate formation was observed upon processing as compared with the label formulation (aqueous mAb as an FDA approved formulation) containing 1.9% aggregates compared to the reformulated particle composition which contained 1.8% aggregates. After 30 days of storage at 40° C., DSF showed less than 1° C. thermal shift across the samples, and CD could not detect any differences in secondary structure (beta-sheet percentage). CIEX was used to analyze charged variants of proteins as mandated by regulation (ICH Q6B), to ensure that no chemical modifications occurred during the methods described herein, and upon storage. In certain embodiments, the composition may be less prone to chemical modification upon storage than the FDA labeled formulation. This is due to the protein being more stable in the solid state as particles.

Figure 2A:
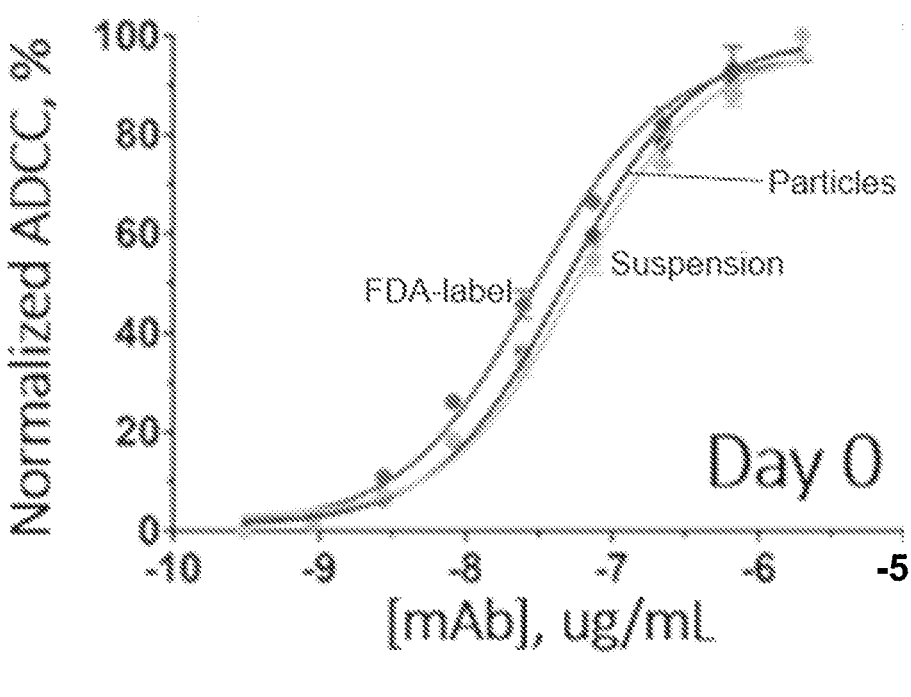
FIG. 2A shows a plot of normalized ADCC % as a function of mAb concentration for an FDA label formulation and the particle composition at day 0.
Figure 2B:
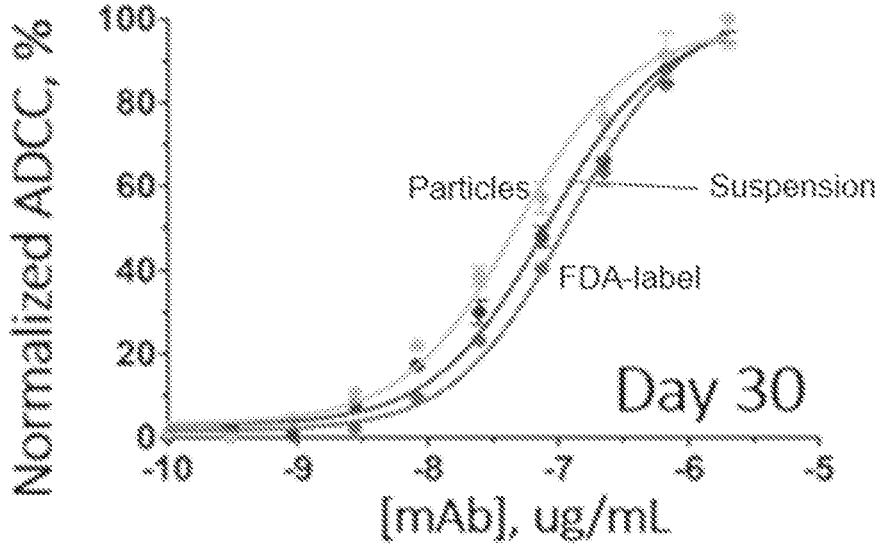
FIG. 2B shows a plot of normalized ADCC % as a function of mAb concentration for an FDA label formulation and the particle composition after storage for 30 days at 40° C.

Bioactivity preservation has been demonstrated through flow cytometry assays after storage for 30 days at 40° C. No discernable difference was evident between FDA label formulations and those compositions as described herein. ADCC assays were also performed to assess the binding and effector functions of each Ab for its target through exposure of Ab incubated target cell lines. As shown in FIG. 2A and FIG. 2B, in the case of FDA label formulation, bioactivity decreased significantly after storage, whereas for the particles in the composition, no decrease in activity was observed.

Prior to in vivo studies commencing, the particles used for the composition were obtained aseptically. Bacterial endotoxin levels were about 3 orders of magnitude below accepted injection standards (0.05 EU/mg to 0.25 EU/mg). In addition, a microbial growth assay indicated no observable growth.

Figure 3:
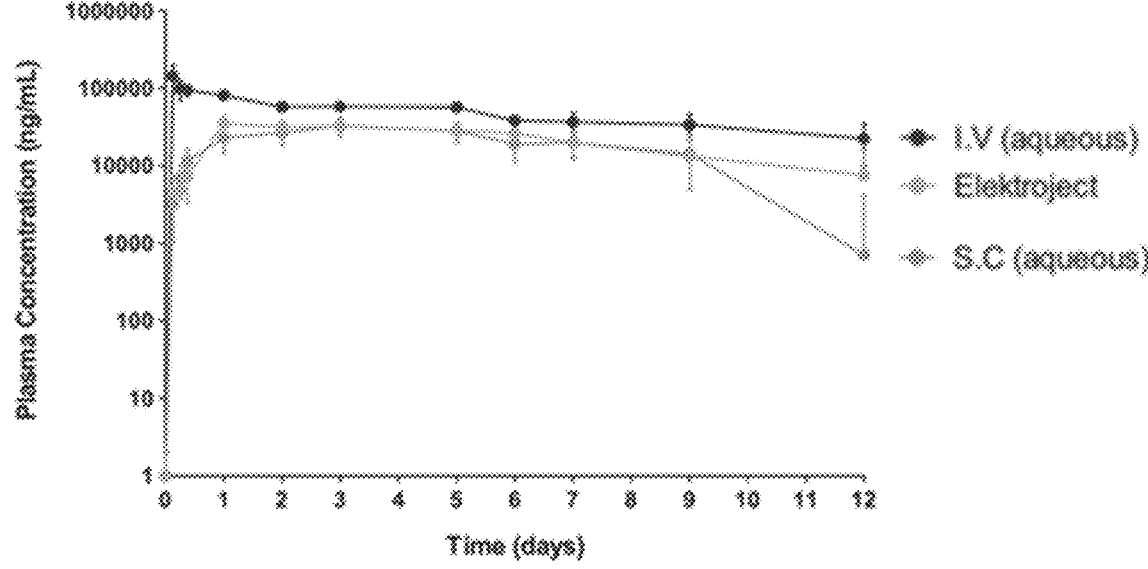
FIG. 3 shows a graph of the pharmacokinetic profiles for the IV rituximab aqueous, SC rituximab aqueous, and SC rituximab particle (Elektroject) composition cohorts of rats (Sprague Dawley).

The compositions described herein, are comparable to aqueous FDA label formulations in terms of rat pharmacokinetics (PK), SC clearance (mouse) and efficacy (mouse xenograft). The PK profiles are shown in FIG. 3, for an aqueous mAb formulation (SC injection) and the mAb composition (SC) in Sprague Dawley rats (n=5 for each condition) and were comparable and well within the accepted 80-125% bioequivalence limits. It has been demonstrated that the in vivo dissolution behavior of the particles ensured that the compositions can clear the injection site at a similar rate as compared to the standard aqueous formulations, as undissolved particles may potentially trigger an immunogenic reaction. See Example 7.

Figure 4:
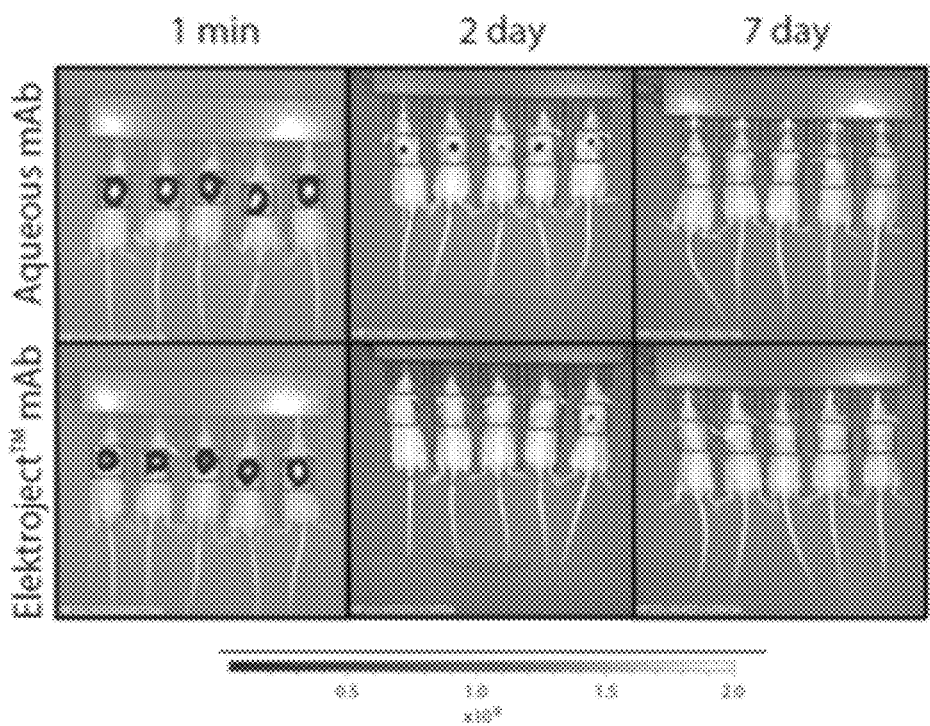
FIG. 4 show pictures of fluorescence images of SKH1 mice at one minute, 2 days and 7 days after receiving SC injections with an aqueous formulation or the particle composition (Elektroject) comprising rituximab.
Figure 5:
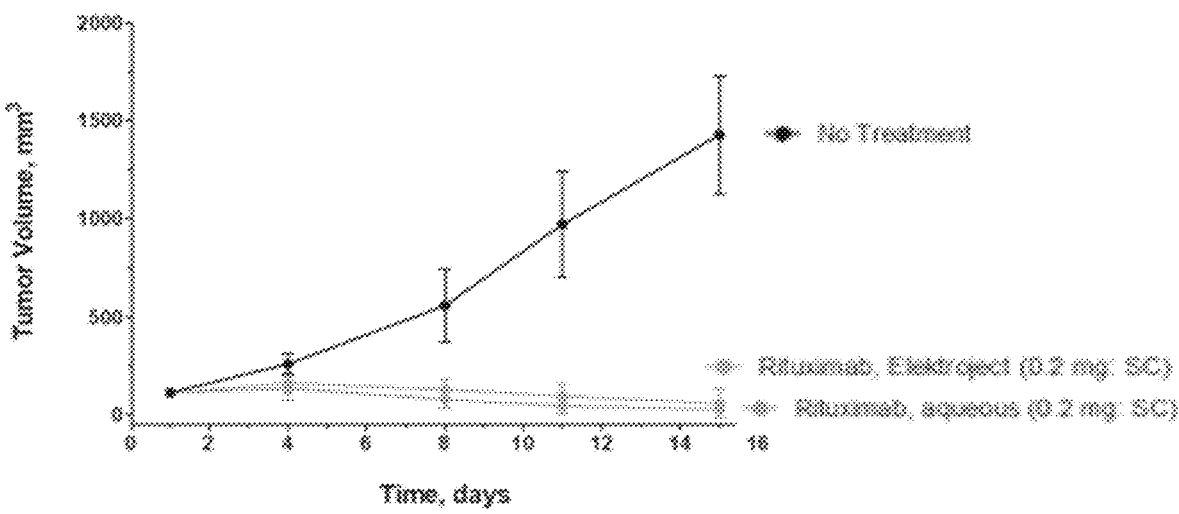
FIG. 5 shows a plot representing mean tumor volume growth curves for the no treatment group, SC rituximab aqueous group, and SC rituximab composition (Elektroject) cohorts of mice (Fox Chase SCID).

By conjugating fluorescent dyes to the rituximab, it was possible to visualize the dissolution of particles in vivo in the upper dorsal regions of SKH1 (hairless mice), as shown in FIG. 4. See Example 9. Similar clearance by fluorescence signal was observed for both the aqueous formulation and the particle composition. The animals were sacrificed after 14 days and five major organs (liver, spleen, kidney, lung and heart) were harvested, homogenized, and the fluorescence was quantified. Negligible fluorescence was observed, indicating that the rituximab was completely metabolized and that the particles were not trafficked to major organs of the animals. Efficacy studies relied on the measurement of DOHH-2 xenograft tumor sizes in Fox Chase SCID mice treated with aqueous formulation and the particle composition. As expected, FIG. 5 shows that the tumor growth was prevented with the particle composition and was comparable to the aqueous monomeric mAb formulation. See Example 8. Moreover, there was no substantial toxicity or other pathologies at the injection sites or at any major organs of any of the injected mice.

Figure 6:
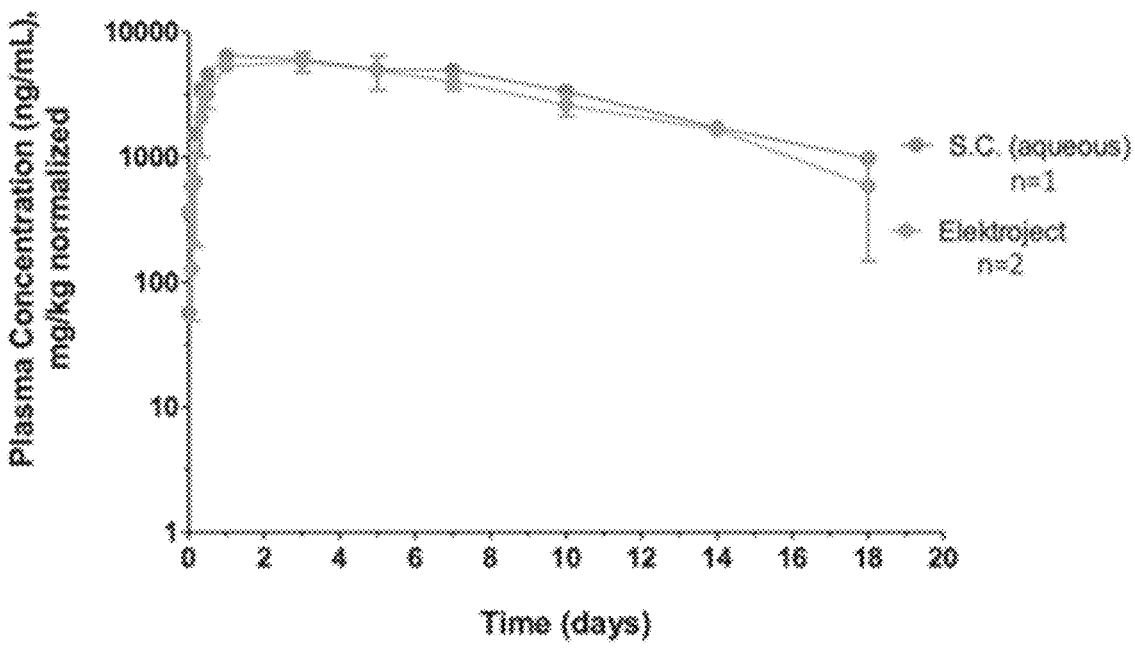
FIG. 6 shows a graph of the concentration of mAb in plasma of Yucatan minipigs normalized to body weight as a function of time for the aqueous formulation and the particle composition (Elektroject) after the SC injections.

Further in vivo studies have been extended to minipig hematology, serum chemistry, and PK. Hematology and serum chemistry measurements have shown to fall within normal ranges with no significant change in serum chemistry (day 3) or hematology (day 7) markers for either group. Pilot PK profiles (n=2 for each condition) show similar bioavailability in Yucatan minipigs where the subcutaneous space closely resembles that of humans, as shown in FIG. 6. See Example 10.

Kits

In various embodiments, a kit is envisioned comprising a plurality of particles comprising at least one therapeutic biologic. For example, a kit may include one or more additional containers, each with one or more of various materials (such as reagents, optionally in concentrated form, and/or devices) desirable from a commercial and user standpoint for use of a composition described herein. Non-limiting examples of such materials include, but not limited to, buffers, diluents, filters, needles, syringes, cartridges; carrier, package, container, vial and/or tube labels listing contents and/or instructions for use, and package inserts with instructions for use. In some embodiments, the present embodiments contemplate a kit for administering a therapy of the embodiments. The kit may comprise one or more sealed prefilled syringes or cartridges containing any of the pharmaceutical compositions of the present disclosure. The kit may include, for example, at least one antibody as well as reagents to prepare, formulate, and/or administer the components of the embodiments or perform one or more steps of the disclosed treatment methods. In other embodiments, the kit may also comprise a suitable container, which is a container that will not react with components of the kit, such as an Eppendorf tube, a syringe, a bottle, or a tube. The container may be made from sterilizable materials such as plastic or glass. In preferred embodiments, the composition is dispensed from a prefilled syringe.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure for delivering a pharmaceutically effective amount of a therapeutic biologic.

A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label may be used to indicate that the contents are to be used for a specific therapeutic application. In addition, the label may indicate directions for use of the contents, such as in the methods described herein. In certain embodiments, the pharmaceutical compositions are presented in a pack or dispenser device which contains one or more-unit dosage forms containing a therapeutic biologic provided herein. The pack for example contains metal or plastic foil, such as a blister pack. Or, the pack or dispenser device may be accompanied by instructions for administration. Or, the pack or dispenser may be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a therapeutic biologic provided herein formulated in a compatible pharmaceutical liquid carrier are prepared, placed in an appropriate container, and labeled for treatment of an indicated condition.

In some cases, a liquid composition as provided herein is formulated in a prefilled injection device, e.g., syringe or needle-free injection. In some embodiments, the liquid composition is formulated in a volume of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or about 2.5 mL. In other embodiments, the volume of the composition to be administered is about 2.5 mL. In certain embodiments, the volume of the composition to be administered is about 2.0 mL, preferably about 1.5 mL, more preferably about 1.0 mL, and most preferably about 0.5 mL. In preferred embodiments, the volume of the composition being dispensed from a prefilled syringe is about 1.5 mL to about 2.0 mL.

In other cases, the composition further comprises a pharmaceutically effective amount of at least one hyaluronan degrading agent, e.g., a hyaluronidase. In some embodiments, the composition, e.g., the composition formulated with at least one hyaluronan degrading agent, to be administered is a volume of less than about 2.0 L, e.g., less than about 1.8, 1.5, 1.2, 1.0, 0.8, 0.5, 0.3, 0.1 L, or about 800, 700, 600, 500, 400, 300, 200, 100, 90, 80, 70, 60, 50, 40, 30, 20, 10, 9.0, 8.0, 7.0, 6.0, 5.0, 4.0, 3.0, or about 2.5 mL. In other embodiments, the composition to be administered is less than about 20.0 mL. In certain embodiments, the composition to be administered is less than about 10.0 mL. In certain other embodiments, the composition to be administered is less than about 5.0 mL.

In some embodiments, such a kit comprises a prefilled injection device, e.g., syringe or needle-free injection, of the disclosure in a blister pack. The blister pack may itself be sterile on the inside. In other embodiments, prefilled injection device, e.g., syringe or needle-free injection, according to the disclosure may be placed inside such blister packs prior to undergoing sterilization, for example terminal sterilization.

The disclosure generically described, will be more readily understood by reference to the following examples, which are included merely for purposes of illustration of certain aspects and embodiments of the present disclosure, and are not intended to be limiting.

EXEMPLIFICATION

Abbreviations

Å angstrom
aa amino acids
BSA bovine serum albumin
° C. degrees Celsius
cm centimeter
d day
DCM dichloromethane
DIPEA diisopropylethylamine
DMA N,N-dimethylaniline
DMF dimethyl formamide
DMSO dimethyl sulfoxide
DTE dithioerythritol
DTT dithiothreitol
EDT 1,2-ethanedithiol
EDTA Ethylenediaminetetraacetic acid
eq. equivalent
Et ethyl
g gram
h hour
HPLC high performance liquid chromatography
Hz hertz
IV intravenous
kJ kilojoules
LC-MS liquid chromatograph mass spectrometry
m meta
mAb monoclonal antibody
MALDI-MS matrix-assisted laser desorption ionization mass spectrometry
Me methyl
MHz megahertz
min minute
microgram
microliter
μm micrometer
μM micromolar
mg milligram
mL milliliter
mm millimeter
mM millimolar
mol mole
nm nanometer
NMP N-methylpyrrolidone
p para
PBS phosphate-buffered saline
PEG polyethylene glycol
PEGA polyethylene glycol polyacrylamide
ppm parts per million
ps picosecond
RP-HPLC reversed phase-high performance liquid chromatography
rpm revolutions per minute
s second
SC subcutaneous sec second
SEM scanning electron microscopy
t tertiary
tert tertiary
UHMW ultrahigh molecular weight polyethylene
ug micrometer
UTW ultra thin wall
UV ultraviolet
V volts
vol % volume percent
wt % weight percent Immunotherapy The skilled artisan will understand that immunotherapies may be used with methods of the embodiments described herein. In the context of treating a disease or condition in a subject in need thereof, e.g., cancer, inflammatory disease or conditions, immune disease, renal disease, skin disease or conditions, or human immuno deficiency virus (HIV) infection, immunotherapeutics generally rely on the use of immune effector cells and therapeutic biologics or immune effectors to target and treat a disease or condition, e.g., cancer, inflammatory disease or conditions, immune disease, renal disease or skin disease or conditions, or human immuno deficiency virus (HIV) infection. Rituximab (RITUXAN®) is such an example. The immune effector may be, for example, an antibody specific for some marker on the surface of a target cell. The antibody may serve as an effector of therapy or it may recruit other cells to actually affect the cells. Various effector cells include but are not limited to cytotoxic T cells and NK cells.

In some embodiments, the methods described herein, feature a method of treating a patient by administering to the patient a composition comprising a plurality of particles comprising at least one therapeutic biologic in a composition for subcutaneous administration, for example, a composition as described herein. In certain embodiments, the patient has a disease or condition. In preferred embodiments, the composition is administered by subcutaneous syringe injection as a single dose. In other embodiments, the patient has cancer, inflammatory disease or conditions, immune disease, renal disease or skin disease or conditions, or human immuno deficiency virus (HIV) infection.

In certain embodiments of immunotherapy, the tumor cell must bear some marker that is amenable to targeting, i.e., is not present on the majority of other cells. Many tumor markers exist that may be suitable for targeting in the context of the present embodiments. Common tumor markers include but are not limited to CD20, carcinoembryonic antigen, tyrosinase (p97), gp68, TAG-72, HMFG, Sialyl Lewis Antigen, MucA, MucB, PLAP, laminin receptor, erb B, or p155. An alternative aspect of immunotherapy is to combine anticancer effects with immune stimulatory effects. Immune stimulating molecules also exist including but not limited to: cytokines, such as IL-2, IL-4, IL-12, GM-CSF, gamma-IFN, chemokines, such as MIP-1, MCP-1, IL-8, and growth factors, such as FLT3 ligand. Examples of immunotherapies currently under investigation or in use are immune adjuvants, e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

Materials

A biosimilar of Roche's Rituximab was purchased from a vendor that provided the antibody in an aqueous composition consistent with the FDA-label defined as 10 mg/mL rituximab, 9 mg/mL sodium chloride, 7.35 mg/mL sodium citrate dihydrate, and 0.7 mg/mL polysorbate 80. Composition of custom "feed solutions" used for processing particles were produced through modifying the FDA-label formulation by desalting followed by concentrating and adding desired excipients. Human IgG was obtained from Equitech-Bio Inc., Kerrville, TX.

Cell Culture: DOHH2 human B-cell Lymphoma cells (DSMZ) were maintained in Roswell Park Memorial Institute (RPMI) media containing 10% fetal bovine serum (FBS) and 1% penicillin G/streptomycin.

Animals: Female wild-type Albino Sprague Dawley Rats (Charles River Lab) were housed in the animal facility at the Tufts University Comparative Medicine Services (Tufts CMS). All use of animals described were conducted in compliance with the National Research Council's "Guide for the care and use of laboratory animals" and performed following detailed written protocols that were approved by the Institutional Animal Care and Use Committee (IACUC).

CR female CB.17 SCID mice (Charles River Labs) were housed in the animal facility at Charles River Labs. All animal procedures were formally reviewed and approved by the Institutional Animal Care and Use Committee (IACUC) at the Charles River Labs.

Male (castrated) Yucatan Pigs (S&S Farms, Constantine, MI) were housed in the animal facility at CBSET, Inc. All animal procedures were formally reviewed and approved by the Institutional Animal Care and Use Committee (IACUC) at CBSET, Inc.

Female wild-type Balb/c mice (Charles River Labs) were housed in the animal facility at Tufts University Comparative Medicine Services (Tufts CMS). All animal procedures were formally reviewed and approved by the Institutional Animal Care and Use Committee (IACUC) at the Tufts CMS.

As is known in the art, therapeutically effective amounts for use in humans can also be determined from animal models. For example, a dose for humans can be formulated to achieve a concentration that has been found to be effective in animals. The dosage in humans can be adjusted by monitoring the therapeutic biologics effectiveness and adjusting the dosage upwards or downwards, as described above. Adjusting the dose to achieve maximal efficacy in humans based on the methods described above and other methods is well within the capabilities of the ordinarily skilled artisan. A dose can be formulated in animal models to achieve a concentration range that includes the $IC_{50}$ (the concentration of the agent that achieves a half-maximal inhibition of symptoms) as determined in cell culture. Such information can be used to more accurately determine useful doses in humans. Levels in blood or a tissue sample can be measured, for example, by high performance liquid chromatography (HPLC). In general, the dose equivalent of agents is about 1 ng/kg to about 100 mg/kg for a typical subject.

Tumor Xenograft Models: DOHH2 human B-cell Lymphoma cells were collected at 70% confluency and administered subcutaneously (SC) in the flank of female CB.17 SCID mice. 1×107 DOHH-2 tumor cells in 0% Matrigel were injected at a cell injection volume of 0.1 mL/mouse. A pair match was performed when tumors reached an average size of 80-120 mm³ before the treatment was begun.

Methods

FlowCam: Particle sizing was measured using FlowCam; a dynamic image analysis instrument. Samples were diluted to about 1 mg/mL in isopropanol and passed through a thin channel. Images of particles were recorded and analyzed according to size and shape (count-weighted).

ImageJ Measurements: Particles diameters were measured using ImageJ analysis on SEM images. The analysis was performed on the 600× images. The ImageJ Particle Analysis tool was run on the image, identifying objects with a circularity of >0.8 and size >0.5 um with each object outlines (count-weighted). These outlines were visually inspected for good fit. Any mis-identified particles were manually rejected and any missed particles were manually included and measured using the ImageJ diameter tool.

Accelerated Storage Protocol: All samples were transferred to Wheaton E-Z ex-traction round-bottom glass vials for aging (2 mL or 4 mL volume, depending on sample). The glass vials were sealed with parafilm, placed in an oven at 40° C., and visually inspected on a daily basis over the aging period to ensure integrity.

Viscosity Measurements: Unless otherwise noted, suspension viscosity was measured using an AR-G2 rheometer (TA Instruments) and a 25 mm plate at 25° C. Measurements were taken at 1000 s-1 (experimental limit due to edge effects), which is below the shear rates experienced in 27-gauge needles, but in the Newtonian regime for the suspensions. Each measurement was repeated three times (about 60 s intervals between repeats) to assess short-term physical stability of the suspensions. Prior to each measurement calibration standards were recorded to validate instrument settings. The viscosity can also be calculated from the syringe force by applying the Hagan-Poiseuille equation using the flow rate of the suspension through the needle.

Syringeability Measurements: Unless otherwise noted, syringe force was measured during 0.1 mL/s ejection of a 1 mL suspension (400 mg/mL particle) using a custom force sensor apparatus and a 1-mL Norm-ject model syringe with a 27-gauge ultra-thin-wall needle (TSK).

Karl Fischer: Testing for moisture content was undertaken using Karl Fischer analysis. Approximately 100 mg of particles was heated to 105° C. in an oven and released water was determined coulometrically.

Skeletal Density: Skeletal density was measured by gas pycnometry. The gas was nitrogen or other compatible gases, and the particle mass can be 0.0413 g.

Particle Dissolution: Phosphate-buffered saline (PBS) was added to dry particle samples to produce a final concentration of 10 mg/mL (particle mass/mL of solution). Samples were placed on a VWR angular rocker with a speed setting of "35" and angle setting of "15". At 1, 10, 20, 30, 40, 50, 60, 90, and 120 minutes a 10 μL aliquot was removed from the sample vial and the absorbance at 280 nm was measured and recorded. The Ab, e.g., mAb, concentration was plotted against time for all samples.

Salt Content: Salt content was recorded by measuring sodium content using Inductively Coupled Plasma Optical Emission Spectroscopy (ICP-OES). A calibration curve was prepared using a sodium standard (ICPTraceCERT, 1000 mg/L). Quality control was completed using a diluted standard solution at 100 ppm sodium. A sample of particles (~15 mg) dissolved in 2 vol % nitric acid (10 mL) was then analyzed, resulting in an intensity lower than the instrument detection limit of ~0.5 ppm for sodium. This indicated a sodium content of less than 0.034 wt % and a total salt content (assuming sodium citrate and sodium chloride to have been removed equally) of less than 0.1 wt %.

Size Exclusion Chromatography (SEC) Measurements: 20 μL Injections of samples (1 mg/mL) were run at a flow rate of 1 mL/min in SEC buffer (25 mM phosphate, 250 mM NaCl pH 6.8) for 15 minutes on an Agilent AdvanceBio SEC (300 mm×2.7 um, 300 Å column). Peak analysis was performed by auto-integrating using the following parameters: slope sensitivity=0.5, peak width=0, height reject=0, area reject=0, shoulders off, area percent reject 0, standard tangent skim mode, advanced baseline correction, 0 for front peak skim height ratio, 0 for tail peak skim height ratio, 0 for peak to valley ratio, and 0 for skim valley ratio.

Differential Scanning Fluorimetry (DSF) Measurements: The melting temperature of the protein before and after formulation, as well as at various time points of 40° C. storage, were assessed using a QuantStudio 6 Flex instrument. Five microliters (5 μL) of samples (1 mg/mL), prepared after dialysis, were loaded onto a 96-well thermal cycler plate in quadruplicate. To each well, 12.5 μL of ultrapure deionized water and 2.5 μL of SYPRO® Orange dye (8×) were added. After a 5-minute incubation, samples were run from 25° C. to 99° C. at a ramp rate of 0.05° C./s. Melting temperature was calculated using the Protein Thermal Shift Software (Thermo Fisher, version 1.3) using a Boltzmann fit.

Circular Dichroism (CD) Measurements: The degree of preservation of the secondary structure (alpha helices and beta sheets) of the protein before and after formulation, as well as at various time points of 40° C. storage, was assessed using a Jasco J-815 instrument. Four hundred microliters (400 μL) of sample (0.5 mg/mL), prepared after dialysis, was loaded into a quartz cuvette (1 mm path length). Samples were scanned over the 190-260 nm range. Diluent buffer was used as blank subtraction for each sample. The following instrument settings were used:

Photometric mode: CD, HT
Measure range: 260-190 nm
Data pitch: 0.5 nm
Sensitivity: Standard
D.I.T.: 4 sec
Bandwidth: 1.00 nm
Start mode: Immediately
Scanning speed: 100 nm/min
Shutter control: Auto
Baseline correction: None
CD detector: PMT
PMT voltage: Auto Cation Exchange Chromatography (CIEX) Measurements: Charge variant analysis was performed for each sample on days 0, 7 and 30 under accelerated storage conditions, using an Agilent BioMAb NPS, 4.6×250 mm, PEEK ion exchange column. Samples were prepared at 1 mg/mL concentration after overnight dialysis in water. Buffer A was prepared with: 30 mM phosphate, pH: 6.3, and NaCl: 0 mM. Buffer B was prepared with: Buffer A: 30 mM phosphate, pH 6.3 plus NaCl: 175 mM. The samples were run in a gradient starting with 100% Buffer A, ramping up to a 100% Buffer B over a course of 20 min, after which the gradient was set to return to 100% Buffer A and 0% Buffer B in the next 1 min. The system re-equilibrated in 100% Buffer A for 10 min before the injection of the next sample. Integration was performed as a manual skim peak mode to reflect the Agilent data in the following protocol: https://www.agilent.com/cs/library/applications/5991-5557EN.pdf.

Flow Cytometry: 1 Million Raji cells (100 µL per well) were plated per well in a 96 well 'V-bottom' plate and 10 µL of mAb, Label, particle, or suspension at a starting concentration of 200 µL was added to the wells. The dilution factor for the mAb label, particle and suspension was 3×. The plate was incubated at 4° C. for 30 min. The plate was centrifuged at 2000 rpm for 5 min and was washed 3 times with PBS. 100 µL of PE-conjugated goat anti-human IgG was added as the secondary antibody at a 1:200 dilution. The plate was centrifuged at 2000 rpm for 5 min and was washed 3 times with PBS. The cells were then resuspended in 200 µL of cold PBS for analysis on a Life Technologies Attune NXT flow cytometer.

Scanning Electron Microscopy: Electron micrographs were collected for select samples with either a Hitachi TM3030Plus or a TM1000 tabletop microscope. The samples were immobilized on conductive tape and examined in a low-vacuum anti-charging environment, obviating the need for sample preparation.

Image Analysis: Select microscopy images were chosen for further analysis on the basis of (i) minimal particle overlapping, (ii) good contrast between the particles and the background, and (iii) a resolution providing for particle occupancies of at least 10 pixels. This allowed for particles to be easily identified and reduced resolution-based error. A binary threshold was applied to separate the particles from background, and a watershed segmentation algorithm was applied to ensure that individual particles were measured separately. The ImageJ tool "Analyze Particles" was then applied on the binary picture with the following parameters: circularity between 0.5 and 1.0; size between 5 and infinity square microns; exclude on edges; fill holes. The outlines of the identified particles were overlaid onto the original image. Particles which were misidentified, such as clusters that were identified as a single particle or particles whose outlines do not match the particle, were then discarded. Missing particles were measured by manually tracing the particle's outline and using ImageJ's Measure tool.

Density Analysis: The skeletal density of particles from select samples was determined by examining approximately 0.1 g of powder with an AccuPyc II 1340 gas displacement pycnometry system.

Water Content Analysis: The residual moisture in particles from select samples was determined by placing approximately 0.1 g of powder in an oven with a Karl Fischer titrator and heating the sample.

ELISA Assay: ELISA assay was used on select samples to detect human antibody in a denaturation sensitive manner. Human IgG was first plated in PBS for 1 hour, followed by washing with wash buffer (PBS+0.05% Tween20) three times for 4 minutes, followed by blocking with 2% BSA (Sigma) in wash buffer for 45 minutes, followed by incubation with dilute (20 µg/mL) protein A-HRP (Abcam) for 45 minutes, followed by wash buffer three times for 3 minutes, followed by incubation with TMB (Abcam) for 10 minutes, finally followed by quenching of the reaction with STOP solution (Abcam). The colorimetric readout was conducted on a Thermo Multiskan Spectrum.

Subvisible Particle (SvP) Analysis: Subvisible particles (SvPs) were analyzed with a Fluid Imaging Technologies FlowCam PV-100 system. Samples for analysis were reconstituted in sterile centrifuge tubes with filtered water (Milli-Q) to the concentration of interest. Three sets of samples were investigated thereafter. These included (i) a sample of the diluent used for reconstitution, (ii) an aliquot of the feed solution used for the particle formation process, i.e., a sample of the first liquid, and (iii) the reconstituted material.

Accelerated Storage: Unless otherwise noted, storage was carried out under accelerated conditions for select samples by maintaining them at an elevated temperature (40° C.) for defined periods of time in an incubator or oven. Samples were kept in 2 mL or 4 mL Wheaton glass vials and sealed with paraffin film.

Helium Ion Microscopy (HIM): Ion micrographs were collected for select samples using an HIM instrument. The source energy, working distance, and aperture size were typically, 29 keV, 9 mm, and 10 microns, respectively. For select samples, a focused gallium ion beam was used to section particles for analysis of the internal structure. Tilted samples were ablated with a source current, dwell time, and cut spacing of 300 pA, 0.5-1 µs, and 2-5 nm, respectively.

X-Ray Photoelectron Spectroscopy (XPS): A small amount of powder was deposited onto hydrocarbon tape attached to a piece of silicon wafer and gently pressed to form a compact uniform bed. Excess loose powder was removed by lightly tapping the edge of the wafer piece. Specimens were prepared just before analysis. XPS measurements were performed with a Kratos Axis Ultra spectrometer using monochromatic Al Kα X-rays (1486.6 eV). For each sample, a survey spectrum was acquired from an area of approximately 2 mm by 1 mm (pass energy=160 eV; 225 W power), from which the surface elemental composition was determined. Charge compensation was achieved using a beam of magnetically focused electrons as a flood current. The standard photoelectron take-off angle used for analysis is 90° giving a sampling depth in the range 5-8 nm. The surface elemental compositions were analyzed using a quantification model that assumes homogeneity of the probed sample volume.

Inverse Gas Chromatography (IGC): Powdered samples were analyzed using inverse gas chromatography. Cylindrical columns were packed with 200 to 300 mg of powdered samples to make up a stationary phase. Following an inert gas purge, a series of gas probes was injected on the column. Determination of the retention volume for each probe enabled evaluation of the dispersive and polar components of the surface energy for each sample.

X-Ray Diffraction (XRD): Samples were packed into 0.7 mm diameter glass capillaries. The powder patterns were measured on a PANalytical Empyrean diffractometer equipped with an incident-beam focusing mirror and an X'Celerator detector. The patterns (1-50° 2θ, 0.0167113° steps, 4 sec/step, ¼° divergence slit, 0.02 radian Soller slits) were measured using Mo Ká radiation. If static electricity effects (for the case of evaluating a lyophilization control this occurred after grinding in a mortar and pestle) prevented packing the sample into a capillary, its powder pattern was measured from a flat plate specimen on a Bruker D2 Phase diffractometer equipped with a LynxEye position-sensitive detector. The pattern was measured using Cu Kα radiation from 5-100° 2θ in 0.0202144° steps, counting for 1.0 sec/step. The standard instrument settings (30 kV, 10 mA, 0.6 mm divergence slit, 2.5° Soller slits, and 3 mm scatter screen height) were employed.

Microflow Particle Sizing (MPS): Flow imaging microscopy for particle size analysis was carried out using a FlowCam PV-100. To investigate size and dispersity of particles, 5 mg of powder were dispersed in 10 mL of dry isopropanol via sonication. The isopropanol continuous phase prevented the particles from dissolving, i.e., prevented reconstitution. 0.3 mL was injected into the cell and images of the particles were taken using a flow rate of 0.15 mL/minute. Particles with a circularity greater than 0.9 were reported in the analysis and any double images were removed from the analysis, to give a size distribution and dispersity of particles in the range from 1 to 100 μm.

Dynamic Vapor Sorption (DVS): Powders were analyzed using dynamic water vapor sorption. Approximately 50 mg of powdered sample was loaded into the pan of the instrument's microbalance. The sample was held isothermally at 22° C. and the sample mass was monitored throughout the measurement. Following a 0% RH purge to remove surface water, the relative humidity (RH) in the sample chamber was ramped at a constant rate of 4% RH per hour up to 90% RH. The sample was held at 90% RH for one hour, then the RH was reduced to 0% as a step change. The sample was held at 0% RH for one hour, after which the measurement was terminated.

Dynamic Scanning calorimetry (DSC): Powdered samples were analyzed using dynamic scanning calorimetry. Masses of 5 to 10 mg of powdered samples were loaded into aluminum crucibles and sealed hermetically. Crucibles were loaded into the instrument, and the heat flow into the samples was monitored while the temperature was ramped from 30 to 250° C. at a constant rate of 5° C./minute.

Antibody-Dependent Cell-Mediated Cytotoxicity (ADCC): 12,500 Cells per well at a 25 μL volume of Raji cells were plated in 96 well plate, followed by addition of 25 μL of mAb with a starting concentration of 2 μg/mL was added and a 3× serial dilution was made thereon. 75,000 cells per well at a 25 μL volume per well of Effector cells were added and the plate was incubated at 37° C. for 6 h in an incubator. The plate was then equilibrated at RT for 15 min. 30 μL Luciferin reagent was added to each well. The luminescence was measured using a Thermo Scientific Varioskan LUX luminometer.

USP <790>: According to the USP <790> standard, samples of dissolved particles were visually observed against a white and black background under lighting conditions greater than 2000 lux. Matte-finished high density polyethylene sheets were selected for the background to reduce glare. The illuminance at the viewing point was confirmed with a lux meter (Dr. Meter, LX1330B). The samples were swirled before being held up to the backgrounds and viewed for 5 sec.

Example 1. Generation of Ab Particles in the Target Size and Dispersity Ranges Rituximab or human IgG particles were formed and 10 mg of particles were provided for analysis. The average particle size, D10, D50 and D90 were reported based on particle size analysis (FlowCam™), count-weighted. The particles had the following characteristics: average size between 4-25 μm; D90<35 μm; mean diameter=6.42 μm; and D10/D50/D90=4.67/6.36/8.23 μm. Based on these studies, the particles satisfied the required criterion.

Example 2. Determination of the Average Particle Size of the Ab Particles

SEM of the rituximab or human IgG particles for each batch was obtained. Images were taken at 1000× magnification. The image processing and statistics were performed using ImageJ analysis, count-weighted. The average particle size of the particles, D10, D50 and D90 was determined to have an average particle size between 5-25 μm and D90<35 μm. The particles had the following particle size statistic: mean diameter=5.18 μm; and D10/D50/D90=3.82/5.07/6.70 μm. Based on these studies, the particles satisfied the required criterion.

Example 3. Generation of Stable Ab Particle Compositions with High Concentration and Low Viscosity The units "mPa·s" and "cP" are used herein interchangeably in the broadest sense.

Rheology: A suspension of rituximab or human IgG particles was created with the following characteristics: protein loading >250 mg/mL and apparent viscosity <20 cP (mPa·s). The viscosity was measured using a parallel plate rheometer or other methods that are known in the art. Suspensions were prepared in two different carriers at various concentrations. Carrier A is approved in a marketed drug in the EU. Carrier B has not been approved in any marketed drugs, but is in the same chemical family as Carrier A, with a lower viscosity and favorable toxicity profile. In Carrier B, Ab concentrations reached over 300 mg/mL at 20 cP (mPa·s), satisfying the criterion. When lower viscosity carriers are considered, even higher concentrations can be achieved.

Rheology (days 0, 7, 30 at 40° C.): The viscosity of the suspension of particles over time was tracked to ensure that it does not vary by more than 5% over 7- and 30-day accelerated storage. At each time point, the suspension had a viscosity <20 cP (mPa·s) with a protein loading >250 mg/mL. The concentration condition was met based on the preparation of a 280 mg/mL protein suspension. The Day 0 sample was measured immediately. Day 7 and Day 30 samples were aged according to the aging procedure outlined above. Measurements were taken at shear rates of 1000 $s^{-1}$. At Day 0, the viscosity of the suspension was measured at 16.87 cP. On Day 7, the viscosity reduced to 16.33 cP. At Day 30, the viscosity increased 29% as compared to Day 0 to 21.83 cP, and is slightly above the 20 cP limit. However, using such a small plate (25 mm), small instrument gap (150 microns), and small sample volume, it has been estimated that error in the measurement could be as high as 30%.

Syringeability: The force of syringing the suspension through a needle was measured and verified that the syringe force remained below 30 N. A suspension of rituximab or human IgG at 280 mg/mL protein (400 mg/mL particle) was loaded into a syringe with a 27-G needle. The resulting force was recorded and plotted against the volume. For reference, the force of actuating an empty syringe equipped with a syringe needle using a 15 mPa·s standard was compared and the results showed that the syringe forces were all below 30 N.

Karl Fischer Titration: The water content of the solid particles was determined to define the component make-up of the particles using Karl Fischer titration. The water content of the particles was measured, recorded and determined to be 1.89 wt %.

Density: The density of the solid particles using skeletal density analysis was determined and measured to be 1.3 g/cm³. Thus, the high density for the particles allows for optimal dose loading per particle.

Salt: The NaCl content of the solid particles was determined to define the component make-up of the particles. The salt content was measured and recorded to be <0.1 wt %.

Dissolution: The dissolution rates were recorded for each formulation on days 0, 7 and 30. Dissolution was recorded at various time points which confirmed dissolution of the particles within ~20 minutes and ~60-80 minutes for the suspension. The particles and suspension were dissolved in PBS to a final concentration of 10 mg/mL and rocked on a rocker. Dissolution of particles on days 0, 7 and 30 were also stored at 40° C.

USP<790>: The presence of visible particles was determined in dissolved samples of particles. USP <790> was used to determine if there were particles present in the "visible" range (>100 um). Observations of dissolved formulations were used to assess the presence of visible particles. The observations were made briefly (5 seconds) with a white and black background under the appropriate lighting. Some potential small particles were observed, but were difficult to see by eye likely classifying them as subvisible particles. Given that these particles may be considered subvisible, other methods have been used to further investigate as described below.

Sub-visible Particle Analysis: The subvisible particle matter present in dissolved particles was investigated. Subvisible particle analysis was performed after dissolution of the particles. This data was compared to other competitive particle formation technologies. The SvP analysis was performed by a particle analyzer where the particle count adjusted for background signal in the control sample. The subvisible particle counts measured in the samples were lower than any other completing technology including standard lyophilization.

Example 4. Investigation of Changes in Protein Structure after Particle Formation and Stability (Days 0, 7, 30 at 40° C.) by Structural Assays Size Exclusion Chromatography (SEC): The objective was to collect SEC data to assess the degradation of the protein monomers through processing and storage at 40° C. for 30 days. SEC was performed based on the FDA-label, particles and suspensions. The monomer, aggregate and fragment data for each sample was obtained. The SEC data was recorded and demonstrated good stability of protein monomers through processing and storage on day 0, 7 and 30 after storage at 40° C. The 30-day sample for the FDA label had poorer preservation of the monomers as compared to the particle and suspension formulations, which each had >98% preservation of monomers. The small increase in aggregates incurred through processing of particles can be addressed through improved formulation as described below.

Formulation: An additional formulation was designed with lower polysorbate, histidine and higher salt content, with the goal of reducing the small initial increase in aggregates after the particle processing step. The initial decomposition of matter was reduced through a slight modification of the formulation through lowering the amount of polysorbate 80 and reintroducing a fraction of the salt removed through desalting. The data indicated an almost unmeasurable difference in aggregates and monomer change through processing and demonstrated lower accumulation of aggregates (~0.1%) through processing.

Differential Scanning Fluorimetry (DSF): The objective was to produce protein particle and suspension formulations with <2° C. shifts in melting temperature as compared to the FDA-label formulation after 30 days of storage at 40° C. DSF was performed on the FDA-label, particles, and suspensions on day 0, 7 and 30 after storage at 40° C. The data showed a less than 1° C. shift in melting temperature was observed across all samples. Shifts up to 2° C. were generally recognized as insignificant.

Circular Dichroism (CD): The objective was to confirm that the secondary structure of the protein particle formulation was preserved through processing and storage. The success criteria were to have significant overlap with the FDA-label CD data and to report the beta-sheet percent for each sample. The data for all time points was confirmed to have significant overlap with beta sheets being reported. The time 30 day highlighted the similarity in the beta sheet structure represented by a trough observed at 217 nm. The CD data was obtained and compared to demonstrate significant overlap as well as beta sheet percentage among all samples tested for all time points.

Cation Exchange Chromatography (CIEX): CIEX data was collected to assess the distribution of charge variant species and their changes through processing and storage at 40° C. for 30 days. CIEX was performed on the FDA-label, particles and suspensions. The acidic, main, and basic species data for each sample was obtained and analyzed. Select CIEX data points highlighted the acidic shift that was experienced by the label formulation compared to the absence of such a shift in the solid particles after 30 days of aging. The particles resemble the unprocessed material whereas the label formulation experienced degradation. The CIEX data was recorded as proposed and demonstrated good stability of charge variants through processing and storage on day 0, 7 and 30 after storage at 40° C. The 30-day sample for the FDA-label had a drastically poorer preservation of the charge variant distribution as compared to the particle and suspension formulations due to an acidic shift in variants.

Aggregation, Fragmentation and Change in Charge Variants of the Protein: Generally, aggregation and fragmentation data was collected using Size Exclusion Chromatography (HPLC-SEC) unless otherwise noted. Strong Cation Exchange Chromatography (CIEX) was used to collect the distribution of charge variant species and their changes unless otherwise noted.

Example 5. Investigation of Ab Activity after Particle Formation and Stability (Days 0, 7, 30 at 40° C.) by In Vitro Functional Assays Flow Cytometry: The objective was to produce particle and suspension formulations with >95% preservation of binding activity as compared to the FDA-label formulation after 30 days of storage at 40° C. Flow cytometry was performed on the FDA-label, particles, and suspensions on day 0, 7 and 30 after storage at 40° C. Each data point was generated in triplicate with a mean and error bars that represented the standard deviation. All samples demonstrated that no significant difference among the samples for each time point was observed and that there was >95% preservation of binding activity.

Antibody-Dependent Cellular Cytotoxicity (ADCC): The objective was to produce protein particle and suspension formulations with >95% preservation of ADCC activity as compared to the FDA-label formulation after 30 days of storage at 40° C. ADCC was performed on the FDA-label, particles, and suspensions on day 0, 7 and 30 after storage at 40° C. Each data point was generated in triplicate with a mean and error bars that represented the standard deviation. On day 0 there was a slightly lower signal for the protein particles and suspension as compared to the FDA-label, which is consistent with the slight loss of protein monomers incurred through initial processing. Over the course of the 30 days, the more stable solid formulations (particle and suspension) were able to preserve their function, consistent with their better preservation of monomers and charge variants compared to the FDA-label formulation and leading to the outperformance of the particle and suspension formulations over the FDA-label formulation.

Example 6. Syringeability

The average glide force was plotted against particle suspension concentrations of up to 650 mg/mL. The data was fitted using the Krieger-Dogherty model of concentrated suspensions of solid and spherical particles. 20 N (Newtons) was accepted as the reference to typical glide force limits.

27-gauge UTW needle: Protein particle suspensions were created at a range of concentrations from 0 to 650 mg/mL using an oily carrier as the liquid phase. A ISO-standard 1 mL long prefillable syringe was filled with 1 mL of suspension with a pipette. A 27-gauge UTW 13 mm (half-inch) needle (Japan Bio Products) was attached to the syringe. Before applying compression, each syringe had air bubbles pushed out and was shaken by hand for 10 seconds. A texture analyzer (Mark-10 ESM303) used to apply steady compression to the syringe plunger at a rate of 189.4 mm/min, which correlates to a volume ejection rate of 0.1 mL/s. The glide force was identified for each suspension concentration.

30-gauge UTW needle: A protein particle suspension of 300 mg/mL was created using 15% PEG as an aqueous carrier and as the liquid phase. A 1 mL luer-lock syringe (BD) was filled with 0.25 mL of suspension with a pipette. A 30-gauge UTW 13 mm (half-inch) needle (Japan Bio Products) was attached to the syringe. Before applying compression, each syringe had air bubbles pushed out and was shaken by hand for 10 seconds. A load cell (Honeywell FSS1500NST) was placed on a linear actuator and this system was used to apply steady compression to the syringe plunger at a rate of 111 mm/min, which correlates to a volume ejection rate of 0.033 mL/s. The glide force was identified for each suspension concentration. The glide force in this case was identified to be 11.5 N.

Suspension Syringe Force and Viscosity: The Mark-10 was prepared to measure the force of pushing a 1 mL long syringe at 0.1 mL/s. The suspension was redispersed in the vial by shaking for 30 seconds. The vial was checked for any particle agglomerates or non-dispersion. The cap was removed and a pipette was used to load 1 mL of suspension into a 1 mL long syringe. A West NovaPure stopper was added and air was pushed out of the syringe. A 27 g UTW needle (Japan BioProducts) was added into the luer-lok of the syringe. The syringe was loaded into the Mark-10 and the force-translation profile was measured. A blank syringe was also used in order to measure the blank force. Generally, viscosity was measured using plate-and-cone geometry methods. The cone was 25 mm and had a 3-degree angle. The measurement was performed at 950 1/s.

Example A: A 1 mL long syringe (inner diameter 6.35 mm) was filled with 1 mL of suspension with an ethyl oleate carrier and a protein (Ab) particle loading of 642 mg/mL and a viscosity of about 94 mPa·s. The syringe was stopped with a fluoropolyer coated stopper (West Novapure). A 27 g×13 mm UTW needle (Japan BioProducts) was attached to the luer-lok of the syringe. A Mark-10 was used to apply a flow rate of 0.1 mL/sec and measure the force profile. The glide force was 22.69 N.

Example 7. Pharmacokinetics (PK): Both Subcutaneous Formulations have Similar Bioavailability in Comparison to the IV Dose Formulation: The scope of the study involves four cohorts having the following formulations, 1) IV Ab Aqueous: 20 mg/mL Rituximab (anti CD-20 antibody), 4 mg/mL Histidine, 1 mg/mL Trehalose, 0.7 mg/mL Sodium Chloride and 0.6 mg/mL Polysorbate 80, 2) SC Ab Aqueous: 20 mg/mL Rituximab (anti CD-20 antibody), 4 mg/mL Histidine, 1 mg/mL Trehalose, 0.7 mg/mL Sodium Chloride and 0.6 mg/mL Polysorbate 80, 3) SC Ab particle composition: 20 mg/mL Rituximab (anti CD-20 antibody), 4 mg/mL Histidine, 1 mg/mL Trehalose, 0.7 mg/mL Sodium Chloride and 0.6 mg/mL Polysorbate 80 formulated into the particle composition which were then suspended in Ethyl Oleate (non-Aqueous carrier vehicle). The concentration of the suspension was 20 mg/mL; and, 4) SC Suspension vehicle: Ethyl Oleate (non-Aqueous carrier vehicle).

Animals: Female wild-type Albino Sprague Dawley Rats (Charles River Lab) were housed in the animal facility at the Tufts University Comparative Medicine Services (Tufts CMS). All use of animals described were conducted in compliance with the National Research Council's "Guide for the care and use of laboratory animals" and performed following detailed written protocols that were approved by the Institutional Animal Care and Use Committee (IACUC).

Dosing, Study Design and Analysis: All particle composition injections were accomplished using a 100 µL Hamilton glass syringe with a 27-gauge needle. All aqueous and non-aqueous vehicle injections were accomplished using a 300 µL insulin syringe with staked-in 30-gauge needle. A vortexing protocol was implemented to resuspend the particles in the syringe thoroughly in the case of the suspension doses. After loading the suspension, each syringe was vortexed for 5 seconds each with the needle facing up, followed by needle facing down and finally a horizontal position vortexing step immediately prior to injecting the animals, which prevents any loss of dose due to settling and ensures dose accuracy. Sprague Dawley Rats were used for this study. The following study design was used: 1) IV Ab Aqueous: Dose=10 mg/kg; Volume=100 µL; n=4, 2) SC Ab Aqueous: Dose=10 mg/kg; Volume=100 µL; n=5, 3) SC Ab Particle composition: Dose=10 mg/kg; Volume=100 µL; n=5, 4) SC Suspension vehicle: Volume=100 µL; n=3. Plasma samples were collected at 0 h, 3 h, 6 h, 9 h, 1 d, 2 d, 3 d, 4 d, 5 d, 6 d, 7 d, 9 d, 12 d, (14 d, 16 d, 19 d, 21 d and 23 d: These time points were below the limit of detection of the assay utilized). The blood from each rat was collected in EDTA capillary tubes (purple) from tail vein bleeds at all data points. The plasma obtained from the blood was diluted to 10,000× for analysis using ELISA. Plasma samples were assessed using anti-human IgG ELISA assay by third party contract research organization (Ray Biotech: RayBio® Human IgG ELISA Kit).

Example 8. Efficacy: Subcutaneous Formulations Demonstrate Similar Efficacy in a Xenograft Model Formulation: The scope of the study involves three cohorts having the following formulations: 1) Untreated: No drug or placebo was injected, 2) SC Ab Aqueous: 2 mg/mL Rituximab (anti CD-20 antibody), 0.4 mg/mL Histidine, 0.1 mg/mL Trehalose, 0.07 mg/mL Sodium Chloride and 0.06 mg/mL Polysorbate 80, and 3) SC Ab particle composition: 20 mg/mL Rituximab (anti CD-20 antibody), 4 mg/mL Histidine, 1 mg/mL Trehalose, 0.7 mg/mL Sodium Chloride and 0.6 mg/mL Polysorbate 80 formulated into particles which were then suspended in Ethyl Oleate (non-Aqueous carrier vehicle). The concentration of the suspension made was 20 mg/mL.

Animals: CR female CB.17 SCID mice (Charles River Labs) were housed in the animal facility at Charles River Labs. All animal procedures were formally reviewed and approved by the Institutional Animal Care and Use Committee (IACUC) at the Charles River Labs.

Cell Culture: DOHH2 human B-cell Lymphoma cells (DSMZ) were maintained in Roswell Park Memorial Institute (RPMI) media containing 10% fetal bovine serum (FBS) and 1% penicillin G/streptomycin.

Tumor Xenograft Model: DOHH2 human B-cell Lymphoma cells were collected at 70% confluency and administered subcutaneously (SC) in the flank of female CB.17 SCID mice. 1×107 DOHH-2 tumor cells in 0% Matrigel were injected at a cell injection volume of 0.1 mL/mouse. A pair match was performed when tumors reached an average size of 80-120 mm3 before the treatment was begun.

Dosing, Study Design and Analysis: All particle composition injections were made using a 100 μL Hamilton glass syringe with a 27-gauge needle and all aqueous injections were made using a 300 μL insulin syringe with staked-in 30-gauge needle. A vortexing protocol was implemented to resuspend the particles in the syringe thoroughly in the case of the suspension doses. After loading the suspension, each syringe is vortexed for 5 seconds each with the needle facing up, followed by the needle facing down and finally a horizontal position vortexing step immediately prior to injecting the animals. This prevents any loss of dose due to settling and ensures dose accuracy. Fox Chase SCID mouse with DOHH2 cell xenograft model (Charles River Labs) was used in this study. The following study design was used: 1) Untreated: n=12, 2) SC Ab Aqueous: Dose=10 mg/kg; Volume=100 μL; Dosing frequency: 2× weekly, n=12, and 3) SC Ab composition: Dose=10 mg/kg; Volume=10 μL; Dosing frequency: 2× weekly, n=12. Tumor volume measurements were done using calipers and measurements were made biweekly. Tumor volume was calculated using the following formula: $V (mm^3)=(L*W^2)/2$.

Example 9. Biodistribution: Formulations Demonstrate Complete Absorption from the SC Injection Site and Similar Biodistribution Compared to the Standard Aqueous mAb Design: Sprague Dawley rats were purchased from CRL for the purpose of this study. The scope of the study involved 4 cohorts viz. Rituximab aqueous IV injection, Rituximab aqueous SC injection, Rituximab composition SC injection and a vehicle control SC injection. The study was a single-dose study where the animals were dosed with approximately 100 μL of 10 mg/kg drug or vehicle only in the case of the vehicle control. The volume of the injection was weight adjusted in the case of each injection. Plasma samples were collected and analyzed for the following time points: 0 h, 3 h, 6 h, 9 h, 1 d, 2 d, 3 d, 5 d, 6 d, 7 d, 9 d, 12 d, 14 d, 16 d, 19 d, 21 d and 23 d. A human IgG ELISA kit (RayBio® Human IgG ELISA Kit) was used to analyze the bioavailability of the protein from the plasma sample.

Dosing and Resuspension: All the aqueous and vehicle injections were made using a 300 μL insulin syringe while the suspension injections were made using a 100 μL glass Hamilton Gastight syringe with a 27-gauge ultra-thin wall (UTW) needle. A vortexing protocol was implemented to resuspend the particles in the syringe thoroughly in the case of the suspension doses. The protocol involves loading and vortexing the syringes for 5 seconds each with the needle facing up, followed by needle facing down, and finally a horizontal position vortexing step immediately prior to injecting the animals. This ensures dose accuracy and prevents any loss of dose due to settling.

Plasma Collection and Processing: The blood from each rat was collected from tail vein bleeds at all the data points. The plasma obtained from the blood was diluted to 10,000× for analysis using ELISA. Sandwich ELISA was performed using the RayBio® Human IgG ELISA Kit by Raybiotech.

Results: The data obtained showed that particle composition had nearly the same bioavailability (within margin of error) as that of the aqueous Rituximab delivered subcutaneously. The bioavailability of the two subcutaneous arms of the study in comparison to the aqueous Rituximab IV arm was about 40%, which was similar to the findings of previous studies and as indicated in the literature. Data up till day 12 from the 23-day study indicates that the plasma concentration of the drug falls below the limit of detection of the assay post day 12. The signal from the vehicle control was also found to be below the limit of detection of the assay and hence deemed as the background noise. These studies have demonstrated a PK profile in two species of rodents, indicating that the particle composition delivered by SC injection has a similar effect in tumor reduction as compared to the aqueous Rituximab formulation also delivered by SC injection.

Example 10. Safety and Toxicity: Single Dose Mouse Pathology Findings Indicate No Toxicity or Pathology Among Animals from all Groups Formulation: The scope of this study involved two cohorts having the following formulations: 1) SC high concentration human mAb Aqueous: 20 mg/mL Rituximab (anti CD-20 antibody), 4 mg/mL Histidine, 1 mg/mL Trehalose, 0.7 mg/mL Sodium Chloride and 0.6 mg/mL Polysorbate 80. The aqueous formulation was then concentrated to 141.54 mg/mL to form the high concentration version of the formulation. 2) SC Ab composition: 20 mg/mL Rituximab (anti CD-20 antibody), 4 mg/mL Histidine, 1 mg/mL Trehalose, 0.7 mg/mL Sodium Chloride and 0.6 mg/mL Polysorbate 80 formulated into particles which were then suspended in Ethyl Oleate (non-Aqueous carrier vehicle). The concentration of the suspension was 300.88 mg/mL.

Animals: Male (castrated) Yucatan Pigs (S&S Farms, Constantine, MI) were housed in the animal facility at CBSET, Inc. All animal procedures were formally reviewed and approved by the Institutional Animal Care and Use Committee (IACUC) at CB SET, Inc.

Dosing, Study Design and Analysis: All injections were made using plastic BD Luer lock syringes used with a 27-gauge needle. A vortexing protocol was implemented to resuspend the protein particles in the syringe thoroughly in the case of the suspension doses. After loading the suspension, each syringe is vortexed for 5 seconds each with the needle facing up, followed by the needle facing down and finally a horizontal position vortexing step immediately prior to injecting the animals. This prevents any loss of dose due to settling and ensures dose accuracy. Yucatan (male) pigs were used for this study. The following study design was used: 1) SC high concentration mAb Aqueous: Dose=10 mg/kg; n=1, and 2) SC Ab Aqueous: Dose=6 mg/kg and 14 mg/kg; n=2. Plasma samples were collected at 0 h, 2 h, 4 h, 8 h, 12 h, 1 d, 3 d, 5 d, 7 d, 10 d, 14 d, and 18 d. The blood from each pig was collected in EDTA capillary tubes at all data points. The plasma obtained from the blood was diluted to 10,000× for analysis using ELISA. Plasma samples were assessed using anti-human IgG ELISA assay by third party Contract Research Organization (Ray Biotech: RayBio® Human IgG ELISA Kit).

Example 11. Immunogenicity

Formulation: The scope of the study involves four cohorts having the following formulations: 1) SC mAb Aqueous: 20 mg/mL Rituximab (anti CD-20 antibody), 4 mg/mL Histidine, 1 mg/mL Trehalose, 0.7 mg/mL Sodium Chloride and 0.6 mg/mL Polysorbate 80; 2) SC mAb composition: 20 mg/mL Rituximab (anti CD-20 antibody), 4 mg/mL Histidine, 1 mg/mL Trehalose, 0.7 mg/mL Sodium Chloride and 0.6 mg/mL Polysorbate 80 formulated into particles which were then suspended in Ethyl Oleate (non-Aqueous carrier vehicle); and 3) SC Suspension vehicle: Ethyl Oleate Placebo.

Animals: Female wild-type Balb/c mice (Charles River Labs) were housed in the animal facility at Tufts University Comparative Medicine Services (Tufts CMS). All animal procedures were formally reviewed and approved by the Institutional Animal Care and Use Committee (IACUC) at the Tufts CMS.

Dosing, Study Design and Analysis: All particle composition injections were made using a 100 μL Hamilton glass syringe with a 27-gauge needle. All aqueous and non-aqueous vehicle injections were made using a 300 μL insulin syringe with staked-in 30-gauge needle. A vortexing protocol was implemented to resuspend the particles in the syringe thoroughly in the case of the suspension doses. After loading the suspension, each syringe is vortexed for 5 seconds each with the needle facing up, followed by needle facing down, and finally in a horizontal position vortexing step immediately prior to injecting the animals. This prevents any loss of dose due to settling and ensures dose accuracy. Balb/c female mouse at 10 weeks (Charles River Lab) was used for this study. The following study design was used: 1) SC mAb Aqueous: Dose=10 mg/kg; Volume=100 μL; n=4, 2) SC mAb composition: Dose=10 mg/kg; Volume=10 μL; n=4, 3) SC Suspension vehicle: Volume=10 μL; n=2. Plasma samples were collected at 0 d, 7 d, 14 d, 18 d and 42 d. The blood from each mouse was collected in EDTA capillary tubes from facial vein bleeds at all data points. The plasma obtained from the blood was diluted to 2,500× for analysis using Meso Scale Discovery® Electrochemiluminescence (MSD-ECL) Platform. The master mix was made with equal concentration (0.5 μg/ml) of SULFO-TAG and biotinylated Rituximab diluted in assay diluent (1% MSD Blocker A in PBS with 0.02% Tween20). An ADA standard curve was made by serial diluting mouse Anti-Rituximab Antibody (GenScript A01970-40) at 1000 ng/mL, 333 ng/mL, 111 ng/mL, 37 ng/mL, 12 ng/mL 4 ng/mL, 1 ng/mL and 0 ng/mL. First, 50 μL of the master mix was added to each well of a round-bottom 96-well polypropylene plate. Then, 25 μL of the ADA standard or 4% plasma sample was added to each well. The plate was sealed and incubated with moderate shaking overnight at 4° C. 150 μL of Blocking Solution (3% w/v MSD Blocker A in PBST) was added to each well of a 96-well Streptavidin plate (MSD L55SA). The plate was sealed and incubated with moderate shaking for at least 30 minutes at room temperature before washing with 200 μL PBST. A 50 μL solution was transferred from each well of the polypropylene plate to the Streptavidin plate. The plate was then sealed and incubated for 1 hour at room temperature with 400-700 rpm shaking, followed by 3 washes of 200 μL PBST. 150 μL 2× Read Buffer was added to each well. The plate was analyzed using an MSD QUICKPLEX instrument.

Example 12. Turbidity

Therapeutic biologic compositions injected in patients should be essentially free of visible particles and should consist of a limited number of insoluble proteinaceous particles greater than 10 micron in size. In the present disclosure, protein microspheres in a non-aqueous suspension are envisioned to be injected into human patients. After injection into the body, an optimized formulation would result in complete dissolution of the therapeutic biologic upon contact with biological fluids in the patients' body. To mimic this dissolution behavior in-vitro, a turbidity assay is utilized routinely. Briefly, protein microspheres consisting of a therapeutic biologic and other components are exposed to a limited quantity of water to obtain a final concentration of 50 mg/mL therapeutic biologic, post-dissolution. The resulting solution is transferred to a UV transparent cuvette. Next, a UV/Vis spectrophotometer is used to measure the absorbance of the dissolved therapeutic at 50 mg/mL concentration using a 405 nm incident light. The presence of insoluble aggregates in the particles after dissolution results in an increase in the turbidity of protein formulations as compared to the monomeric form of a similar composition before processing.

To identify formulation conditions that would result in minimal change in turbidity due to processing, a scaled-down model, e.g., the particles-in-tube (PIT) method was developed. This scaled-down model is able to model protein aggregation at the process-scale while having 20-fold less material requirement and 100-fold less time requirement. This increased throughput enabled rapid and extensive screening of formulation conditions including solution pH, buffering species, surfactants, sugars, salts, amino acids, carbohydrates etc., resulting in low turbidity change during processing. The screened formulation parameters showing the most promising effect were further optimized using a customized I-optimal design of experiments (DoE) empirical model, resulting in several optimal formulations at various protein weight loadings of interest as indicated in the examples below.

Example A: A composition consisting of 70 wt % therapeutic biologic loading and 30 wt % excipients in the solid phase was developed. A composition consisting of 45 mg/mL Ab, 13.8 mg/mL Arginine hydrochloride, 1.2 mg/mL hydroxypropyl beta-cyclodextrin and 0.01 wt % PS 80 resulted in a 0.000 unit change in turbidity and 0.0% change in soluble aggregate after dissolution. Thus, the Ab molecules were completely protected from irreversible aggregation through the processing steps required to convert the monomeric form to a solid particle form.

Example B: A composition consisting of protein particles with 80 wt % therapeutic biologic loading and 20 wt % excipients in the solid phase was developed. A composition consisting of 51 mg/mL Ab, 9.0 mg/mL Arginine hydrochloride and 0.01 wt % PS 80 resulted in a 0.014 unit change in turbidity and 0.8% change in soluble aggregate after dissolution.

Example C: A composition consisting of protein particles with 85 wt % therapeutic biologic loading and 15 wt % excipients in the solid phase was developed. A composition consisting of 54 mg/mL Ab, 6.0 mg/mL Arginine hydrochloride and 0.01 wt % PS 80 resulted in a 0.034 unit change in turbidity and 1.5% change in soluble aggregate after dissolution.

Example D: Turbidity measurement was also accomplished using bicinchoninic acid as the detection reagent.

Example 13. Administration of Hyaluronidase Allows Increased Volume and Fluid Dispersion of the Composition Administered by Subcutaneous Syringe Injection Formulation: The scope of the study involves one animal having two sets of injection sites with the following formulations: Group 1 injection sites) SC Ab composition: 45.5 mg/mL human immunoglobulin G, 1.5 mg/mL mg/mL Histidine, 19.5 mg/mL L-arginine HCL, and 0.5 mg/mL Polysorbate 80 formulated into particles which were then suspended in Ethyl Oleate. The concentration of the suspension was 30 mg/mL of protein; and Group 2 injection sites) SC Ab composition administered after a hyaluronidase pre-injection: i) 150 U of hyaluronidase (Creative Biomart) in 8.5 mg/ml NaCl, 10 mM citric acid-sodium citrate, 0.9 mg/ml EDTA-2Na, 0.3 mg/ml CaCl2 pH 5.2.; ii) SC Ab composition: 45.5 mg/mL human immunoglobulin G, 1.5 mg/mL mg/mL Histidine, 19.5 mg/mL L-arginine HCL, and 0.5 mg/mL Polysorbate 80 formulated into particles which were then suspended in Ethyl Oleate. The concentration of the suspension was 30 mg/mL of protein.

Animals: The miniature pig is a preclinical model that is suitable for evaluating subcutaneous (SC) administration conditions of biotherapeutics due to its anatomical similarity to human skin and clinical translatability (Mahj et al., Exp Toxicol Path 57: 341-5,2006). Male (castrated) Gottingen Miniature Pigs (*Sus scrofa domestica*, Charles River Laboratories), Age: >3 months, were housed in the animal facility at Charles River Laboratories, Inc. and prepared for the study. All animal procedures were formally reviewed and approved by the Institutional Animal Care and Use Committee (IACUC) at Charles River Laboratories, Inc.

Dosing, Study Design and Analysis: All injections at various volumes were made using 3 mL plastic BD Luer lock syringes used with a 27-gauge needle. A vortexing protocol was implemented to resuspend the particles in the syringe thoroughly in the case of the suspension doses. After loading the suspension, each syringe is vortexed for 5 seconds each with the needle facing up, followed by the needle facing down and finally a horizontal position vortexing step immediately prior to injecting the animals. This prevents any loss of dose due to settling and ensures dose accuracy. A Gottingen (male) pig was used for this study. In the first set of injection sites, a composition of Ab containing 30 mg/mL of human immunoglobulin type G prepared according to the procedures detailed above, was subcutaneously administered into the abdominal region of an anesthetized Gottingen mini-pig until any resistance during dosing was met and if additional volume could have been administered. The average volume was 1.4 mL and the average injection rate was 0.025 mL/sec. The endpoints of the study included injection volume measurements and qualitative assessment of the injection site. In the second group of injection sites, the anesthetized Gottingen mini-pig was pre-injected with 1 mL of 2000 U/mL hyaluronidase administered into the abdominal region of an anesthetized Gottingen mini-pig. After a period of about 5-10 min, a composition of Ab containing 30 mg/mL of human immunoglobulin type G prepared according to the procedures detailed above, was subcutaneously administered into the abdominal region of an anesthetized Gottingen mini-pig until any resistance during dosing was met and if additional volume could have been administered. The average volume was 2.2 mL and the average injection rate was 0.045 mL/sec. The endpoints of the study included injection volume measurements for the composition of Ab injections and injection rates and qualitative assessment of the injection site. All injections were conducted using the same injection force.

Results: The objective of this study is to determine the maximum feasible volume that can be dosed when given subcutaneously as a single dose to minipigs. The experiments indicate that the injection volume of the Ab particle compositions that were subcutaneously administered can be increased by pre-injection with hyaluronidase and these hyaluronidase injected sites showed improved rates of injection of the Ab particle composition as determined by the appearance of the skin bleb formed at the site of treatment and the time and volume of the injection.

Example 14. Needle Free Jet Injection

Formulation: Human IgG particles having a mean size of about 30 μm was suspended in corn oil. The mass of the particles was measured and mixed with the appropriate volume of corn oil to yield the desired concentrations of 125 mg/mL and 200 mg/mL of protein. 125 mg/mL: Weight of particles (g) 0.5; Volume of corn oil (mL) up to 4 mL. 200 mg/mL: Weight of particles (g) 0.97; Volume of corn oil (mL) up to 5 mL.

Study Design and Analysis: A needle-free jet injection device with a pore size of about 250 μm (PharmaJet, Cambridge, MA) was calibrated to deliver the particles in corn oil formulation. The needle-free jet injection device was loaded and was prepared for injection. A formulation at both concentrations (125 mg/mL and 200 mg/mL) was injected into a gel that was used to simulate subcutaneous and intramuscular tissue depth, and to demonstrate repeatability of the injection depth and shape. First, both formulations were injected into the gel having a known injection profile. Next, a saline solution containing a blue dye was injected into the gel which provided calibration for subcutaneous and intramuscular tissue depth. The results showed that the injections for each concentration of particles in corn oil matched the injection depth profile and shape of the blue dye saline injection in the gel. These findings demonstrate that the particle formulations are compatible for use with needle-free jet injection devices.

Example 15. Particle and Suspension Quality Studies

Design: The stability of the protein particle suspensions was assessed over the course of three months at 5, 25, and 40° C. to determine the stability of the particle formulations in comparison to the protein liquid drug substance (LDS).

Formulation: Composition: 300-400 mg/mL protein, 67-77% protein by mass, 21.55-15.05 mg/mL excipients formulated into particles which were then suspended in Ethyl Oleate.

Buffer Exchange by Tangential Flow Filtration (TFF): Protein feed solutions were prepared by diafiltration into the required buffer cocktails. A KrosFlow KR2i TFF system (Repligen) equipped with a hollow fiber filter module (MiniKros Sampler) was used to perform the feed preparation. A number of diafiltration volume exchanges were performed with the appropriate buffer for each formulation.

SEM Imaging: The particles were imaged using a scanning electron microscope (Hitachi, TM-1000). A sample of the particles was mounted onto an adhesive stage for analysis. Images were captured at varying magnifications using an accelerating voltage of 15 kV.

Karl Fischer Coulometry: Testing for moisture content was performed by Karl Fischer analysis using a MetroOhm (899 coulometer) equipped with an 860 KF Thermoprep oven. Particles were heated to 165° C. in an oven and the released water was determined coulometrically.

Particle Dissolution: Water was added to dry particle samples to produce a final protein concentration. Samples are placed on a nutating mixer at 60 RPM for a period of time. The terminal dissolution concentration was recorded by removing an aliquot from the sample and measuring the absorbance at 280 nm (using the extinction coefficient E1%=1.69 L·g–1·cm-1).

Turbidity: An aliquot of reconstituted particle solution was transferred to a 1-cm path length cuvette. The absorbance at 405 nm was recorded using a NanoDrop™ One UV-VIS spectrophotometer (Thermo Scientific).

Size-Exclusion Chromatography (SEC) Measurements: Injections of samples were run at a flow rate of about 0.35 mL/min using a mobile phase comprised of 100 mM sodium phosphate monobasic and 200 mM L-arginine monohydrochloride, pH 6.5 for 10 minutes on a Tosoh TSKgel SuperSW mAb HTP (4.6 mm ID×15 cm L) column. Peaks were manually inspected to ensure accurate identification and analysis was performed by autointegration using parameters known in the art.

Strong Cation-Exchange Chromatography (SCEX): Injection of samples dissolved in milli Q water were run at a flow rate of 0.4 mL/min using a gradient method that starts at 100% mobile phase pH gradient buffer A to 100% mobile phase pH gradient buffer B followed by washing and re-equilibration for a total run time of 40 minutes on a MAbPac™ SCX-10 RS Analysis Column, 2.1 mm ID×15 cm L, 5 μm column. Peaks were manually inspected to ensure accurate identification and analysis was performed by autointegration using parameters known in the art.

Hydrophobic Interaction Chromatography (HIC): Injection of samples dissolved in diluent comprised of 750 mM Ammonium Sulfate, 50 mM Sodium Phosphate Monobasic Dihydrate, pH 6.0 (1 mg/mL) were run at a flow rate of 1 mL/min using a gradient method that starts at 50% mobile phase A comprised of 2M ammonium sulfate, 50 mM sodium phosphate monobasic dihydrate, pH 6.0 to 100% mobile phase B comprised of 50 mM sodium phosphate monobasic dihydrate, pH 6.0 followed by washing and re-equilibration using 50% mobile phase A for a total run time of 60 minutes on a MAbPac™ HIC-20 HPLC Column, 5 μm, 4.6 mm ID×25 cm L column. Peaks were manually inspected to ensure accurate identification and analysis was performed by autointegration using parameters known in the art.

Particle Sizing (Laser Diffraction): Particle size analysis was conducted via laser diffraction using a Horiba LA-960S. Dry particles were suspended in isopropyl alcohol at a concentration of approximately 0.1 mg/mL. The Particle suspension was sonicated within the particle measurement instrument to ensure homogeneity and then circulated and agitated by the Horiba particle size analyzer. Particle size analysis was conducted using a mobile phase of isopropyl alcohol and the volume average particle size distribution was calculated.

Microflow Imaging: Flow imaging microscopy (Flow-Cam, Fluid Imaging Technologies) was performed to quantify subvisible particulates in protein LDS and the particle formulation. Particles were first redissolved using the particle dissolution method described above and diluted to 1 mg/mL with ultrapure water. For analysis, the aqueous sample was introduced at a flow rate of 0.15 mL/min. The resulting particle counts are recorded and reported per mg of protein.

Results: The stability of dry particles and particle suspensions were evaluated alongside the protein liquid drug substance (LDS). Stability was tracked at 5, 25, and 40° C. with data collected at 7, 14, 28, 60 and 90 days. Particle stability, protein stability, and suspension were measured at each time and temperature. Analysis of the particles and particle suspensions confirmed that protein quality remained constant as measured by the monomer profile (SEC), maintenance of charge variant profile (CEX), isoforms/presumed oxidation (HIC), and colloidal stability (turbidity and subvisible particles). In each case, the protein feed solution was measured against the particles and particle suspensions. Particles stored as dry powder and particle suspension at 5, 25, and 40° C. showed a smooth, spherical morphology. Over the course of three months at these temperatures, no change in the particle morphology or the particle size distribution was observed. The moisture content of the particles remained constant for all storage temperatures and length of time. Analysis of protein aggregates were measured by SEC up to 90 days at 5, 25, and 40° C. The rate of aggregation for the particles and particle suspensions demonstrated improved stability as compared to protein LDS. The charge variant profile of protein was measured by SCEX up to 90 days at 5, 25, and 40° C. No appreciable change was observed for particles and particle suspensions which demonstrated improved stability at 40° C. as compared to protein LDS. HIC was used to measure potential oxidation of protein. The degree of presumed global oxidation of protein was measured by HIC up to 90 days at 5, 25, and 40° C. No appreciable change was observed indicating that the particles and particle suspensions demonstrated improved stability with respect to oxidative stress at 25 and 40° C. as compared to protein LDS at the same temperatures and times. To further probe the protein quality of the redissolved particles, visible and subvisible particulates were analyzed after storage at various temperatures. Upon dissolution, the protein solutions were essentially free of visible particulates and subvisible particulates after storage at 40° C. up to 90 days. Protein concentration, viscosity and syringe force did not significantly change at all storage times and temperatures. Concentration analysis indicated no change in protein concentration at all storage times and temperatures. Viscosity also did not significantly change at all storage times and temperatures. Syringe force did not significantly change at all storage times and temperatures.

Example 16. Determination of Viscosity

General Protocol: A 25 mm 3-degree cone (CP25-3, Anton Paar) is loaded onto the rheometer (Anton Paar Modular Compact Rheometer (MCR) Series 92). The plate is warmed up to 25° C. The suspension was vortexed until visually homogenous. 250 uL is pipetted onto the base plate and the samples were measured at a shear rate of 950 l/s.

Example 17. Determination of Protein Content

Suspensions were redispersed by vortexing, diluted to 2.5% (v/v) in ultrapure water and shaken at 60 RPM for 30 minutes; corresponding dry powder samples were dissolved to 5% (w/v) in ultrapure water and shaken at 60 RPM for 30 minutes. After determining triplicate protein concentrations (from the bottom or aqueous layer for suspensions), the % mass of protein in particles was calculated by dividing the product of the averaged re-dissolved protein particle concentration and redissolution volume by the mass of microparticles. The averaged concentration of suspensions (corrected by aqueous/formulation carrier liquid dilution factor) is then divided by this % mass of protein in particles to calculate the theoretical mass of particles in suspension.

Example 18. Determination of Aggregation, Fragmentation and Change in Charge Variants SEC: Dry powder samples were dissolved to 5% (w/v) in ultrapure water and shaken at 60 RPM. After determining triplicate protein concentrations, the samples were diluted to 1 mg/mL with PBS and syringe filtered into HPLC vials. Samples in carrier liquid were resuspended and each sample was immediately centrifuged at 500 RPM, with the resulting carrier liquid supernatant being aspirated (and discarded) without disturbing the sedimented particles. After adding water to the particles and mixing, the samples were shaken at 60 RPM. Following an initial protein concentration determination (from the bottom or aqueous layer), each sample was diluted with PBS and the protein concentration was measured in triplicate (from the bottom or aqueous layer). Each sample was then diluted with PBS and syringe filtered into HPLC vials, with the needle being discarded before filtration (to prevent transfer of carrier liquid). All samples were analyzed using an Agilent 1260 Infinity II Bio-inert LC System and TSKgel SuperSW HTP column (4 μm, 4.6 mmID×150 mmL) column equilibrated with 200 mM Arginine-HCl, 100 mM Sodium Phosphate pH 6.5. The autosampler and column compartment were maintained at 4° C. and 20° C., respectively, and UV absorbance was monitored at 280 nm. The run time was 10 minutes. The % areas of the integrated high molecular weight (aggregates), monomer and low molecular weight peaks were reported.

SCEX: Dry powder samples were dissolved to 5% (w/v) in ultrapure water and shaken at 60 RPM. After determining triplicate protein concentrations, the samples were diluted with ultrapure water and syringe filtered into HPLC vials. Samples in carrier liquid were resuspended and each sample was immediately centrifuged at 500 RPM, with the resulting carrier liquid supernatant being aspirated (and discarded) without disturbing the sedimented particles. After adding water to the particles and mixing, the samples were shaken at 60 RPM. Following an initial protein concentration determination (from the bottom or aqueous layer), each sample was diluted with ultrapure water and the protein concentration was measured in triplicate (from the bottom or aqueous layer). Each sample was then diluted with ultrapure water and syringe filtered into HPLC vials, with the needle being discarded before filtration (to prevent transfer of carrier liquid). All samples were analyzed using an Agilent 1260 Infinity II Bio-inert LC System and Thermo Scientific MAbPac™ SCX-10 RS column (5 μm, 2.1 mmID×150 mmL) equilibrated with 100% mobile phase A (Thermo Scientific 1×CX-1 pH Gradient Buffer A). The gradient is 0-20% mobile phase B (Thermo Scientific 1×CX-1 pH Gradient Buffer B). The autosampler and column compartment were maintained at 4° C. and 30° C., respectively, and UV absorbance was monitored at 280 nm. The % areas of the integrated acidic, neutral (main) and basic peaks were reported.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific aspects and embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed is:

1. A pharmaceutically effective composition comprising particles suspended in a carrier comprising fatty acid esters, wherein a plurality of the particles comprise at least one antibody or a fragment thereof, wherein the total weight percent of the at least one antibody or the fragment thereof in the plurality of particles is greater than 65%, and wherein the composition further comprises a hyaluronan degrading agent.

2. The composition of claim 1, wherein the carrier comprises fatty acid ethyl esters.

3. The composition of claim 1, wherein the carrier comprises ethyl oleate.

4. The composition of claim 1, wherein the particles have less than 10% aggregation of the at least one antibody or the fragment thereof.

5. The composition of claim 1, wherein the particles have less than 5% aggregation of the at least one antibody or the fragment thereof.

6. The composition of claim 1, wherein the particles have less than 3% aggregation of the at least one antibody or the fragment thereof.

7. The composition of claim 1, wherein the particles have a circularity from 0.80 to 1.00.

8. The composition of claim 1, wherein the particles have less than 3% residual moisture by weight.

9. The composition of claim 1, wherein the particles have greater than 70% of the at least one antibody or the fragment thereof by weight.

10. The composition of claim 1, wherein the particles have greater than 80% of the at least one antibody or the fragment thereof by weight.

11. The composition of claim 1, wherein the particles have less than 3% change in charge variants of the at least one antibody or the fragment thereof.

12. The composition of claim 1, wherein the particles further comprise at least one excipient selected from a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, a nutrient media, analgesic, or a combination thereof.

13. The composition of claim 1, wherein the concentration of the at least one antibody or the fragment thereof in the composition is from 300 mg/mL to 650 mg/mL.

14. The composition of claim 1, wherein the concentration of the at least one antibody or the fragment thereof in the composition is from 400 mg/mL to 650 mg/mL.

15. The composition of claim 1, wherein the composition has a viscosity of less than 100 mPa·s.

16. A pharmaceutically effective composition comprising particles suspended in a carrier comprising ethyl oleate, wherein a plurality of the particles comprise at least one antibody or fragment thereof, and have diameters in the range of 10 μm to 50 μm, wherein the total weight percent of the at least one antibody or fragment thereof in the plurality of particles is greater than 65%, wherein the concentration of the at least one antibody or the fragment thereof in the composition is from 300 mg/mL to 650 mg/mL, and wherein the composition further comprises a hyaluronan degrading agent.

17. The composition of claim 1, wherein the carrier comprises propylene glycol diesters.

18. The composition of claim 1, wherein the hyaluronan degrading agent is a hyaluronidase.

* * * * *